United States Patent
Horvath et al.

(10) Patent No.: US 6,663,863 B2
(45) Date of Patent: *Dec. 16, 2003

(54) METHOD OF INHIBITING STENOSIS AND RESTENOSIS

(75) Inventors: Christopher J. Horvath, Taunton, MA (US); Patricia E. Rao, Acton, MA (US)

(73) Assignee: Millennium Pharmaceuticals, Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/809,739

(22) Filed: Mar. 15, 2001

(65) Prior Publication Data

US 2002/0106369 A1 Aug. 8, 2002

Related U.S. Application Data

(63) Continuation-in-part of application No. 09/528,267, filed on Mar. 17, 2000, now abandoned.

(51) Int. Cl.$^7$ .................. A61K 39/395; C07K 16/28
(52) U.S. Cl. .................. 424/144.1; 424/130.1; 424/133.1; 424/137.1; 424/141.1; 424/143.1; 424/152.1; 424/153.1; 424/154.1; 424/172.1; 424/173.1; 424/184.1; 530/350; 530/395; 530/387.1; 530/387.3; 530/387.5; 530/388.1; 530/388.2; 530/388.22; 530/388.7; 530/388.73; 530/388.75
(58) Field of Search .................. 424/130.1, 133.1, 424/137.1, 141.1, 143.1, 144.1, 152.1, 153.1, 154.1, 172.1, 173.1, 184.1; 530/350, 395, 387.1, 387.3, 387.5, 388.1, 388.2, 388.22, 388.7, 388.73, 388.75

(56) References Cited

U.S. PATENT DOCUMENTS

| | | |
|---|---|---|
| 4,797,277 A | 1/1989 | Arfors |
| 4,840,793 A | 6/1989 | Todd, III et al. |
| 4,935,234 A | 6/1990 | Todd, III et al. |
| 5,019,648 A | 5/1991 | Schlossman et al. |
| 5,147,637 A | 9/1992 | Wright et al. |
| 5,219,997 A | 6/1993 | Schlossman et al. |
| 5,225,539 A | 7/1993 | Winter |
| 5,284,931 A | 2/1994 | Springer et al. |
| 5,340,800 A | 8/1994 | Liu et al. |
| 5,440,021 A | 8/1995 | Chuntharapai et al. |
| 5,475,091 A | 12/1995 | Springer et al. |
| 5,543,503 A | 8/1996 | Chuntharapai et al. |
| 5,585,089 A | 12/1996 | Queen et al. |
| 5,622,700 A | 4/1997 | Jardieu et al. |
| 5,693,761 A | 12/1997 | Queen et al. |
| 5,693,762 A | 12/1997 | Queen et al. |
| 5,817,515 A | 10/1998 | Gallatin et al. |
| 5,821,337 A | 10/1998 | Carter et al. |
| 5,859,205 A | 1/1999 | Adair et al. |
| 5,877,295 A | 3/1999 | Diamond et al. |
| 5,880,268 A | 3/1999 | Gallatin et al. |
| 5,888,508 A | 3/1999 | Hildreth |
| 5,914,112 A | 6/1999 | Bednar et al. |
| 5,985,279 A | 11/1999 | Waldmann et al. |
| 5,997,867 A | 12/1999 | Waldmann et al. |
| 6,084,075 A | 7/2000 | Lind et al. |
| 6,312,689 B1 | 11/2001 | LaRosa |
| 6,352,832 B1 | 3/2002 | LaRosa et al. |
| 6,395,497 B1 | 5/2002 | LaRosa |
| 6,406,694 B1 | 6/2002 | LaRosa |
| 6,406,865 B2 | 6/2002 | LaRosa |
| 2002/0015700 A1 | 2/2002 | LaRosa |
| 2002/0028436 A1 | 3/2002 | LaRosa |
| 2002/0037285 A1 | 3/2002 | LaRosa |
| 2002/0051781 A1 | 5/2002 | LaRosa |
| 2002/0051782 A1 | 5/2002 | LaRosa |
| 2002/0150576 A1 * | 10/2002 | LaRosa et al. |

FOREIGN PATENT DOCUMENTS

| | | |
|---|---|---|
| EP | 0 346 078 A2 | 12/1989 |
| EP | 0 364 690 A2 | 4/1990 |
| EP | 0 438 310 A1 | 7/1991 |
| EP | 0 438 312 A2 | 7/1991 |
| EP | 0 440 351 A2 | 8/1991 |
| EP | 0 578 515 A2 | 1/1994 |
| WO | WO 89/04174 | 5/1989 |
| WO | WO 90/07861 | 7/1990 |
| WO | WO 90/13316 | 11/1990 |
| WO | WO 91/09967 | 7/1991 |
| WO | WO 92/03473 | 3/1992 |
| WO | WO 92/11870 | 7/1992 |
| WO | WO 93/02191 | 2/1993 |
| WO | WO 94/12214 | 6/1994 |
| WO | WO 95/08576 | 3/1995 |
| WO | WO 95/29243 | 11/1995 |
| WO | WO 97/26912 | 7/1997 |
| WO | WO 98/42360 | 1/1998 |
| WO | WO 99/15666 | 4/1999 |
| WO | WO 00/05265 | 2/2000 |

OTHER PUBLICATIONS

Huang Pharmacol. Therapeutics 2000 86:201–215.*
Golino, P., et al., "Inhibition of Leukocyte and Platelet Adhesion Reduces Neointimal Hyperplasia After Arterial Injury," *Thrombosis and Haemostasis*, 77(4):783–788 (1997).

(List continued on next page.)

*Primary Examiner*—Phillip Gambel
*Assistant Examiner*—Jessica H. Roark
(74) *Attorney, Agent, or Firm*—Hamilton, Brook, Smith & Reynolds, P.C.

(57) ABSTRACT

The invention relates to a method of inhibiting stenosis or restenosis in a subject. In one embodiment, an agent which inhibits recruitment and/or adhesion of neutrophils and mononuclear cells to a site of vascular injury is administered to a subject in need thereof. In another embodiment, a first agent which inhibits recruitment and/or adhesion of neutrophils to a site of vascular injury, and a second agent which inhibits recruitment and/or adhesion of mononuclear cells to a site of vascular injury are administered to a subject in need thereof. In particular embodiments, the agents are antibodies or antigen-binding fragments thereof which bind to CD18 or CCR2.

5 Claims, 24 Drawing Sheets

OTHER PUBLICATIONS

Inoue, T., et al., "Clinical Significance of Neutrophil Adhesion Molecules Expression after Coronary Angioplasty on the Development of Restenosis," *Thromb Heamost.* 79:54–58 (1998).

Boring, L., et al., "Decreased Lesion Formation in CCR2–/–Mice Reveals Role for Chemokines in the Initiation of Atherosclerosis," *Nature*, 394(6696):894–897 (1998).

Inoue, T., et al., "Lower Expression of Neutrophil Adhesion Molecule Indicates Less Vessel Wall Injury and Might Explain Lower Restenosis Rate After Cutting Balloon Angioplasty," *Circulation.* 97:2511–2518 (1998).

Rogers, C., et al., "A mAb to the $\beta_2$–Leukocyte Integrin Mac–1 (CD11b/CD18) Reduces Intimal Tickening After Angioplasty or Stent Implanation in Rabbits," *Proc. Natl. Acad. Sci. USA*, 95:10134–10139 (1998).

Simon, D.I., et al., "Decreased Neointimal Formation in Mac–1$^{-/-}$ Mice Reveals a Role for Inflammmation in Vascular Repair After Angioplasty," *J. Clin. Invest.* 105:1–8 (2000).

Simon, D.I., et al., "7E3 Monoclonal Antibody Directed Against the Platelet Glycoprotein IIb/IIIa Cross–reacts With the Leukocyte Integrin Mac–1 and Blocks Adhesion to Fibrinogen and ICAM–1," *Arterioscler. Thromb. Vasc. Biol.* 17:528–535 (1997).

Guzman, L.A., et al., "Role of Leukocyte in Neointimal Formation After Balloon Angioplasty in the Rabbit Atherosclerotic Model," *Coronary Artery Disease*, 6(9):693–701 (1995).

Bishop, G.G., et al., "$\alpha_v\beta_3$ Receptor Blockade Reduces Restonosis Following Balloon Angioplasty in the Atherosclerotic Rabbit," Abstract 1039–60, [online] 1999 [retrieved on Mar. 20, 2000] Retrieved from the internet: <URL://ex2.excerptamedica.com/99acc/abstracts/abs1039–60.html>.

Eichacker, P.Q., et al., "Leukocyte CD18 Monoclonal Antibody Worsens Endotoxemia and Cardiovascular Injury in Canines with Septic Shock," *J. Appl. Physiol.*, 74(4):1885–1892 (1993).

Locey, B.J., et al., "The Role of CD11/CD18 Integrin Molecules in Neutrophil and Monocyte Homotypic Adhesion," In: Leukocyte Typing IV, W. Knapp, et al., Eds. (Oxford: Oxford University Press), 555–558 (1989).

Marijianowski, M.M., et al., "Abciximab Reduces Vascular Lesion Formation in Non–Human Primates," Abstract No. 845–1, [online] 1999 [retrieved on Mar. 15, 2000] Retrieved from the internet: <URL: //ex2.excerptamedica.com/99acc/abstracts/abs845–1.html>.

Mileski, W.J., et al., "Inhibition of CD18–dependent Neutrophil Adherence Reduces Organ Injury After Hemorrhagic Shock in Primates," *Surgery* 108:206–212 (1990).

Mulligan, M.S., et al., "Lung Injury After Deposition of IgA Immune Complexes: Requirements for CD18 and L–Arginine," *J. Immunol.* 148(10):3086–3092 (1992).

Price, T.H., et al., "In Vivo Inhibition of Neutrophil Function in the Rabbit Using Monoclonal Antibody to CD18[1]," *J. Immunol.* 139(12):4174–4177 (1987).

"Experimental Models of Cardiovascular Disease: Concepts, Relevance, and Results," One–Day Workshop sponsored by Primedica, Mar. 19, 2000, Philadelphia, Pennsylvania.

Furukawa, Y., et al., "Anti–Monocyte Chemoattractant Protein–1/Monocyte Chemotactic and Activating Factor Antibody Inhibits Neointimal Hyperplasia in Injured Rat Carotid Arteries," *Circ. Res.*, 84:306–314 (1999).

Sharar, S.R., et al., "A CD18 Monoclonal Antibody Increases the Incidence and Severity of Subcutaneous Abscess Formation After High–Dose *Staphylococcus aureus* Injection in Rabbits," *Surgery*, 110:213–220 (1991).

Arfors, Karl–E., et al., "A Monoclonal Antibody to the Membrane Glycoprotein Complex CD18 Inhibits Polymorphonuclear Leukocyte Accumulation and Plasma Leakage In Vivo," *Blood*, 69(1):338–340 (1987).

Doerschuk, C.M., et al., "CD18–Dependent and –Independent Mechanisms of Neutrophil Emigration in the Pulmonary and Systemic Microcirculation of Rabbits[1]," *J. Immunol.*, 144(6):2327–2333 (1990).

Vedder, N.B., et al., "A Monoclonal Antibody to the Adherence–promoting Leukocyte Glycoprotein, CD18, Reduces Organ Injury and Improves Survival from Haemorrhagic Shock and Resuscitation in Rabbits," *J. Clin. Invest.*, 81:939–944 (1988).

Welt, F.G.P., et al., "Neutrophil, Not Macrophage, Infiltration Precedes Neointimal Thickening After Endothelial Denudation," Abstract from American Heart Association, [online] 1999 [retrieved on Mar. 20, 2000] retrieved from the internet: <URL: //aha99.agora.com/abstractviewer/viewabstracts.esp>.

Boring, L., et al., "Impaired Monocyte Migration and Reduced Type 1 (Th1) Cytokine Responses in C–C Chemokine Receptor 2 Knockout Mice," *J. Clin. Invest.*, 100:2552–2561 (1997).

Gu, L. et al., "Absence of Monocyte Chemoattractant Protein–1 Reduces Atherosclerosis in Low Density Lipoprotein Receptor–Deficient Mice," *Molecular Cell*, 2:275–281 (1998).

Gunn, M.D., et al., "Monocyte Chemoattractant Protein–1 is Sufficient for the Chemotaxis of Monocyte and Lymphocytes in Transgenic Mice but Requires an Additional Stimulus for Inflammatory Activation," *J. Immunol.*, 158:376–383 (1997).

Kurihara, T., et al., "Defects in Macrophage Recruitment an Host Defense in Mice Lacking the CCR2 Chemokine Receptor," *J. Exp. Med.*, 186(10):1757–1762 (1997).

Kuziel, W.A., et al., "Severe Reaction in Leukocyte Adhesion and Monocyte Extravasation in Mice Deficient in CC Chemokine Receptor 2," *Proc. Natl. Acad. Sci. USA*, 94:12053–12058 (1997).

Lu, B., et al., "Abnormalities in Monocyte Recruitment and Cytokine Expression in Monocyte Chemoattractant Protein 1–deficient Mice," *J. Exp. Med.*, 187(4):601–608 (1998).

Nelken, N.A., et al., "Monocyte Chemoattractant Protein–1 in Human Atheromatous Plaques," *J. Clin. Invest.*, 88:1121–1127 (1991).

Rand, M.L., et al., "Inhibition of T Cell Recruitment and Cutaneous Delayed–Type Hypersensitivity–Induced Inflammation with Antibodies to Monocyte Chemoattractant Protein–1," *Am. J. Pathol.*, 148(3):855–864 (1996).

Sims, M.J., et al., "A Humanized CD18 Antibody Can Block Function Without Cell Destruction," *J. Immunol.*, 151(4):2296–2308 (1993).

Taubman, M.B., et al., "JE mRNA Accumulates Rapidly in Aortic Injury and in Platelet–Derived Growth Factor–Stimulated Vascular and Smooth Muscle Cells," *Circ. Res.*, 70:314–325 (1992).

Ward, P.A. and M.S. Mulligan, "Blocking of Adhesion Molecules in vivo as Anti–inflammatory Therapy," *Therapeutic Immunol.* 1:165–171 (1994).

Winn, R.K., et al., "Monoclonal Antibodies to Leukocyte and Endothelial Adhesion Molecules Attenuate Ischemia–Reperfusion Injury," *Behring Inst. Mitt.*, 92:229–237 (1993).

Ylä–Herttuala, S., et al., "Expression of Monocyte Chemoattractant Protein 1 in Macrophage–rich Areas of Human and Rabbit Atherosclerosis Lesions," *Proc. Natl. Acad. Sci. USA*, 88:5252–5256 (1991).

Huang, C., et al., "Folding of the Conserved Domain but not of Flanking Regions in the Integrin $\beta_2$ Subunit Requires Association with the $\alpha$ Subunit," *Proc. Natl. Acad. Sci. USA*, 94:3156–3161 (1997).

Johnston, B. et al., "Chronic Inflammation Upregulates Chemokine Receptors and Induces Neutrophil Migration to Monocyte Chemoattractant Protein–1," *Journal of Clinical Investigation*, 103(9):1269–1276 (1999).

Welt, F.G.P. et al., "Targeting CCR–2 or CD18 Inhibits Experimental In–Stent Restenosis in Primates. Inhibitory Potential Depends on Type of Injury and Leukocyte Targeted," *Circulation*, 102(18 Supplement):II.247 (2000).

Jones, R., "Rovelizumab ICOS Corp," *Current Opinion in Cardiovascular, Pulmonary & Renal Investigational Drugs*, 1(5):672–676 (1999).

Lumsden, A.B. et al. "Anti–VLA–4 Antibody Reduces Intimal Hyperplasia in the Endarterectomized Carotid Artery in Nonhuman Primates," *Journal of Vascular Surgery*, 26(1):87–93 (1997).

Kling, D. et al., "Mononuclear Leukocytes Invade Rabbit Arterial Intima During Thickening Formation via CD18–and VLA–4–Dependent Mechanisms and Stimulate Smooth Muscle Migration," *Circulation Research*, 77(6):1121–1128 (1995).

Gray, J.L. and Shankar, R., "Down Regulation of CD11b and CD18 Expression in Atherosclerotic Lesion–Derived Macrophages," *The American Surgeon*, 61(8):674–680 (1995).

Languino, L.R. et al., "Regulation of Leukocyte–Endothelium Interaction and Leukocyte Transendothelial Migration by Intercellular Adhesion Molecule 1–Fibrinogen Recognition," *Proc. Natl. Acad. Sci. USA*, 92:1505–1509 (1995).

Inoue, T. et al., "Expression of Polymorphonuclear Leukocyte Adhesion Molecules and Its Clinical Significance in Patients Treated with Percutaneous Transluminal Coronary Angioplasty," *J. Am. Coll. Cardiol.*, 28(5):1127–1133 (1996).

Mickelson, J.K. et al., "Leukocyte Activation with Platelet Adhesion After Coronary Angioplasty: A Mechanism for Recurrent Disease?," *J. Am. Coll. Cardiol.*, 28(2):345–353 (1996).

Russell, P.S. et al., "Coronary Atherosclerosis in Transplanted Mouse Hearts," *Transplantation*, 60(7):724–729 (1995).

Yasukawa, H. et al., "Inhibition of Intimal Hyperplasia After Balloon Injury by Antibodies to Intercellular Adhesion Molecule–1 and Lymphocyte Function–Associated Antigen–1," *Circulation*, 95(6):1515–1522 (1997).

Serrano, C.V. et al., "Coronary Angioplasty Results in Leukocyte and Platelet Activation with Adhesion Molecule Expression," *J. Am. Coll. Cardiol.*, 29(6):1276–1283 (1997).

Deitch, J.S. et al., "Effects of $\beta$3–Integrin Blockade (c7e3) on the Response to Angioplasty and Intra–Arterial Stenting in Atherosclerotic Nonhuman Primates," *Arterioscler Thromb Vasc Biol.*, 18:1730–1737 (1998).

Kassirer, M. et al., "Increased Expression of the CD11b/CD18 Antigen on the Surface of Peripheral White Blood Cells in Patients with Ischemic Heart Disease: Further Evidence for Smoldering Inflammation in Patients with Atherosclerosis," *Am Heart J*, 138:555–559 (1999).

Van Put, D.J.M. et al., "Role of Polymorphonuclear Leukocytes in Collar–Induced Intimal Thickening in the Rabbit Carotid Artery," *Arterioscler Thromb Vasc Biol*, 18:915–921 (1998).

Ricevuti, G. et al., "Role of Granulocytes in Endothelial Injury in Coronary Heart Disease in Humans," *Atherosclerosis*, 91:1–14 (1991).

Kling, D. et al., "Inhibition of Leukocyte Extravasation with a Monoclonal Antibody to CD18 During Formation of Experimental Intimal Thickening in Rabbit Carotid Arteries," *Arteriosclerosis and Thrombosis*, 12(9):997–1007 (1992).

Wautier, J.L., "Relations Monocytes–Endothélium," *Journal des Maladies Vasculaires*, 14:13–16 (1989). (Abstract only).

* cited by examiner

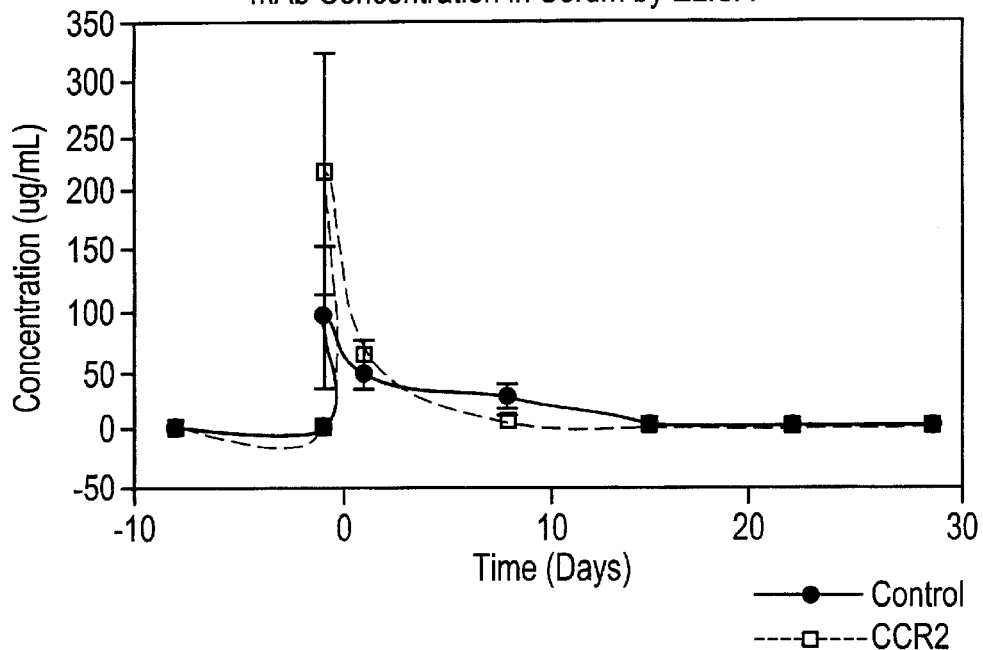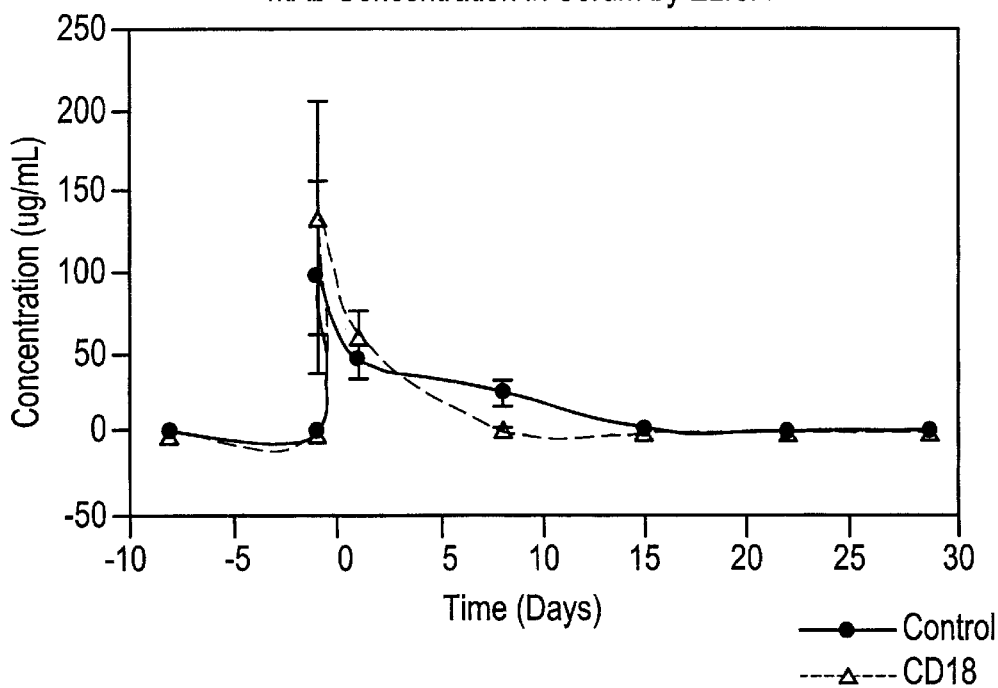

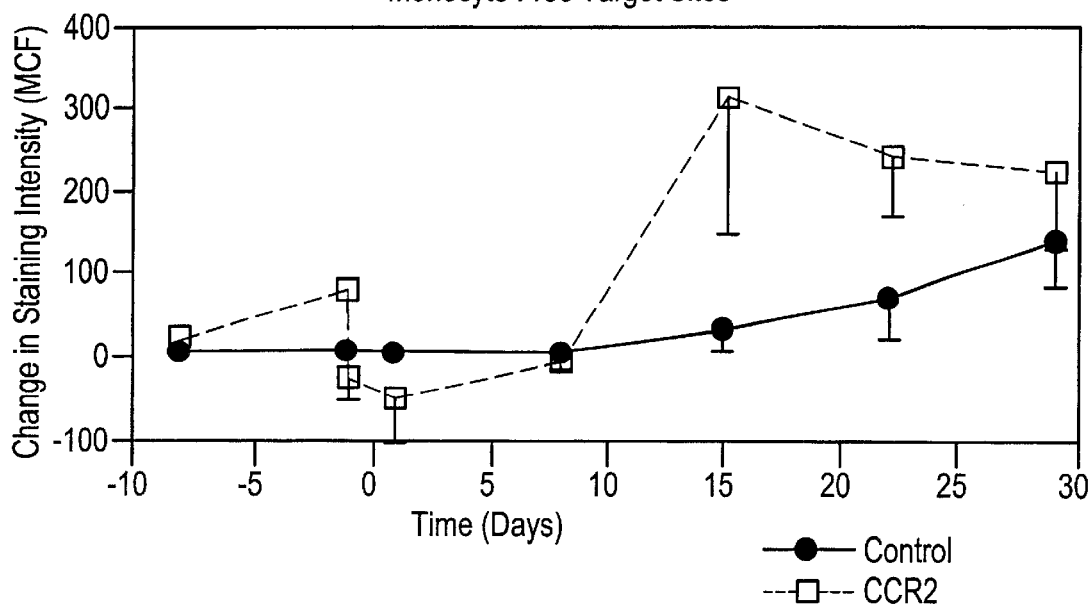
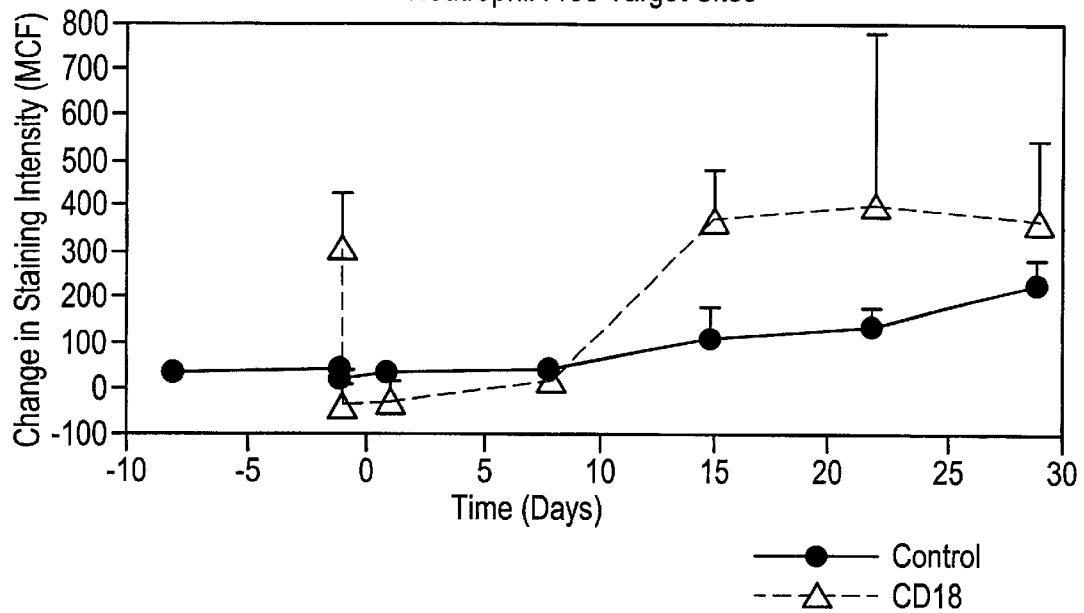

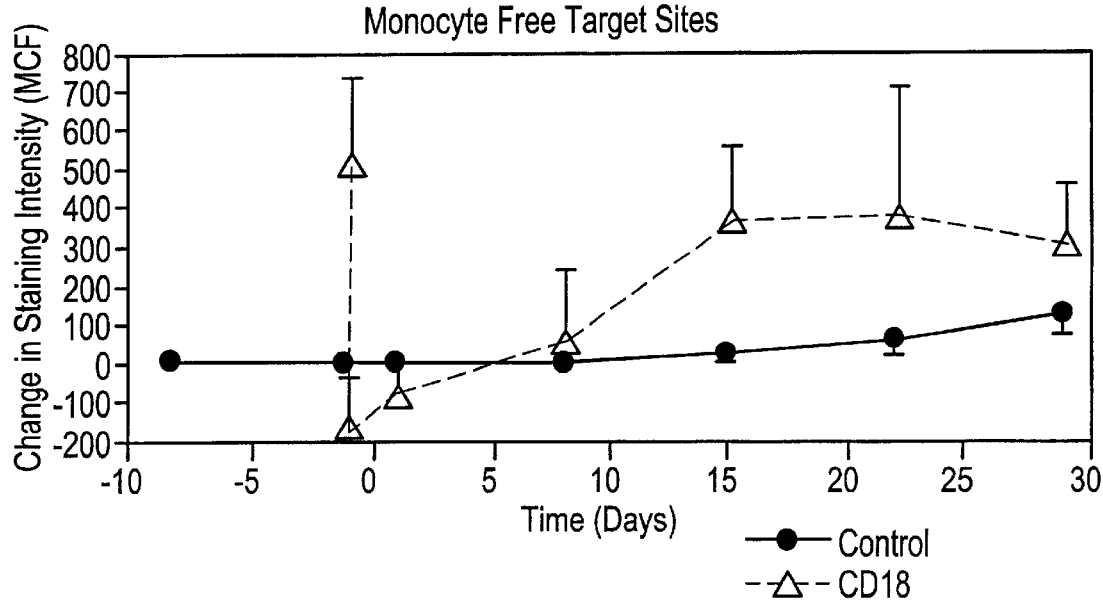
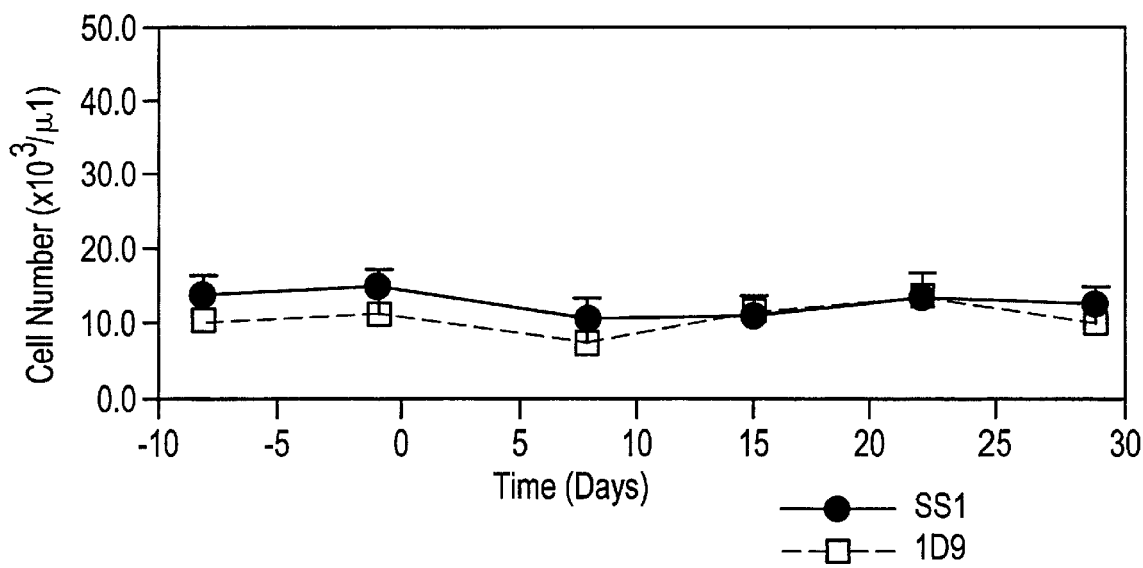

Total Neutrophil Count

Total Lympohocyte Count

Total Monocyte Count

Total WBC Count

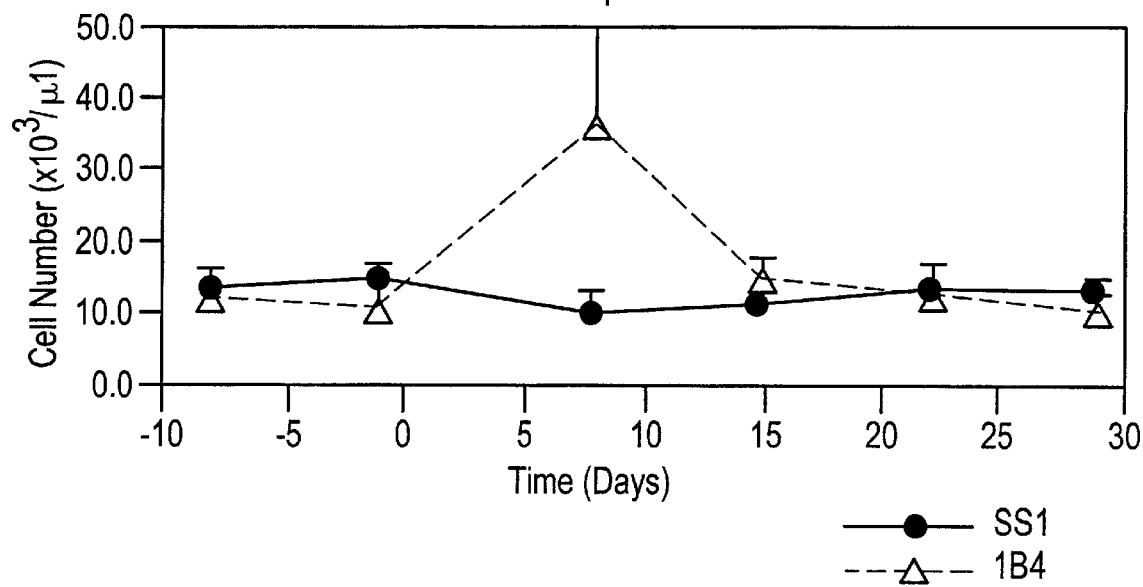
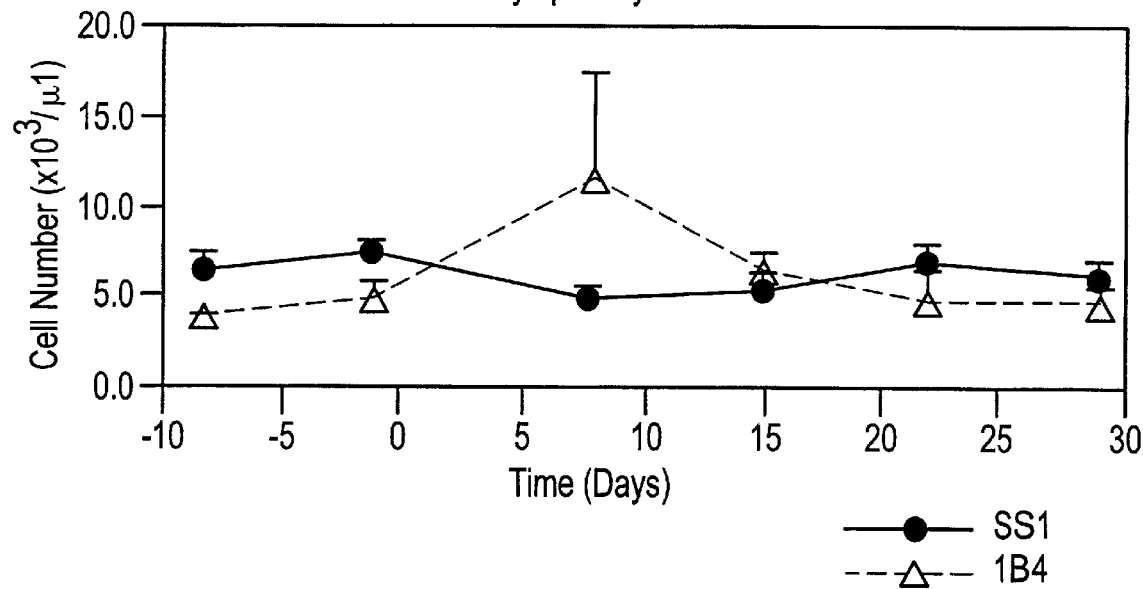

Total Monocyte Count

Luminal Diameter

Late Luminal Loss

Index=LLL/ALG

Luminal Diameter

Late Luminal Loss

Index=LLL/ALG

Met Arg Val Gln Val Gln Phe Leu Gly Leu Leu Leu Leu Trp Thr Ser

Gly Ala Gln Cys Asp Val Gln Met Thr Gln Ser Pro Ser Tyr Leu Ala

Ala Ser Pro Gly Glu Ser Val Ser Ile Ser Cys Lys Ala Ser Lys Ser

Ile Ser Asn Tyr Leu Ala Trp Tyr Gln Gln Lys Pro Gly Glu Ala Asn

Lys Leu Leu Val Tyr Tyr Gly Ser Thr Leu Arg Ser Gly Ile Pro Ser

Arg Phe Ser Gly Ser Gly Ser Gly Thr Asp Phe Thr Leu Thr Ile Arg

Asn Leu Glu Pro Ala Asp Phe Ala Val Tyr Tyr Cys Gln Gln Tyr Tyr

Glu Arg Pro Leu Thr Phe Gly Ser Gly Thr Lys Leu Glu

Fig. 9

CDR1  Lys Ala Ser Lys Ser Ile Ser Asn Tyr Leu Ala

CDR2  Tyr Gly Ser Thr Leu Arg Ser

CDR3  Gln Gln Tyr Tyr Glu Arg Pro Leu Thr

Fig. 10

Met Lys Cys Ser Trp Ile Asn Leu Phe Leu Met Ala Leu Ala Ser Gly

Val Tyr Ala Glu Val Gln Leu Gln Gln Ser Gly Pro Glu Leu Arg Arg

Pro Gly Ser Ser Val Lys Leu Ser Cys Lys Thr Ser Gly Tyr Ser Ile

Lys Asp Tyr Leu Leu His Trp Val Lys His Arg Pro Glu Tyr Gly Leu

Glu Trp Ile Gly Trp Ile Asp Pro Glu Asp Gly Glu Thr Lys Tyr Gly

Gln Lys Phe Gln Ser Arg Ala Thr Leu Thr Ala Asp Thr Ser Ser Asn

Thr Ala Tyr Met Gln Leu Ser Ser Leu Thr Ser Asp Asp Thr Ala Thr

Tyr Phe Cys Thr Arg Gly Glu Tyr Arg Tyr Asn Ser Trp Phe Asp Tyr

Trp Gly Gln Gly Thr Leu Val Thr Val Ser Ser

Fig. 11

CDR1  Asp Tyr Leu Leu His

CDR2  Trp Ile Asp Pro Glu Asp Gly Glu Thr Lys Tyr Gly Gln Lys Phe Gln Ser

CDR3  Gly Glu Tyr Arg Tyr Asn Ser Trp Phe Asp Tyr

Fig. 12

1 MGWSCIILFL VATATGVHSQ VQLQESGPGL VRPSQTLSLT CTVSGFTFTD

51 YLLHWVRQPP GRGLEWIGWI DPEDGETKYG QKFQSRVTML VDTSKNQFSL

101 RLSSVTAADT AVYYCARGEY RYNSWFDYWG QGSLVTVSS

Fig. 13

1 MGWSCIILFL VATATGVHSD IQMTQSPSSL SASVGDRVTI TCKASKSISN

51 YLAWYQQKPG KAPKLLIYYG STLRSGVPSR FSGSGSGTDF TFTISSLQPE

101 DIATYYCQQY YERPLTFGQG TKVEIKR

Fig. 14

```
  1 DVVMTQTPLT LSVTVGHPAS ISCKSSQSLL DSDGKTFLNW LLQRPGQSPK

51 RLIYLVSKLD SGVPDRFTGS GSGTDFTLKI SRVEAEDLGV YYCWQGTHFP

101 YTFGGGTKLE IK
```

Fig. 15

```
  1 EVQLVESGGG LVQPKGSLKL SCAASGFSFN AYAMNWVRQA PGKGLEWVAR

51 IRTKNNNYAT YYADSVKDRY TISRDDSESM LFLQMNNLKT EDTAMYYCVT

101 FYGNGVWGTG TTVTVSS
```

Fig. 16

```
CDRs                      ======L1=========       ==L2===                         =====L3=======
Kabat Numbers                                                                                           1
                  1         2         3         4         5         6         7         8         9     0
          1234567890123456789012345678ABCDEF890123456789012345678901234567890123456789012345ABCDEF67890123456A7

1D9 Vκ    DVVMTQTPLTLSVTVGHPASISCKSSQSLLDS-DGKTFLNWLLQRPGQSPKRLIYLVSKLDSGVPDRFTGSGSGTDFTLKISRVEAEDLGVYYCWQGTHFP------YTFGGGTKLEI-K

HF-21/28 Vκ .......S..S.P..L.Q......R.....VH. ..N.Y...FQ......R....K..NR.......S..............V.....M....W.           F...Q.R...

1D9RKA Vκ  DVVMTQSPLSLPVTLGQPASISCKSSQSLLDS-DGKTFLNWFQQRPGQSPRRLIYLVSKLDSGVPDRFSGSGSGTDFTLKISRVEAEDVGVYYCWQGTHFP------YTFGQGTRLEI-K
1D9RKB Vκ  DVVMTQSPLSLPVTLGQPASISCKSSQSLLDS-DGKTFLNWLLQRPGQSPRRLIYLVSKLDSGVPDRFSGSGSGTDFTLKISRVEAEDVGVYYCWQGTHFP------YTFGQGTRLEI-K
1D9RKC Vκ  DVVMTQSPLSLPVTLGQPASISCKSSQSLLDS-DGKTFLNWLLQRPGQSPRRLIYLVSKLDSGVPDRFSGSGSGTDFTLKISRVEAEDVGVYYCWQGTHFP------YTFGQGTRLEI-K
1D9RKD Vκ  DVVMTQSPLSLPVTLGHPASISCKSSQSLLDS-DGKTFLNWLLQRPGQSPRRLIYLVSKLDSGVPDRFSGSGSGTDFTLKISRVEAEDVGVYYCWQGTHFP------YTFGGGTRLEI-K
1D9RKE Vκ  DVVMTQSPLSLPVTLGHPASISCKSSQSLLDS-DGKTFLNWLLQRPGQSPRRLIYLVSKLDSGVPDRFSGSGSGTDFTLKISRVEAEDVGVYYCWQGTHFP------YTFGQGTRLEI-K
```

Key

1D9 Vκ              Mouse 1D9 Vκ region

HF-21/28 Vκ         Chosen human framework acceptor Vκ region sequence with mismatches to the 1D9 Vκ region highlighted.

1D9RKA Vκ           CDR grafted 1D9 Vκ region, with no back mutations but with the added human lysine residue at position 107 (i.e., 107K).

1D9RKB Vκ           CDR grafted 1D9 Vκ region, with back mutations at F36L and Q37L, and the additional 107K insertion.

1D9RKC Vκ           CDR grafted 1D9 Vκ region, with back mutations at F36L, Q37L and Q100G, and the additional 107K insertion.

1D9RKD Vκ           CDR grafted 1D9 Vκ region, with back mutations at F36L, Q37L, Q100G and Q17H, and the additional 107K insertion.

1D9RKE Vκ           CDR grafted 1D9 Vκ region, with back mutations at F36L, Q37L and Q17H, and the additional 107K insertion.

Fig. 17

```
CDRs                        ====H1===                        ========H2========                                                       =====H3======
Kabat Numbers                                    1111111111111111                                                                                     1         1
           1         2         3         4         5         6         7         8         9         0         1
  1234567890123456789012345AB67890123456789012ABC34567890123456789012ABC-IJK123
```

1D9     EVQLVESGGGLVQPKGSLKLSCAASGFSNAYAMN--WVRQAPGKGLEWVARIRTKNNNYATYYADSVKDRYTISRDDSESMLFLQMNNLKTEDTAMYYCVTFYGN-------GVWGTGTTVTVSS

4B4'CL V<sub>H</sub>
        .........K.G...R........T.SNAW.S ..............G..KS.TDGGT.D..AP..G.F......KNT.Y...S.......V...T.DSLPPH     R...Q.L......

1D9RH<sub>A</sub> V<sub>H</sub>
        EVQLVESGGGLVKPGGSLRLSCAASGFTFSAYAMN--WVRQAPGKGLEWVGRIRTKNNNYATYYADSVKDRFTISRDDSKNTLYLQMNSLKTEDTAVYYCTTFYGN-------GVWGQGTLVTVSS 1D9RH<sub>B</sub> V<sub>H</sub>
        EVQLVESGGGLVKPGGSLRLSCAASGFSFNAYAMN--WVRQAPGKGLEWVGRIRTKNNNYATYYADSVKDRFTISRDDSKNTLYLQMNSLKTEDTAVYYCTTFYGN-------GVWGQGTLVTVSS 1D9RH<sub>C</sub> V<sub>H</sub>
        EVQLVESGGGLVKPGGSLRLSCAASGFSFNAYAMN--WVRQAPGKGLEWVARIRTKNNNYATYYADSVKDRYTISRDDSKNTLYLQMNSLKTEDTAVYYCTTFYGN-------GVWGQGTLVTVSS 1D9RH<sub>D</sub> V<sub>H</sub>
        EVQLVESGGGLVKPGGSLRLSCAASGFSFNAYAMN--WVRQAPGKGLEWVARIRTKNNNYATYYADSVKDRYTISRDDSKNTLYLQMNSLKTEDTAVYYCVTFYGN-------GVWGQGTLVTVSS

Key

1D9 V<sub>H</sub>       Mouse 1D9 V<sub>H</sub> region.

4B4'CL V<sub>H</sub>    Chosen human framework acceptor V<sub>H</sub> region sequence with mismatches to the 1D9 V<sub>H</sub> region highlighted.

1D9RH<sub>A</sub> V<sub>H</sub>   CDR grafted 1D9 V<sub>H</sub> region, with no back mutations.

1D9RH<sub>B</sub> V<sub>H</sub>   CDR grafted 1D9 V<sub>H</sub> region, with back mutations at T28S and S30N.

1D9RH<sub>C</sub> V<sub>H</sub>   CDR grafted 1D9 V<sub>H</sub> region, with back mutations at T28S, S30N, G49A and F67Y.

1D9RH<sub>D</sub> V<sub>H</sub>   CDR grafted 1D9 V<sub>H</sub> region, with back mutations at T28S, S30N, G49A, F67Y and T93V.

Fig. 18

METHOD OF INHIBITING STENOSIS AND RESTENOSIS

RELATED APPLICATION

This application is a continuation-in-part of application Ser. No. 09/528,267, filed Mar. 17, 2000, now abandoned, the entire teachings of which are incorporated herein by reference.

BACKGROUND OF THE INVENTION

A stenosis is a stricture of a canal or duct. In the context or the vascular system a stenosis is a narrowing of the lumen of a blood vessel. A stenosis can severely restrict blood flow and promote thrombosis which can lead to myocardial infarction or stroke, for example. A common type of primary stenosis is artherosclerotic plaque. Several therapeutic methods have been developed to improve circulation and hemostasis in stenotic vessels including by-pass surgery and revascularization procedures. Revascularization procedures (e.g., balloon angioplasty, atherectomy, rotorary ablation (rotoblation)) serve to improve blood flow by reducing or removing the stenosis. However, these procedures frequently injure the blood vessel. The biological response to the injury is a multifactorial fibro-proliferative process that is similar to wound healing, and includes the elaboration of growth factors from a variety of cell types, infiltration of leukocytes, migration and proliferation of smooth muscle cells, the production of extracellular matrix and tissue remodeling (Anderson, *Vessels*, 2:4–14 (1996)). The process can result in the formation of a thick neointima within the vessel wall which reduces the luminal area of the vessel (i.e., restenosis). Restenosis occurs following about 20–50% of coronary angioplasty procedures (Anderson, *Vessels*, 2:4–14 (1996)).

Attempts have been made at reducing restenosis following vascular intervention procedures by, for example, administering pharmacologic agents and placement of endovascular stents. However, although stents are reported to partially reduce restenosis (Serruys, et al., *N. Engl. J. Med.*, 331:489–495 (1994)), restenosis and in-stent restenosis remain a significant problem. Therefore, a need exists for new methods for inhibiting stenosis and restenosis.

SUMMARY OF THE INVENTION

The invention relates to a method of inhibiting stenosis or restenosis of a blood vessel following vascular injury. In one embodiment the method comprises administering to a subject in need thereof, a therapeutically effective amount of a first therapeutic agent which inhibits the adhesion and/or recruitment of neutrophils to a site of vascular injury, and a therapeutically effective amount of a second therapeutic agent which inhibits the adhesion and/or recruitment of mononuclear cells to a site of vascular injury. In a certain embodiment, the method is a method of inhibiting stenosis or restenosis following vascular injury which occurs during or is caused by a therapeutic or diagnostic vascular intervention procedure (e.g., angiography, angioplasty, vascular by-pass surgery, vascular grafting, endarterectomy, atherectomy, endovascular stenting, insertion of prosthetic valve and transplantation of organs, tissues or cells). The first and second therapeutic agents can independently be an antagonist of a cellular adhesion molecule or an antagonist of chemokine receptor function, for example. In certain embodiments, the first therapeutic agent binds to an integrin (e.g., a β2 integrin) and inhibits integrin-mediated cellular adhesion. Preferably, the first therapeutic agent binds CD18 and inhibits binding of one or more ligands (e.g., ICAM-1, ICAM-2, ICAM-3, fibrinogen, C3bi, Factor X) to a CD18 containing integrin. In additional embodiments, the second therapeutic agent is a chemokine receptor antagonist. Preferably, the second therapeutic agent can bind CCR2 and inhibit the binding of a ligand (e.g., MCP-1, MCP-2, MCP-3, MCP-4, MCP-5) to the receptor. In preferred embodiments, the first and second therapeutic agents are antibodies or antigen-binding fragments thereof.

In a more particular embodiment, the method is a method of inhibiting stenosis or restenosis in a subject following percutaneous transluminal coronary angioplasty (PTCA). In another particular embodiment, the method is a method of inhibiting stenosis or restenosis in a subject following a vascular intervention procedure which includes placement of a stent. In another embodiment, the method of inhibiting stenosis or restenosis in a subject following vascular injury comprises administering to a subject in need thereof, an effective amount of an agent which inhibits recruitment and/or adhesion of neutrophils and mononuclear cells to a site of vascular injury.

The invention further relates to an agent that inhibits recruitment and/or adhesion of neutrophils or mononuclear cells to sites of vascular injury (e.g. cellular adhesion molecule antagonists (e.g., anti-CD18 antibodies), antagonists of chemokine receptor function (e.g., anti-CCR2 antibodies)) for use in therapy (including prophylaxis) or diagnosis, for example, as described herein, and to the use of such an antagonist for the manufacture of a medicament for the inhibition of stenosis or restenosis. The invention also relates to a medicament for the inhibition of stenosis or restenosis (e.g., following a vascular intervention procedure (e.g., angioplasty, percutanious transluminal coronary angioplasty) wherein said medicament comprises an agent that inhibits recruitment and/or adhesion of neutrophils or mononuclear cells to sites of vascular injury (e.g. cellular adhesion molecules antagonists (e.g., anti-CD18 antibody), antagonist of chemokine receptor function (e.g., anti-CCR2 antibody)).

BRIEF DESCRIPTION OF THE DRAWINGS

FIG. 1A is a graph showing the concentrations of mAb 1D9 (CCR2) or mAb S-S.1 (Control) detected in serum of animals treated with mAb 1D9 or mAb S-S.1 at predetermined time points.

FIG. 1B is a graph showing the concentrations of mAb 1B4 (CD18) or mAb S-S.1 (Control) detected in serum of animals treated with mAb 1B4 or mAb S-S.1 at predetermined time points.

FIG. 2A is a graph showing the amount of unbound CCR2 present on the surface of monocytes of animals treated with mAb 1D9 over time. Free CCR2 was detected by staining blood cells with FITC conjugated anti-mouse IgG or with mAb 1D9 and then with FITC conjugated anti-mouse IgG. The mean channel fluorescence (MCF) was determined for each sample by flow cytometry and the difference in MCF, which indicates the degree to which CCR2 was not saturated, was determined.

FIG. 2B is a graph showing the amount of unbound CD18 present on the surface of neutrophils of animals treated with mAb 1B4 over time. Free CD18 was detected by staining blood cells with FITC conjugated anti-mouse IgG or with mAb 1B4 and then with FITC conjugated anti-mouse IgG. The mean channel fluorescence (MCF) was determined for each sample by flow cytometry and the difference in MCF, which indicates the degree to which CD18 was not saturated, was determined.

FIG. 2C is a graph showing the amount of unbound CD18 present on the surface of monocytes in animals treated with mAb 1B4 over time. Free CD18 was detected by staining blood cells with FITC conjugated anti-mouse IgG or with mAb 1B4 and then with FITC conjugated anti-mouse IgG. The mean channel fluorescence (MCF) was determined for each sample by flow cytometry and the difference in MCF, which indicates the degree to which CD18 was not saturated, was determined.

FIG. 3A is a graph showing the total white blood cell count in the peripheral blood in animals treated with mAb S-S.1 or mAb 1D9 at predetermined time points.

FIG. 3F is a graph showing the total neutrophil count in the peripheral blood in animals treated with mAb S-S.1 or mAb 1B4 at predetermined time points.

FIG. 3G is a graph showing the total lymphocyte count in the peripheral blood in animals treated with mAb S-S.1 or mAb 1B4 at predetermined time points.

FIG. 9 shows the amino acid sequence (SEQ ID NO:1) of rat mAb YFC51.1 light chain variable region. The signal sequence consists of residues 1–20.

FIG. 10 shows the amino acid sequences of complementarity determining regions 1, 2 and 3 (CDR1 (SEQ ID NO:2), CDR2 (SEQ ID NO:3) and CDR3 (SEQ ID NO:4)) of the light chain of rat mAb YFC51.1.

FIG. 11 shows the amino acid sequence (SEQ ID NO:5) of rat mAb YFC51.1 heavy chain variable region. The signal sequence consists of residues 1–19.

FIG. 12 shows the amino acid sequence of CDR1 (SEQ ID NO:6), CDR2 (SEQ ID NO: 7) and CDR3 (SEQ ID NO:8) of the heavy chain of rat mAb YFC51.1.

FIG. 13 shows the amino acid sequence (SEQ ID NO:9) of the heavy chain variable region of LDP-01, a humanized YFC51.1. The signal sequence consists of amino acid residues 1–19.

FIG. 14 shows the amino acid sequence (SEQ ID NO:10) of the light chain variable region of LDP-01, a humanized YFC51.1. The signal sequence consists of residues 1–19.

FIG. 15 shows the amino acid sequence (SEQ ID NO:11) of the light chain variable region of murine mAb 1D9. CDR 1 consists of amino acid residues 24–39, CDR 2 consists of amino acid residues 55–61, CDR 3 consists of amino acid residues 94–102.

FIG. 16 shows the amino acid sequence (SEQ ID NO:12) of the heavy chain variable region of murine mAb 1D9. CDR 1 consists of amino acid residues 31–35, CDR 2 consists of amino acid residues 50–68, CDR 3 consists of amino acid residues 101–106.

FIG. 17 shows the amino acid sequences of the light chain variable region (Vκ) of murine mAb 1D9 (SEQ ID NO:11), the light chain variable region (Vκ) of human antibody HF-21/28 (SEQ ID NO:13) and the variable regions of several humanized 1D9 light chains (1D9RKA Vκ, SEQ ID NO: 14; 1D9RK$_B$ Vκ, SEQ ID NO: 15; 1D9RK$_C$ Vκ, SEQ ID NO: 16; 1D9RK$_D$ Vκ, SEQ ID NO: 17; 1D9RK$_E$ Vκ, SEQ ID NO: 18). Where the amino acid residues of the murine 1D9 light chain variable region (SEQ ID NO:11) and the human HF-21/28 light chain variable region (SEQ ID NO: 13; Kabat database ID number 005056, and Chastagner et al., *Gene*. 101(2):305–6 (1991), the teachings of both of which are incorporated herein by reference in their entirety) sequences match, a dot [.] is shown. Where no amino acid is present at a specific residue position a dash [-] is shown. Where an amino acid in the HF-21/28 frame work region (FR) is changed in a humanized 1D9 variable region, it is highlighted in bold. The CDRs (CDR1, CDR2 and CDR3) are indicated by [==L1==], [==L2==] and [==L3==]. The numbering used is according to Kabat et al., *Sequences of proteins of immunological interest*, Fifth edition, U.S. Department of Health and Human Services, U.S. Government Printing Office (1991).

FIG. 18 shows the amino acid sequences of heavy chain variable region ($V_H$) of murine mAb 1D9 (SEQ ID NO: 12), the heavy chain variable region of human antibody 4B4'CL (SEQ ID NO: 19; Kabat data base ID number 000490, and Sanz et al., *Journal of Immunology*. 142:883 (1989), the teachings of both of which are incorporated herein by reference in their entirety), and the variable regions of several humanized 1D9 heavy chains (1D9RH$_A$ V$_H$, SEQ ID NO: 20; 1D9RH$_B$ V$_H$, SEQ ID NO: 21; 1D9RH$_C$ V$_H$, SEQ ID NO: 22; 1D9RH$_D$ V$_H$, SEQ ID NO: 23). Where the amino acid residues of the murine 1D9 heavy chain variable region (SEQ ID NO: 12) and the human 4B4'CL heavy chain variable region (SEQ ID NO: 19) sequences match, a dot [.] is shown. Where no amino acid is present at a specific residue position a dash [-] is shown. Where an amino acid in the 4B4'CL heavy chain variable region is changed in a humanized 1D9 heavy chain variable region, it is highlighted in bold. The CDRs (CDR1, CDR2 and CDR3) are indicated by [==H1==], [==H2==] and [==H3==], while [- - -] denotes part of the H1 structure loop. The numbering used is according to Kabat et al., *Sequences of proteins of immunological interest*, Fifth edition, U.S. Department of Health and Human Services, U.S. Government Printing Office (1991).

DETAILED DESCRIPTION OF THE INVENTION

Figure 3B:
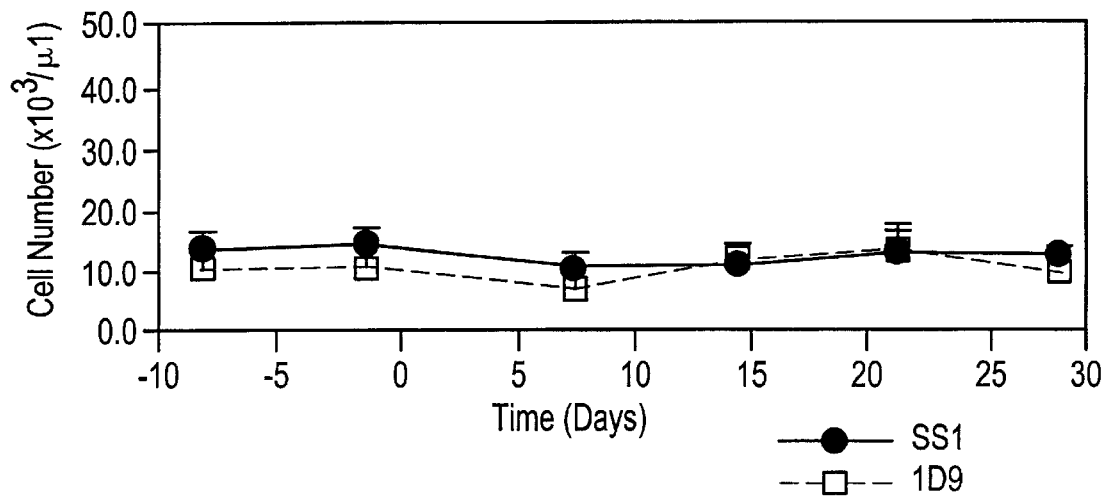
FIG. 3B is a graph showing the total neutrophil cell count in the peripheral blood in animals treated with mAb S-S.1 or mAb 1D9 at predetermined time points.
Figure 3C:
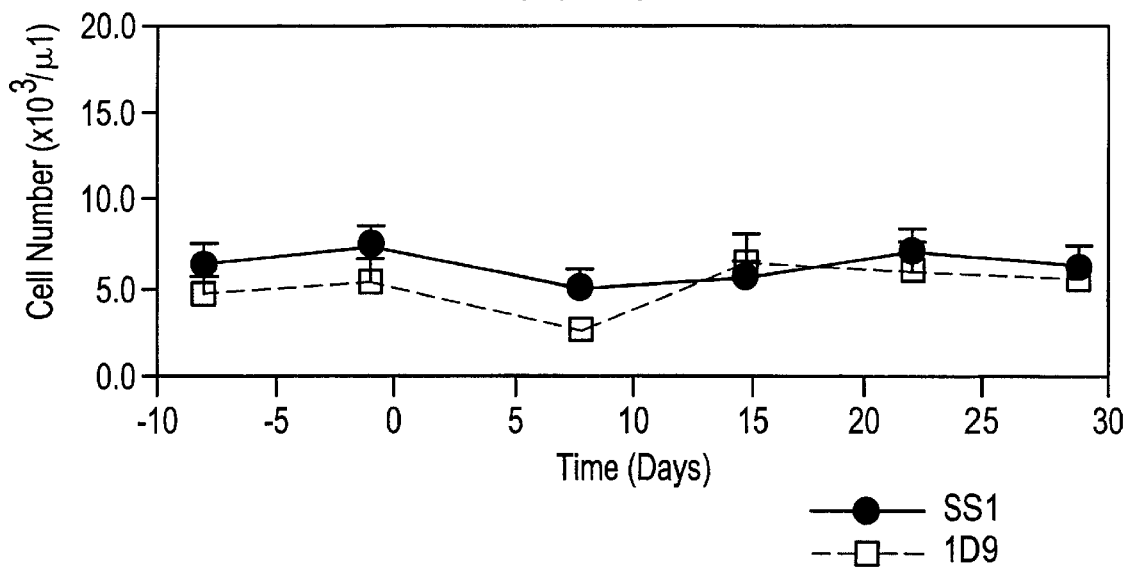
FIG. 3C is a graph showing the total lymphocyte cell count in the peripheral blood in animals treated with mAb S-S.1 or mAb 1D9 at predetermined time points.
Figure 3D:
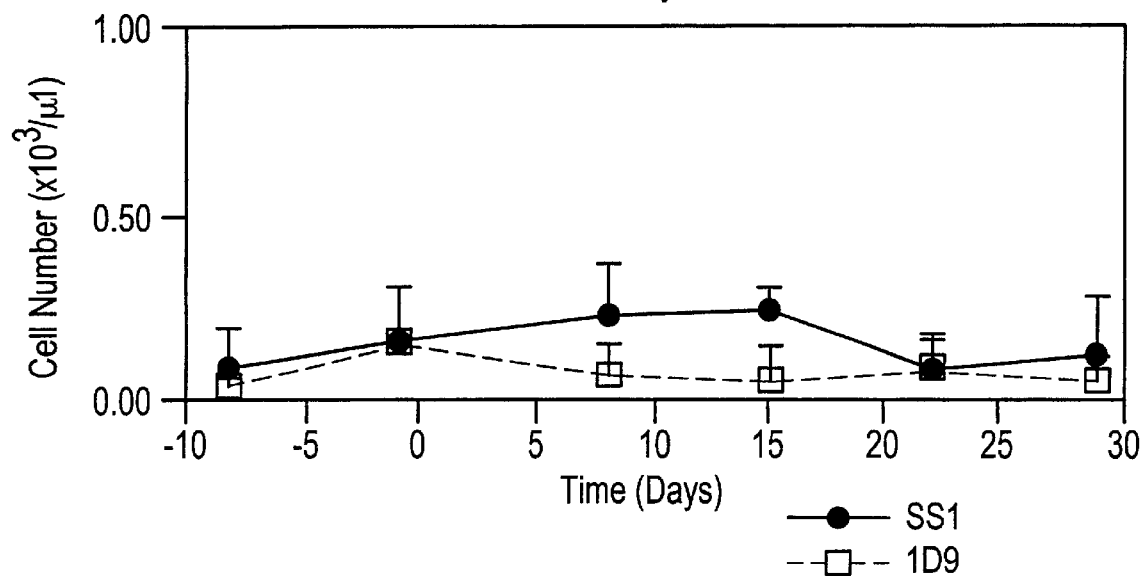
FIG. 3D is a graph showing the total monocyte cell count in the peripheral blood in animals treated with mAb S-S.1 or mAb 1D9 at predetermined time points.
Figure 3E:
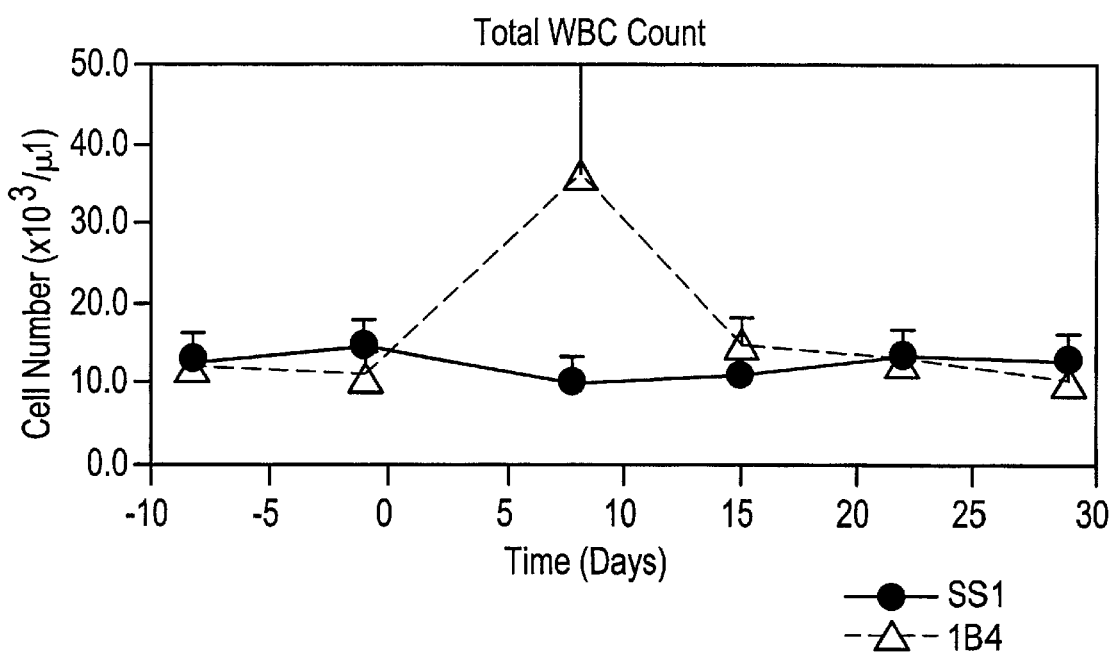
FIG. 3E is a graph showing the total white blood cell count in the peripheral blood in animals treated with mAb S-S.1 or mAb 1B4 at predetermined time points.
Figure 3H:
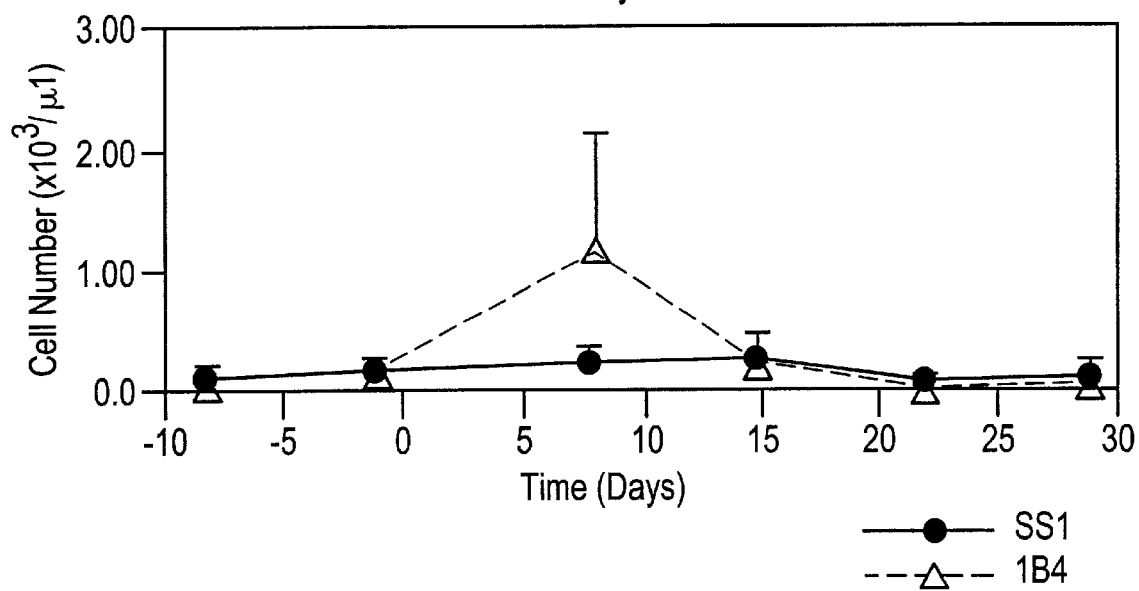
FIG. 3H is a graph showing the total monocyte cell count in the peripheral blood in animals treated with mAb S-S.1 or mAb 1B4 at predetermined time points.

The invention relates to a method of inhibiting stenosis or restenosis of a blood vessel following vascular injury, wherein the recruitment and/or adhesion of neutrophils and the adhesion and/or recruitment of mononuclear cells to a site of vascular injury is inhibited. As used herein "mononuclear cell" refers to monocytes, tissue macrophages and lymphocytes (e.g., T cells, B cells). Both neutrophils and mononuclear cells play a role in the pathophysiological response to vascular injury which leads to stenosis or restenosis. However, these cells participate to varying degrees in the process of vascular repair following different types of vascular injury, for example, balloon injury or "deep injury" produced by balloon angioplasty and placement of a stent.

As described herein a study in which the efficacy of murine mAb 1D9 or murine mAb 1B4 (also referred to as mAb 1B4) in a model of restenosis in Cynomolgus monkeys was conducted. Murine mAb 1D9 binds human and cynomolgus monkey CC-chemokine receptor 2 (CCR2) and inhibits the binding of ligand (e.g., MCP-1, MCP-2, MCP-3, MCP-4, MCP-5) to the receptor. CCR2 is expressed on mononuclear cells (monocytes, activated T cells) and limited amounts on basophils, but is not expressed on neutrophils. Murine mAb 1B4 binds human and cynomolgus monkey CD18, which is the common β chain component of members of the β2 integrin family (e.g., CD11a/CD18 (LFA-1, $\alpha_L\beta_2$), CD11b/CD18 (Mac-1, CR3, Mo1, $\alpha_M\beta_2$), CD11c/CD18 (p150,95, $\alpha_X\beta_2$), CD11d/CD18). Murine mAb 1B4 can inhibit the binding of ligands (e.g., ICAM-1) to β2 integrins, and thereby inhibit β2 integrin mediated cellular adhesion. CD18 is expressed primarily on neutrophils and to a lesser extent on mononuclear cells (monocytes and lymphocytes). Therefore, the study of mAb 1D9, which can inhibit the recruitment and/or activation of mononuclear cells to a site of vascular injury, and 1B4, which can inhibit the recruitment and/or adhesion of neutrophils to a site of vascular injury, in the model of restenosis provided an opportunity to distinguish the pathological contribution of neutrophils and mononuclear cells in vascular restenosis.

As described herein two types of vascular injury were produced in iliac arteries of cynomolgus monkeys by performing balloon angioplasty and deploying a stent in a portion of the area where the balloon was inflated. Thus, segments of the artery were injured by balloon only or by balloon plus stent. The results of the study revealed that administration of anti-CCR2 mAb 1D9 inhibited neointimal hyperplasia within the segments of iliac arteries injured by balloon plus stent, but not within the segment injured by balloon only. In contrast, administration of anti-CD18 mAb 1B4 inhibited neointimal hyperplasia within segments of iliac arteries injured by balloon plus stent and in segments injured by balloon alone. The results of the study indicate that mononuclear cells are important contributors to neointimal hyperplasia in response to injury by balloon plus stent but not by balloon alone, and that neutrophils provide an important (and perhaps predominant) contribution to neointimal hyperplasia in response to both types of injury.

The results of the study further indicate that simultaneous inhibition of neutrophil and mononuclear cell participation in the response to vascular injury or inhibition of neutrophil participation followed by inhibition of mononuclear cell participation can provide superior therapy for inhibiting stenosis or restenosis following vascular injury. For example, administration of an (i.e., one or more) agent which results in inhibition of recruitment and/or adhesion of neutrophils and mononuclear cells to a site of vascular injury can provide an efficacious method of inhibiting stenosis or restenosis (e.g., in-stent restenosis).

In one aspect, the invention is a method of inhibiting stenosis or restenosis following vascular injury comprising administering to a subject in need thereof an effective amount of a (i.e., one or more) suitable therapeutic agent which inhibits the recruitment and/or adhesion of neutrophils and mononuclear cells to a site of vascular injury.

Therapeutic Agents

Therapeutic agents which are suitable for administration in accordance with the therapeutic methods described herein can inhibit the recruitment and/or adhesion of neutrophils and/or mononuclear cells to a site of vascular injury. Suitable therapeutic agents can, for example, inhibit the activity (e.g., binding activity, signaling activity) of a cell surface molecule through which cellular adhesion, chemotaxis and/or homing are mediated. For example, antagonists of cellular adhesion molecules (e.g., integrins (e.g., β1, β2, β3, β4, β5, β6, β7, β8 integrins), selectins (e.g., E-selectin, P-selectin, L-selectin), cadherins (e.g., E-, P-, N-cadherins) and immunoglobulin superfamily adhesion molecules (e.g., LFA-2, LFA-3, CD44)) and antagonists of cytokine receptors (e.g., antagonists of chemokine receptor function) can be used. In addition, agents which bind to ligands of cellular adhesion molecules or cytokines or chemokines and inhibit the binding of ligand to receptors expressed on neutrophils and/or mononuclear cells can be used.

As used herein, the term "cellular adhesion molecule antagonist" refers to an agent (e.g., a molecule, a compound)

which can inhibit a function of a cellular adhesion molecule (e.g., a β2 integrin). For example, an antagonist of the β2 integrin CD11b/CD18 (Mac-1) can inhibit the binding of one or more ligands (e.g., ICAM-1, fibrinogen, C3bi) to the integrin. Accordingly, cellular adhesion mediated by integrin-ligand interactions can be inhibited.

As used herein, the term "antagonist of chemokine receptor function" refers to an agent (e.g., a molecule, a compound) which can inhibit a (i.e., one or more) function of a chemokine receptor (e.g., CC-chemokine receptor (e.g., CC-chemokine receptor 1 (CCR1), CCR2, CCR3, CCR4, CCR5, CCR6, CCR7, CCR8, CCR9), CXC-chemokine receptor (e.g., CXC-chemokine receptor 1 (IL-8R-1), CXCR2 (IL-8R-2), CXCR3, CXCR4), CX3C-chemokine receptor (e.g., CX3CR1)). For example, an antagonist of CC-chemokine receptor 2 (CCR2) function can inhibit the binding of one or more ligands (e.g., MCP-1, MCP-2, MCP-3, MCP-4, MCP-5) to CCR2 and/or inhibit signal transduction mediated through CCR2 (e.g., GDP/GTP exchange by CCR2 associated G proteins, intracellular calcium flux). Accordingly, CCR2-mediated processes and cellular responses (e.g., proliferation, migration, chemotactic responses, secretion or degranulation) can be inhibited with an antagonist of CCR2 function. Preferred chemokine receptor antagonists for administration in accordance with the method of the invention can inhibit one or more functions of CCR2. As used herein, "CC-chemokine receptor 2" ("CCR2") refers to CC-chemokine receptor 2a and/or CC-chemokine receptor 2b.

Preferably, the agent to be administered (e.g., cellular adhesion molecule antagonist, antagonist of chemokine receptor function) is a compound which is, for example, a small organic molecule, natural product, protein (e.g., antibody, chemokine, cytokine), peptide or peptidomimetic. Several types of molecules that can be used to antagonize one or more functions of chemokine receptors or cell adhesion molecules (e.g., integrins) are known in the art, including small organic molecules, proteins, such as antibodies (e.g., polyclonal sera, monoclonal, chimeric, humanized, human) and antigen-binding fragments thereof (e.g., Fab, Fab', F(ab')$_2$, Fv); and peptides.

Agents which can inhibit the recruitment and/or adhesion of neutrophils and/or mononuclear cells to a site of vascular injury can be identified, for example, by screening libraries or collections of molecules, such as, the Chemical Repository of the National Cancer Institute, as described herein or using other suitable methods. Agents thus identified can be used in the therapeutic methods described herein.

Another source of agents which can inhibit the recruitment and/or adhesion of neutrophils and/or mononuclear cells to a site of vascular injury (e.g., cellular adhesion molecule antagonist, antagonist of chemokine receptor function) are combinatorial libraries which can comprise many structurally distinct molecular species. Combinatorial libraries can be used to identify lead compounds or to optimize a previously identified lead. Such libraries can be manufactured by well-known methods of combinatorial chemistry and screened by suitable methods, such as the methods described herein.

The term "natural product", as used herein, refers to a compound which can be found in nature, for example, naturally occurring metabolites of marine organisms (e.g., tunicates, algae), plants or other organisms which possess biological activity, e.g., can antagonize chemokine receptor function. For example, lactacystin, paclitaxel and cyclosporin A are natural products which can be used as anti-proliferative or immunosuppressive agents.

Natural products can be isolated and identified using suitable methods. For example, a suitable biological source (e.g., vegetation) can be homogenized (e.g., by grinding) in a suitable buffer and clarified by centrifugation, thereby producing an extract. The resulting extract can be assayed for biological activity, such as the capacity to antagonize a cellular adhesion molecule or a chemokine receptor using, for example, the assays described herein. Extracts which contain a desired activity can be further processed to isolate active agent (e.g., cellular adhesion molecule antagonist, antagonist of chemokine receptor function) using suitable methods, such as, fractionation (e.g., column chromatography (e.g., ion exchange, reverse phase, affinity), phase partitioning, fractional crystallization) and assaying for biological activity (e.g., antagonism of CCR2 activity). Once isolated the structure of a natural product can be determined (e.g., by nuclear magnetic resonance (NMR)) and those of skill in the art can devise a synthetic scheme for synthesizing the natural product. Thus, a natural product can be isolated (e.g., substantially purified) from nature or can be fully or partially synthetic. A natural product can be modified (e.g., derivatized) to optimize its therapeutic potential. Thus, the term "natural product", as used herein, includes those compounds which are produced using standard medicinal chemistry techniques to optimize the therapeutic potential of a compound which can be isolated from nature.

The term "peptide", as used herein, refers to a compound consisting of from about two to about ninety amino acid residues wherein the amino group of one amino acid is linked to the carboxyl group of another amino acid by a peptide bond. A peptide can be, for example, derived or removed from a native protein by enzymatic or chemical cleavage, or can be prepared using conventional peptide synthesis techniques (e.g., solid phase synthesis) or molecular biology techniques (see Sambrook, J. et al., Molecular Cloning: A Laboratory Manual, Cold Spring Harbor Press, Cold Spring Harbor, N.Y. (1989)). A "peptide" can comprise any suitable L- and/or D-amino acid, for example, common α-amino acids (e.g., alanine, glycine, valine), non-α-amino acids (e.g., β-alanine, 4-aminobutyric acid, 6-aminocaproic acid, sarcosine, statine), and unusual amino acids (e.g., citrulline, homocitruline, homoserine, norleucine, norvaline, ornithine). The amino, carboxyl and/or other functional groups on a peptide can be free (e.g., unmodified) or protected with a suitable protecting group. Suitable protecting groups for amino and carboxyl groups, and methods for adding or removing protecting groups are known in the art and are disclosed in, for example, Green and Wuts, "*Protecting Groups in Organic Synthesis*", John Wiley and Sons, 1991. The functional groups of a peptide can also be derivatized (e.g., alkylated) using art-known methods.

Peptides can be synthesized and assembled into libraries comprising a few to many discrete molecular species. Such libraries can be prepared using well-known methods of combinatorial chemistry, and can be screened as described herein or using other suitable methods to determine if the library comprises peptides with a desired biological activity (e.g., cellular adhesion molecule antagonist, antagonist of chemokine receptor function). Such peptide antagonists can then be isolated using suitable methods.

The term "peptidomimetic", as used herein, refers to molecules which are not polypeptides, but which mimic aspects of their structures. For example, polysaccharides can be prepared that have the same functional groups as peptides. Peptidomimetics can be designed, for example, by establishing the three dimensional structure of a peptide agent in the environment in which it is bound or will bind to a target molecule (e.g., cellular adhesion molecule, chemokine receptor). The peptidomimetic comprises at least two components, the binding moiety or moieties and the backbone or supporting structure.

The binding moieties are the chemical atoms or groups which will react or form a complex (e.g., through hydrophobic or ionic interactions) with a target molecule (e.g., cellular adhesion molecule, chemokine receptor), for example, with the amino acid(s) at or near the ligand binding site. For example, the binding moieties in a peptidomimetic can be the same as those in a peptide antagonist of a cellular adhesion molecule (e.g., an integrin) or chemokine receptor. The binding moieties can be an atom or chemical group which reacts with the receptor in the same or similar manner as the binding moiety in the peptide antagonist. For example, when it is desirable to inhibit integrin-mediated adhesion a peptidomimetic which resembles an RGD-containing peptide can be prepared. Examples of binding moieties suitable for use in designing a peptidomimetic for a basic amino acid in a peptide are nitrogen containing groups, such as amines, ammoniums, guanidines and amides or phosphoniums. Examples of binding moieties suitable for use in designing a peptidomimetic for an acidic amino acid can be, for example, carboxyl, lower alkyl carboxylic acid ester, sulfonic acid, a lower alkyl sulfonic acid ester or a phosphorous acid or ester thereof.

The supporting structure is the chemical entity that, when bound to the binding moiety or moieties, provides the three dimensional configuration of the peptidomimetic. The supporting structure can be organic or inorganic. Examples of organic supporting structures include polysaccharides, polymers or oligomers of organic synthetic polymers (such as, polyvinyl alcohol or polylactide). It is preferred that the supporting structure possess substantially the same size and dimensions as the peptide backbone or supporting structure. This can be determined by calculating or measuring the size of the atoms and bonds of the peptide and peptidomimetic. In one embodiment, the nitrogen of the peptide bond can be substituted with oxygen or sulfur, thereby forming a polyester backbone. In another embodiment, the carbonyl can be substituted with a sulfonyl group or sulfinyl group, thereby forming a polyamide (e.g., a polysulfonamide). Reverse amides of the peptide can be made (e.g., substituting one or more —CONH— groups for a —NHCO— group). In yet another embodiment, the peptide backbone can be substituted with a polysilane backbone.

These compounds can be manufactured by known methods. For example, a polyester peptidomimetic can be prepared by substituting a hydroxyl group for the corresponding α-amino group on amino acids, thereby preparing a hydroxyacid and sequentially esterifying the hydroxyacids, optionally blocking the basic and acidic side chains to minimize side reactions. Determining an appropriate chemical synthesis route can generally be readily identified upon determining the chemical structure.

Peptidomimetics can be synthesized and assembled into libraries comprising a few to many discrete molecular species. Such libraries can be prepared using well-known methods of combinatorial chemistry, and can be screened as described herein to determine if the library comprises one or more peptidomimetics which antagonize a cellular adhesion molecule or a chemokine receptor, for example. Such peptidomimetic antagonists can then be isolated by suitable methods.

In one embodiment, the agent (e.g., antagonist of chemokine function, cell adhesion molecule antagonists) is an antibody or antigen-binding fragment thereof. In certain embodiments, the antibody or antigen binding fragment can have binding specificity for an integrin (e.g., a β2 integrin (e.g., CD11a/CD18 (LFA-1, $\alpha_L\beta_2$), CD11b/CD18 (Mac-1, CR3, Mo1, $\alpha_M\beta_2$), CD11c/CD18 (p150,95, $\alpha_X\beta_2$), CD11d/CD18) or a chemokine receptor (e.g., CCR2). The antibody can be polyclonal or monoclonal, and the term "antibody" is intended to encompass both polyclonal and monoclonal antibodies. The terms polyclonal and monoclonal refer to the degree of homogeneity of an antibody preparation, and are not intended to be limited to particular methods of production. The term "antibody" as used herein also encompasses functional fragments of antibodies, including fragments of human, chimeric, humanized, primatized, veneered or single chain antibodies. Functional fragments include antigen-binding fragments which bind to a β2 integrin or chemokine receptor, for example. For example, antibody fragments capable of binding to CCR2 or portions thereof, including, but not limited to Fv, Fab, Fab' and F(ab')$_2$ fragments can be administered in accordance with the therapeutic methods of the invention. Such fragments can be produced by enzymatic cleavage or by recombinant techniques. For example, papain or pepsin cleavage can generate Fab or F(ab')$_2$ fragments, respectively. Other proteases with the requisite substrate specificity can also be used to generate Fab or F(ab')$_2$ fragments. Antibodies can also be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the CH$_1$ domain and hinge region of the heavy chain. Single chain antibodies, and human, chimeric, humanized or primatized (CDR-grafted), or veneered antibodies, as well as chimeric, CDR-grafted or veneered single chain antibodies, comprising portions derived from different species, and the like are also encompassed by the present invention and the term "antibody". The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0 451 216 B1; and Padlan, E. A. et al., EP 0 519 596 A1. See also, Newman, R. et al., *BioTechnology*, 10: 1455–1460 (1992), regarding primatized antibody, and Ladner et al., U.S. Pat. No. 4,946,778 and Bird, R. E. et al., *Science*, 242: 423–426 (1988)) regarding single chain antibodies.

Humanized antibodies can be produced using synthetic or recombinant DNA technology using standard methods or other suitable techniques. Nucleic acid (e.g., cDNA) sequences coding for humanized variable regions can also be constructed using PCR mutagenesis methods to alter DNA sequences encoding a human or humanized chain, such as a DNA template from a previously humanized variable region (see e.g., Kamman, M., et al., *Nucl. Acids Res.*, 17: 5404 (1989)); Sato, K., et al., *Cancer Research*, 53: 851–856 (1993); Daugherty, B. L. et al., *Nucleic Acids Res.*, 19(9): 2471–2476 (1991); and Lewis, A. P. and J. S. Crowe, *Gene*, 101: 297–302 (1991)). Using these or other suitable methods, variants can also be readily produced. In one embodiment, cloned variable regions can be mutated, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993). As used herein, an antigen-binding fragment of a humanized immunoglobulin heavy or light chain is intended to mean a fragment which binds to an antigen when paired with a complementary chain. That is, an antigen-binding fragment of a humanized light chain will bind to an antigen when paired with a heavy chain (e.g., murine, chimeric, humanized) comprising a variable region, and an antigen-binding fragment of a humanized heavy chain will bind to an antigen when paired with a light chain (e.g., murine, chimeric, humanized) comprising a variable region.

Antibodies (e.g., human, humanized and chimeric antibodies) can comprise a constant region (e.g., a human constant region) derived from the κ or λ light chains, and/or the γ (e.g., γ1, γ2, γ3, γ4), μ, α (e.g., α1, α2), δ or ε heavy chains of human antibodies, including allelic variants. A particular constant region (e.g., IgG1), variant or portions thereof can be selected in order to tailor effector function. For example, an mutated constant region (variant) can be incorporated into a fusion protein to minimize binding to Fc receptors and/or ability to fix complement (see e.g., see e.g., Winter et al., WO 88/07089 (published Sep. 22, 1988), GB 2,209,757 B, U.S. Pat. No. 5,624,821, and U.S. Pat. No. 5,648,260; Morrison et al, WO 89/07142; Morgan et al., WO 94/29351 (published Dec. 22, 1994)).

Antibodies which specifically bind to a desired mammalian (e.g., human) protein (e.g., cell adhesion protein, chemokine receptor) can be raised against an appropriate immunogen, such as isolated and/or recombinant human CCR2 or portions thereof (including synthetic molecules, such as synthetic peptides). Antibodies which specifically bind a desired protein can also be raised by immunizing a suitable host (e.g., mouse) with cells that naturally expresses said protein. (see e.g., U.S. Pat. No. 5,440,020, the entire teachings of which are incorporated herein by reference). In addition, cells expressing recombinant protein such as transfected cells, can be used as immunogens or in a screen for antibody which binds said protein (See e.g., Chuntharapai et al., *J. Immunol.*, 152: 1783–1789 (1994); Chuntharapai et al., U.S. Pat. No. 5,440,021).

Preparation of immunizing antigen, and polyclonal and monoclonal antibody production can be performed using any suitable technique. A variety of methods have been described (see e.g., Kohler et al., *Nature*, 256: 495–497 (1975) and *Eur. J. Immunol.* 6: 511–519 (1976); Milstein et al., *Nature* 266: 550–552 (1977); Koprowski et al., U.S. Pat. No. 4,172,124; Harlow, E. and D. Lane, 1988, *Antibodies: A Laboratory Manual*, (Cold Spring Harbor Laboratory: Cold Spring Harbor, N.Y.); *Current Protocols In Molecular Biology*, Vol. 2 (Supplement 27, Summer '94), Ausubel, F. M. et al., Eds., (John Wiley & Sons: New York, N.Y.), Chapter 11, (1991)). When monoclonal antibodies are desired, a hybridoma is generally produced by fusing a suitable immortal cell line (e.g., a myeloma cell line such as SP2/0 or P3X63Ag8.653) with antibody producing cells. The antibody producing cells, preferably those obtained from the spleen or lymph nodes, can be obtained from animals immunized with the antigen of interest. The fused cells (hybridomas) can be isolated using selective culture conditions, and cloned by limiting dilution. Cells which produce antibodies with the desired specificity can be selected by a suitable assay (e.g., ELISA).

Other suitable methods of producing or isolating antibodies of the requisite specificity can be used, including, for example, methods which select recombinant antibody from a library (e.g., a phage display library). Transgenic animals capable of producing a repertoire of human antibodies (e.g., Xenomouse® (Abgenix, Fremont, Calif.)) can be produced using suitable methods (see e.g., Jakobovits et al., *Proc. Natl. Acad. Sci. USA*, 90: 2551–2555 (1993); Jakobovits et al., *Nature*, 362: 255–258 (1993); Lonberg et al., U.S. Pat. No. 5,545,806; Surani et al., U.S. Pat. No. 5,545,807; Lonberg et al., WO97/13852).

In a preferred embodiment, the antibody or antigen-binding fragment thereof has specificity for a mammalian CD18 (e.g., human CD18), the common β chain of the β2 integrins, and can inhibit cellular adhesion mediated through binding of a ligand (i.e., one or more ligands (e.g., ICAM-1, ICAM-2, fibrinogen)) to a β2 integrin. Antibodies which bind CD18 and inhibit CD18-mediated cellular adhesion include, for example, humanized mAb 1B4 (also referred to as humanized mAb 1B4) (EP 0 438 312 A2), mAb 60.3 (Kling, D. et al., *Arterioscler. Thromb.* 12:997–1007 (1992)), mAb R15.7 (Guszman, L. A., et al. *Coronary Artery Dis.*, 6:693–701 (1995); Golino, P. et al. *Thromb. Haemost.*, 77:783–788 (1997)), rat mAb YFC51.1, LDP-01 a humanized YFC51.1 (U.S. Pat. Nos. 5,985,279 and 5,997,867, the entire teachings of each of the preceding U.S. patents are incorporated herein by reference). Other antibodies which can be administered in accordance with the invention include antibodies which bind to Mac-1 and inhibit Mac-1 mediated cellular adhesion, for example mAb M1/70 (Rogers, C. et al., *Proc. Natl. Acad. Sci., U.S.A.*, 95:10134–10139 (1998)) and mAb 7E3 or c7E3 Fab (Simon, D. I. et al., *Arterioscler Thromb Vasc Biol.*, 17:528–535 (1997)).

Other preferred antibodies bind mammalian CCR2 (e.g., human CCR2) and inhibit the binding of a ligand (e.g., MCP-1, MCP-2, MCP-3, MCP-4, MCP-5) to the receptor. Murine monoclonal antibodies designated 1D9 (also referred to as LS132.1D9 or 1D9-2-121-3-6) and 8G2 (also referred to as LS132.8G2), which bind CCR2 and inhibit the binding of ligand to the receptor, were produced as described herein. Hybridoma cell lines producing the antibodies were deposited on Jul. 17, 1998, on behalf of LeukoSite, Inc., 215 First Street, Cambridge, Mass. 02142, U.S.A., (now Millennium Pharmaceuticals, Inc., 75 Sidney Street, Cambridge, Mass. 02139, U.S.A.) at the American Type Culture Collection, 10801 University Boulevard, Manassas, Va. 20110, U.S.A., under Accession Nos. HB-12549 (1D9) and HB-12550 (8G2). These antibodies and, for example, chimeric or humanized version of the antibodies can be administered in accordance with the method of the invention. An antibody which binds CCR2 and inhibits the binding of a ligand (e.g., MCP-1, MCP-2, MCP-3, MCP-4, MCP-5) to the receptor can comprise a humanized 1D9 light chain comprising an amino acid sequence selected from the group consisting of SEQ ID NO: 14, SEQ ID NO: 15, SEQ ID NO: 16, SEQ ID NO: 17 and SEQ ID NO: 18, and/or a humanized 1D9 heavy chain comprising an amino acid sequence selected from the group consisting of SEQ ID NO: 20, SEQ ID NO: 21, SEQ ID NO: 22, and SEQ ID NO: 23. In certain embodiments, an antibody which binds CCR2 and inhibits the binding of a ligand to the receptor can comprise a humanized chain (e.g., a humanized 1D9 light chain comprising an amino acid sequence selected from the group consisting of SEQ ID NO: 14, SEQ ID NO: 15, SEQ ID NO: 16, SEQ ID NO: 17 and SEQ ID NO: 18, or a humanized 1D9 heavy chain comprising an amino acid sequence selected from the group consisting of SEQ ID NO: 20, SEQ ID NO: 21, SEQ ID NO: 22, and SEQ ID NO: 23) and a complementary chain (heavy or light as appropriate) which is, for example, human, nonhuman (e.g., rodent (e.g., murine), primate) humanized or chimeric. A complementary light or heavy chain is one which is capable of associating with a selected heavy or light chain, respectively, resulting in an antibody or antigen-binding fragment which binds CCR2 and inhibits the binding of a ligand (e.g., MCP-1, MCP-2, MCP-3, MCP-4, MCP-5) to the receptor. Antigen-binding fragments of such antibodies (e.g., Fab fragments, F(ab')$_2$ fragments, Fab' fragments, Fv fragments) can also be administered in accordance with the method of the invention.

In certain embodiments, a humanized antibody which binds CCR2 and inhibits the binding of a ligand (e.g., MCP-1, MCP-2, MCP-3, MCP-4, MCP-5) to the receptor is administered. In particular embodiments, the humanized antibody can comprise a light chain comprising the amino acid sequence of SEQ ID NO: 14 and a heavy chain comprising an amino acid sequence selected from the group consisting of SEQ ID NO: 20, SEQ ID NO: 21, SEQ ID NO: 22 and SEQ ID NO: 23. In other embodiments, the humanized antibody can comprise a light chain comprising the amino acid sequence of SEQ ID NO: 15 and a heavy chain comprising an amino acid sequence selected from the group consisting of SEQ ID NO: 20, SEQ ID NO: 21, SEQ ID NO: 22 and SEQ ID NO: 23. In other embodiments, the humanized antibody which binds CCR2 and inhibits the binding of a ligand to the receptor can comprise a light chain comprising the amino acid sequence of SEQ ID NO: 16 and a heavy chain comprising an amino acid sequence selected from the group consisting of SEQ ID NO: 20, SEQ ID NO: 21, SEQ ID NO: 22 and SEQ ID NO: 23. In other embodiments, the humanized antibody can comprise a light chain comprising the amino acid sequence of SEQ ID NO: 17 and a heavy chain comprising an amino acid sequence selected from the group consisting of SEQ ID NO: 20, SEQ ID NO: 21, SEQ ID NO: 22 and SEQ ID NO: 23. In further embodiments, the humanized antibody can comprise a light chain comprising the amino acid sequence of SEQ ID NO: 18 and a heavy chain comprising an amino acid sequence selected from the group consisting of SEQ ID NO: 20, SEQ ID NO: 21, SEQ ID NO: 22 and SEQ ID NO: 23.

In additional embodiments, the humanized antibody which binds CCR2 and inhibits the binding of a ligand (e.g., MCP-1, MCP-2, MCP-3, MCP-4, MCP-5) to the receptor can comprise a heavy chain comprising the amino acid sequence of SEQ ID NO: 20 and a light chain comprising an amino acid sequence selected from the group consisting of SEQ ID NO: 14, SEQ ID NO: 15, SEQ ID NO: 16, SEQ ID NO: 17 and SEQ ID NO: 18. In other embodiments, the humanized antibody can comprise a heavy chain comprising the amino acid sequence of SEQ ID NO: 21 and a light chain comprising an amino acid sequence selected from the group consisting of SEQ ID NO: 14, SEQ ID NO: 15, SEQ ID NO: 16, SEQ ID NO: 17 and SEQ ID NO: 18. In other embodiments, the humanized antibody can comprise a heavy chain comprising the amino acid sequence of SEQ ID NO: 22 and a light chain comprising an amino acid sequence selected from the group consisting of SEQ ID NO: 14, SEQ ID NO: 15, SEQ ID NO: 16, SEQ ID NO: 17 and SEQ ID NO: 18. In further embodiments, the humanized antibody which binds CCR2 and inhibits the binding of a ligand (e.g., MCP-1, MCP-2, MCP-3, MCP-4, MCP-5) to the receptor can comprise a heavy chain comprising the amino acid sequence of SEQ ID NO: 23 and a light chain comprising an amino acid sequence selected from the group consisting of SEQ ID NO: 14, SEQ ID NO: 15, SEQ ID NO: 16, SEQ ID NO: 17 and SEQ ID NO: 18.

In additional embodiments, the antibody which binds CCR2 and inhibits the binding of a ligand (e.g., MCP-1, MCP-2, MCP-3, MCP-4, MCP-5) to the receptor can comprise a light chain comprising the variable region of murine antibody 1D9 (SEQ ID NO:11) and a complementary heavy chain, for example, a heavy chain comprising a variable region having an amino acid sequence selected from the group consisting of SEQ ID NO: 20, SEQ ID NO: 21, SEQ ID NO: 22 and SEQ ID NO: 23. In further embodiments, the antibody which binds CCR2 and inhibits the binding of a ligand (e.g., MCP-1, MCP-2, MCP-3, MCP-4, MCP-5) to the receptor can comprise a heavy chain comprising the variable region of murine antibody 1D9 (SEQ ID NO: 12) and a complementary light chain, for example, a light chain comprising a variable region having an amino acid sequence selected from the group consisting of SEQ ID NO: 14, SEQ ID NO: 15, SEQ ID NO: 16, SEQ ID NO: 17 and SEQ ID NO: 18.

A preferred antibody or antigen-binding fragment thereof that can be administered to inhibit stenosis or restenosis in accordance with the invention can be a humanized 1D9 antibody or antigen binding fragment thereof, comprising a light chain comprising the amino acid sequence of SEQ ID NO: 14 and a heavy chain comprising the amino acid sequence of SEQ ID NO: 20.

Additional antibodies including human, humanized and chimeric antibodies and the like, having binding specificity for a cellular adhesion molecule (e.g., integrin (e.g., CD18), selectin, cadherin, immunoglobulin adhesion molecule) or chemokine receptor (e.g., CCR2) can be prepared using the methods described herein or other suitable methods.

Assessment of Activity of Agents

The activity of agents (e.g., cell adhesion molecule antagonists, chemokine receptor antagonists) can be assessed using any suitable assay. For example, antagonists of chemokine receptor function can be identified in a suitable binding or chemotaxis assay. In one example, antagonists of CCR2 function can be identified in a competitive binding assay where a reduction in the binding of a ligand of CCR2 (in the presence of an agent (e.g., antibody)), as compared to binding of the ligand in the absence of the agent, is detected or measured. A composition comprising an isolated and/or recombinant mammalian CCR2 or functional variant thereof can be contacted with the ligand and agent simultaneously, or one after the other, in either order. A reduction in the extent of binding of the ligand in the presence of the antibody, is indicative of inhibition of binding by the antibody. For example, binding of the ligand could be decreased or abolished.

Direct inhibition of the binding of a ligand (e.g., a chemokine such as MCP-1) to a mammalian CCR2 or ligand-binding variant thereof by an agent (e.g., antibody) can be monitored. For example, the ability of an agent to inhibit the binding of $^{125}$I-labeled MCP-1, $^{125}$I-labeled MCP-2, $^{125}$I-labeled MCP-3 or $^{125}$I-labeled MCP-4 to mammalian CCR2 can be monitored. Such an assay can be conducted using suitable cells bearing CCR2 or a ligand-binding variant thereof, such as isolated blood cells (e.g., T cells, PBMC) or a suitable cell line naturally expressing CCR2, or a cell line containing nucleic acid encoding a mammalian CCR2 (e.g., a cell line expressing recombinant CCR2), or a membrane fraction from said cells, for instance.

Other methods of identifying antagonists of CCR2 function are available, such as other suitable binding assays, or methods which monitor events which are triggered upon binding of ligand to receptor, including signaling function and/or stimulation of a cellular response (e.g., leukocyte trafficking, leukocyte chemotaxis). It will be understood that the agents which inhibit other cytokine receptors (e.g., other chemokine receptors), can be identified by suitable modification of the described assays. For example, agents which antagonize CC-chemokine receptor 1 (CCR1) can be identified in assays using a composition comprising CCR1 such as THP-1 cell membranes and a labeled CCR1 ligand (e.g., RANTES).

Cell adhesion molecule antagonists can be identified using a suitable binding assay. For example, cellular adherence can be monitored by methods known in the art or other suitable methods. In one suitable assay, an agent to be tested can be combined with (a) non adherent cells which express a cellular adhesion molecule (e.g., an integrin), and (b) a composition comprising a ligand (e.g., a substrate such as a culture well coated with a ligand, a culture well containing adherent cells which express a ligand of the cellular adhesion molecule), and maintained under conditions suitable for ligand-receptor mediated adhesion. Labeling of cells with a fluorescent dye provides a convenient means of detecting adherent cells. Nonadherent cells can be removed (e.g., by washing) and the number of adherent cells determined. A reduction in the number of adherent cells in wells containing a test agent (e.g., antibody) in comparison to suitable control wells (e.g., wells that do not contain a test agent) indicates that the agent is an antagonist of the cellular adhesion molecule.

Therapeutic Methods

The invention provides a method of inhibiting (e.g., reducing the severity of or preventing) stenosis or restenosis following a vascular injury in a subject, such as a human. The injury can occur during and/or be caused by a diagnostic or therapeutic vascular intervention procedure, such as, angiography, angioplasty (e.g., performed by balloon, atherectomy, laser angioplasty or other suitable methods (with or without rotablation and/or stent placement)), endarterectomy, coronary artery by-pass surgery, stent placement (e.g., endovascular stent, coronary stent), and/or other vascular intervention procedures (e.g., vascular surgery, vascular graft, deployment of a peripheral stent, insertion of a prosthetic valve or vessel (e.g., in autologous, non-autologous or synthetic vessel graft), transplantation of organs, tissues or cells, intravascular brachytherapy). In a particular aspect, the method can be used to inhibit stenosis or restenosis following a coronary artery intervention procedure, such as percutaneous transluminal coronary angioplasty (PTCA), or a vascular intervention procedure which includes placement of a stent (e.g., PTCA plus endovascular stent placement).

In one aspect, the method of inhibiting stenosis or restenosis following a vascular injury comprises administering to a subject in need thereof an effective amount of an (i.e., one or more) agent which inhibits the recruitment and/or adhesion of neutrophils or mononuclear cells to a site of vascular injury. The method includes therapeutic or prophylactic treatment. According to the method, the stenosis or restenosis can be prevented or reduced (inhibited) in whole or in part.

In one embodiment, a single agent which inhibits the recruitment and/or adhesion of neutrophils or mononuclear cells to a site of vascular injury is administered. The agent can be, for example, an antibody which binds to a cellular adhesion molecule and thereby prevents adhesion of neutrophils and mononuclear cells to a site of vascular injury. In particular embodiments, the agent is an antibody which binds to an integrin (e.g., β2 integrin) and inhibits integrin mediated adhesion. In other embodiments, the agent is an antibody which binds to a chemokine receptor (e.g., CCR2) and inhibits binding of ligand (e.g., MCP-1, MCP-2, MCP-3, MCP-4, MCP-5) to the receptor, thereby inhibiting recruitment and/or adhesion of neutrophils and mononuclear cells to a site of vascular injury.

In a preferred aspect, the method of inhibiting stenosis or restenosis following vascular injury in a subject in need thereof, comprises administering to the subject a first agent which inhibits the adhesion and/or recruitment of neutrophils to a site of vascular injury, and a second agent which inhibits adhesion and/or recruitment of mononuclear cells to a site of vascular injury. In certain embodiments, the first agent is a cellular adhesion molecule antagonist. In particular embodiments, the first agent can inhibit integrin-mediated adhesion of neutrophils to a site of vascular injury. In more particular embodiments, the first agent can inhibit β2 integrin-mediated neutrophil adhesion to a site vascular injury. For example, the first agent can inhibit neutrophil adhesion mediated by CD11a/CD18 (LFA-1, $\alpha_L\beta_2$), CD11b/CD18 (Mac-1, CR3, Mo1, $\alpha_M\beta_2$), CD11c/CD18 (p150,95, $\alpha_X\beta_2$) and/or CD11d/CD18. In a preferred embodiment the first agent is an antibody which binds CD18 and thereby inhibits β2-integrin-mediated adhesion of neutrophils to a site of vascular injury. Preferred anti-CD18 antibodies for administration to humans include humanized YFC51.1 antibodies (see U.S. Pat. Nos. 5,985,279 and 5,997,867), such as LDP-01 (humanized YFC51.1 which comprises a human γ1 heavy chain constant region having two mutations (Leu$^{235}$→Ala$^{235}$ and Gly$^{137}$→Ala$^{237}$) which reduce binding to Fcγ receptors).

The second agent administered in accordance with the method can be a cell adhesion molecule antagonist, such as a peptide, small molecule or antibody which inhibits the adhesion of mononuclear cells to sites of vascular injury. The second agent can also be an antagonist of chemokine receptor function. In certain embodiments, the second agent is an antagonist of a CC-chemokine receptor. In particular embodiments, the second agent is an antagonist of CC-chemokine receptor 2 (CCR2). Preferred antagonists of chemokine receptor function include small organic molecules and antibodies or antigen-binding fragments thereof that bind CCR2 and inhibit the binding of a ligand (e.g., MCP-1, MCP-2, MCP-3, MCP-4, MCP-5) to the receptor. The murine monoclonal antibodies designated 1D9 and 8G2, and humanized, human or chimeric antibodies which have the same or similar epitopic specificity as mAb 1D9 or mAb 8G2 or which bind to human CCR2 and inhibit the binding of a ligand to the receptor are particularly preferred.

The methods described herein can also be used to treat a subject having an inflammatory disease or condition mediated by early neutrophil activity and later mononuclear cell activity. For example the methods described herein can be used to treat a subject having mastitis (mammary gland), vaginitis, cholecystitis, cholangitis or pericholangitis (bile duct and surrounding tissue of the liver), chronic bronchitis, chronic sinusitis, asthma, and graft versus host disease (e.g., in the gastrointestinal tract). Chronic inflammatory diseases of the lung which result in interstitial fibrosis, such as interstitial lung diseases (ILD) (e.g., chronic obstructive pulmonary disease, idiopathic pulmonary fibrosis, or ILD associated with rheumatoid arthritis, or other autoimmune conditions), hypersensitivity pneumonitis, collagen diseases, sarcoidosis, and other idiopathic conditions can be amenable to treatment. Pancreatitis and insulin-dependent diabetes mellitus are other diseases which can be treated using the present method.

The methods of the invention can also be used to treat inflammatory bowel disease (IBD), such as ulcerative colitis, Crohn's disease, ileitis, Celiac disease, nontropical Sprue, enteritis, enteropathy associated with seronegative arthropathies, microscopic or collagenous colitis, eosinophilic gastroenteritis, or pouchitis resulting after proctocolectomy, and ileoanal anastomosis.

Additional diseases or conditions, including chronic diseases, of humans or other species which can be treated in accordance with the method of the invention, include, but are not limited to:

inflammatory or allergic diseases and conditions, including systemic anaphylaxis or hypersensitivity responses, drug allergies (e.g., to penicillin, cephalosporins), insect sting allergies; psoriasis and inflammatory dermatoses such as dermatitis, eczema, atopic dermatitis, allergic contact dermatitis, urticaria; vasculitis (e.g., necrotizing, cutaneous, and hypersensitivity vasculitis); spondyloarthropathies; scleroderma; respiratory allergic diseases such as asthma, allergic rhinitis;

autoimmune diseases, such as arthritis (e.g., rheumatoid arthritis, psoriatic arthritis), multiple sclerosis, systemic lupus erythematosus, myasthenia gravis, juvenile onset diabetes, glomerulonephritis and other nephritides, autoimmune thyroiditis, Behcet's disease;

graft rejection (e.g., in transplantation), including allograft rejection or graft-versus-host disease;

other diseases or conditions in which undesirable inflammatory responses are to be inhibited can be treated, including, but not limited to, atherosclerosis, restenosis, myositis (including polymyositis, dermatomyositis).

Modes of Administration

A "subject" is preferably a human, but can also be a mammal in need of veterinary treatment, e.g., domestic animals (e.g., dogs, cats, and the like), farm animals (e.g., cows, sheep, fowl, pigs, horses, and the like) and laboratory animals (e.g., rats, mice, guinea pigs, and the like).

An "effective amount" of an agent (e.g., antagonist of chemokine receptor (e.g., CCR2) function, cellular adhesion molecule (e.g., β2 integrin) antagonist) is an amount sufficient to achieve a desired therapeutic and/or prophylactic effect, such as an amount sufficient to inhibit (i.e., reduce or prevent) recruitment and/or adhesion of neutrophils and/or mononuclear cells to sites of vascular injury, and thereby inhibit stenosis or restenosis. For example, an effective amount of a cellular adhesion molecule antagonist is an amount sufficient to inhibit binding of neutrophils and/or mononuclear cells to a site of vascular injury. An effective amount of an antagonist of chemokine receptor (e.g., CCR2) function is an amount sufficient to inhibit a (i.e., one or more) function of the receptor (e.g., ligand-induced cellular migration, ligand-induced integrin activation, ligand-induced transient increase in the concentration of intracellular free calcium $[Ca^{2+}]_i$, and/or ligand-induced secretion (e.g. degranulation) of proinflammatory mediators), and thereby inhibit recruitment and/or adhesion of neutrophils and/or mononuclear cells to a site of vascular injury.

If desired, the agent(s) which inhibit recruitment and/or activation of neutrophils and/or mononuclear cells to a site of vascular injury can be co-administered with one or more addition therapeutic agents, for example, a fibrinolytic agent (e.g., Retavase), a thrombolytic agent, such as a plasminogen activator (e.g., tissue plasminogen activator, urokinase, streptokinase, recombinant plasminogen activator), anticoagulant (e.g., heparin, hirulog, hirudin, aspirin), or a coumarin anticoagulant (e.g., warfarin, ethyledine dicoumarol), a β-adrenergic blocker (e.g., alprenolol, acebutolol, propanolol), calcium channel blocker (e.g., nifedipine, diltiazem, cinnarizine, bencyclane), gpIIb/IIIa antagonists (e.g., c7E3 Fab (ReoPro®, abciximab, Centocor, Inc., Malvern, Pa.)), vasodilator (e.g., nitroglycerin, amotriphene, erythritol, prenylamine) or an agent which stimulates the production of nitric oxide (see, for example, Singh et al., U.S. Pat. No. 5,811,437).

The amount of agent (e.g., cellular adhesion molecule antagonist, antagonist of chemokine receptor function, additional therapeutic agent) administered to the individual will depend on the characteristics of the individual, such as general health, age, sex, body weight and tolerance to drugs as well as the degree, severity and type of vascular injury and desired therapeutic effect. The skilled artisan will be able to determine appropriate dosages which can be dependent on these and other factors. Typically, an effective amount can range from about 0.01 mg per day to about 100 mg per day for an adult. Preferably, the dosage ranges from about 1 mg per day to about 100 mg per day or from about 1 mg per day to about 10 mg per day. Antibodies and antigen-binding fragments thereof, particularly human, humanized and chimeric antibodies and antigen-binding fragments thereof can often be administered with less frequency than other types of therapeutics. For example, an effective amount of an antibody or antigen-binding fragment thereof can range from about 0.01 mg/kg to about 5 or 10 mg/kg administered daily, weekly, biweekly or monthly.

The agent (e.g., cellular adhesion molecule antagonist, antagonist of chemokine receptor function, additional therapeutic agent) can be administered by any suitable route, including, for example, orally (e.g., in capsules, suspensions or tablets) or by parenteral administration. Parenteral administration can include, for example, intramuscular, intravenous, intraarterial, intraarticular, intrathecal, subcutaneous, or intraperitoneal administration. The agent (e.g., cellular adhesion molecule antagonist, antagonist of chemokine receptor function, additional therapeutic agent) can also be administered orally (e.g., dietary), transdermally, topically, by inhalation (e.g., intrabronchial, intranasal, oral inhalation or intranasal drops) or rectally. Administration can be local (e.g., at the site of vascular injury) or systemic as indicated. The agent can be administered in a single dose, continuous infusion, or in multiple doses and/or infusions (e.g., a bolus dose followed by continuous infusion). The preferred mode of administration can vary depending upon the particular agent (e.g., cellular adhesion molecule antagonist, antagonist of chemokine receptor function, additional therapeutic agent) chosen, however, oral or parenteral administration is generally preferred.

Preferably, the timing of administration of an effective amount of the agent(s) is selected to provide for inhibition of recruitment and/or activation of neutrophils and mononuclear cells at the time of vascular injury. It is also preferred that the agent which inhibits neutrophil recruitment and/or adhesion be administered in an amount and with a frequence which is sufficient to inhibit neutrophil recruitment and/or adhesion to a site of vascular injury for about one week following vascular injury. The agent which inhibits mononuclear cell recruitment and/or adhesion is preferably administered in an amount and with a frequency which is sufficient to inhibit mononuclear cell recruitment and/or adhesion to a site of vascular injury for a period of at least about two weeks to about 1 year following vascular injury. In some instances it can be desirable to administer an agent which inhibits neutrophil recruitment and/or adhesion prior to or subsequent to administration of an agent which inhibits mononuclear cell recruitment and/or adhesion. For example, in one embodiment an agent which inhibits neutrophil recruitment and/or adhesion to a site of vascular injury is administered to a subject after an agent which inhibits mononuclear cell recruitment and/or activation to a site of vascular injury. The skilled artisan will be able to determine appropriate dosage and timing for administration of the agents based upon the particular agents selected, characteristics of the subject and other factors.

For example, where a subject is scheduled to undergo a vascular intervention procedure (e.g., PTCA), a first agent which inhibits recruitment and/or adhesion of neutrophils to a site of vascular injury and a second agent which inhibits recruitment and/or adhesion of mononuclear cells to a site of vascular injury can be administered prior to the procedure and/or periprocedurally. The first agent and the second agent can be administered as a single dose or repeatedly, if necessary to maintain inhibition of recruitment and/or adhesion of neutrophils and mononuclear cells at a site of vascular injury for about one week following the vascular intervention procedure. At that time, administration of the first agent can be discontinued and the second agent can be administered as necessary to maintain inhibition of recruitment and/or adhesion of mononuclear cells at a site of vascular injury for a period of at least about two weeks to about 1 year following the vascular intervention procedure.

The agent (e.g., cellular adhesion molecule antagonist, antagonist of chemokine receptor function, additional therapeutic agent) can be administered as a neutral compound or as a salt. Salts of compounds containing an amine or other basic group can be obtained, for example, by reacting with a suitable organic or inorganic acid, such as hydrogen chloride, hydrogen bromide, acetic acid, perchloric acid and the like. Compounds with a quaternary ammonium group also contain a counteranion such as chloride, bromide, iodide, acetate, perchlorate and the like. Salts of compounds containing a carboxylic acid or other acidic functional group can be prepared by reacting with a suitable base, for example, a hydroxide base. Salts of acidic functional groups contain a countercation such as sodium, potassium and the like.

The agent(s) (e.g., cellular adhesion molecule antagonist, antagonist of chemokine receptor function, as described herein) can be administered to the subject as part of a pharmaceutical or physiological composition for inhibiting stenosis or restenosis. Such a composition can comprise an (i.e., one or more) agent (e.g., cellular adhesion molecule antagonist, antagonist of chemokine receptor function, additional therapeutic agent) and a physiologically acceptable carrier. Pharmaceutical compositions can further comprise one or more additional therapeutic agents (e.g., anticoagulant, thrombolytic agent). Alternatively, an agent (e.g., cellular adhesion molecule antagonist, antagonist of chemokine receptor function, as described herein) and an additional therapeutic agent can be components of separate pharmaceutical compositions which can be mixed together prior to administration or administered separately. Formulation will vary according to the route of administration selected (e.g., solution, emulsion, capsule). Suitable pharmaceutical carriers can contain inert ingredients which do not interact with the agent(s) (e.g., cellular adhesion molecule antagonist, antagonist of chemokine receptor function, additional therapeutic agent). Standard pharmaceutical formulation techniques can be employed, such as those described in Remington's Pharmaceutical Sciences, Mack Publishing Company, Easton, Pa. Suitable physiological carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al, "Controlled Release of Biological Active Agents", John Wiley and Sons, 1986).

EXAMPLE

The effects of murine monoclonal antibodies which bind human integrin CD18 or human chemokine receptor CCR2 in a model of restenosis in cynomolgus monkeys was evaluated.

Study Design

Cynomolgus monkeys were randomized on the basis of body weight to groups to receive treatment with either an irrelevant murine monoclonal antibody (mAb) as an IgG2a isotype control (S-S.1), an anti-human CCR2 mAb (1D9) or an anti-human CD18 mAb (1B4). Animals were administered a loading dose of mAb intravenously (IV) on Day-1, followed by daily SC injections on Days 1–13. On Day 1, all animals underwent bilateral balloon angioplasty-induced iliac artery endothelial denudation, followed by intravascular stent placement, as a model of restenosis. Animals were euthanized at the end of the test period to allow perfusion fixation and collection of the iliac arteries and other tissue samples (see Table A).

Efficacy of treatment was evaluated by use of quantitative angiography at the time of stent placement and at the end of the study, and by immunohistologic and morphometric evaluation of iliac artery tissue. Blood samples were collected periodically for assay of serum mAb levels (pharmacokinetics), leukocyte mAb binding (pharmacodynamics), anti-mAb antiglobulin response (immunogenicity), and for hematology and serum chemistry (safety). Safety was further evaluated by recording vital signs during infusion and body weights, clinical observations and injection site observations during the test period. Other tissue samples were not evaluated unless warranted (see Table B).

TABLE A

Study Design

| | | Treatment | | | |
|---|---|---|---|---|---|
| Group No. (Description) | No. Animals | Test Materials | Dose and Dose Regimen | Model of Restenosis | Euthanasia |
| 1 (IgG2a control) | 5 | S-S.1 | 5 mg/kg, IV, in 30 mL over 30 min on Day −1; | Bilateral balloon angioplasty-induced iliac artery endothelial denudation and intravascular stent placement on Day 1 | Day 29 |
| 2 (anti-CCR2) | 5 | 1D9 | 1 mg/kg, SC, in 3 mL on Days 1–13 | | |
| 3 (anti-CD18) | 5 | 1B4 | | | |

There is no Day 0; Day −1 precedes Day 1. Day 1 was not the same calendar day for all animals.
Day −1 treatment was via peripheral vein. Day 1–13 SC treatment was given in the intrascapular area. Day 1 treatment was prior to angioplasty/stenting.
Doses were based on Day −1 body weight and were maintained throughout the treatment period.
IV = intravascular; SC subcutaneous; M = male.

TABLE B

Study Procedures

| | PK Sera mAb | PD mAb | IMG Anti mAb | | | | Safety | | | | Efficacy |
|---|---|---|---|---|---|---|---|---|---|---|---|
| Study Day | conc. | binding | Abs | Hem | SC | BW | Clinical Obs. | Injection Site Obs. | Vital Signs | Nx | Quantitative Angiography |
| | | | Blood Collection | | | | | | | | |
| BL | X | X | X | X | X | X | Day −1 | | X | | |
| −1 | X (pre) X (post) | X (pre) X (post) | X (pre) | X (pre) | X (pre) | X | (pre and post) then daily | | | | |
| 1 | X | X | X | | | | | Day 1 (pre and post) then daily | | | X |
| 8 | X | X | X | X | X | X | | | | | |
| 15 | X | X | X | X | X | X | | | | | |
| 22 | X | X | X | X | X | X | | | | | |
| 29 | X | X | X | X | X | X | | | | X | X |
| Vol. (mL) | 1.0 | 1.0 | 1.0 | 0.5 | 1.0 | | | | | | |
| Anti coag-ulant | None | Heparin | None | EDTA | None | | | | | | |
| Notes | a (3rd) | b (1st) | a (3rd) | c (2nd) | d (4th) | | | | | | | a = Prioritize as 3rd sample(s). Freeze (−70° C.) in 100 μL aliquots.
b = Prioritize as 1st sample.
c = Prioritize as 2nd sample collected. Use microtainers.
d = Prioritize as 4th sample. Freeze (−70° C.) residual sera in single aliquot.
Procedures (except vital signs, angiography and Nx) were done prior to treatment, unless otherwise specified.
Abbreviations: Abs = antibodies; BL = baseline; BW = body weight; Hem = hematology; IMG = immunogenicity; mAb = monoclonal antibody; Nx = euthanasia, perfusion and tissue collection; PD = pharmacodynamics; PK = pharmacokinetics; pre/post = pre- and post-infusion; SC = serum chemistry; X = was performed.

Disease Model

Atherosclerosis is a disease in humans in which lipid-rich fibro-inflammatory plaques accumulate within the wall of the coronary vessels, encroaching upon and narrowing ("stenosing") the lumen, thus limiting oxygenated blood supply to cardiac tissue and resulting in acute myocardial pain and/or infarction. Current medical practice to address compromised coronary vessels involves mechanical dilatation of the vessel with a balloon catheter via percutaneous transluminal coronary angioplasty (PCTA), often followed by placement of an intravascular stent to maintain luminal diameter.[1] In a significant number of patients, late(r) restenosis limits the effectiveness of this procedure.[2] Neointimal hyperplasia, vascular smooth muscle cell (VSMC) proliferation and infiltrative leukocytes characterize the area of restenosis. Possible mechanisms involved in this process include platelet aggregation (thrombosis), endothelial cell activation and VSMC proliferation and migration. A variety of animal models of atherosclerosis and/or restenosis have been developed, in species such as mice, rats, rabbits, pigs, and nonhuman primates (cynomolgus monkeys and baboons). The model of neointimal hyperplasia used in this study, balloon angioplasty-induced endothelial denudation followed by stent placement, has been previously used in rabbits to elucidate some of the mechanisms involved in restenosis.[4]

Test Materials

1D9 is a murine IgG2a mAb that recognizes CCR2 on monocytes of humans and nonhuman primates. 1B4 is a murine IgG2a mAb that recognizes CD18 on human, non-human primate and rabbit neutrophils. 1B4 was produced using a commercially available cell line that makes the antibody (ATCC Accession No. HB-10164). S-S.1 is a murine IgG2a mAb directed against sheep red blood cells.

S-S.1 was produced using a commercially available cell line that makes the antibody (ATCC Accession No. TIB-111) and is being used as an irrelevant isotype-matched control antibody.

Dose and Dose Regimen

The dose and dose regimen were selected because they were anticipated to result in peak and trough sera mAb concentrations in excess of those required to maintain continuous saturation of CCR2 or CD18 on leukocytes through at least Day 14. It was recognized that neutralizing monkey anti-mouse mAb antiglobulin (MAMA) responses would develop in these animals and that these responses may have affected sera or cell-bound mAb levels and thus PK, PD and/or efficacy endpoints.

Vital Sign Monitoring

These mAbs, as with many other antibodies, have the potential to induce a "first-dose effect" related to cytokine release during initial infusion, or to precipitate ADCC (antibody-dependent cell-mediated cytotoxicity) or complement-mediated cell lysis. These effects can result in transient adverse physiologic changes, such as hypotension and bronchoconstriction, which are usually not life threatening. Monitoring vital signs allowed detection of such changes.

Test System

The murine anti-human CCR2 mAb and murine anti-human CD18 mAb also bind Cynomolgus monkey CCR2 and CD18, respectively.

Number of Animals

The number of animals used in this study was sufficient for evaluation of the results. Although 4 animals/group has previously been sufficient to allow detection of efficacy in a rabbit model,[4] it was considered appropriate to use 5 animals/group in this study because of potentially greater variability in degree of vascular injury and response thereto in monkeys.

TEST MATERIALS AND FORMULATION

Characterization

The mAb solutions were biochemically characterized prior to use (see Table C).

Stability

Samples of the test articles were retrieved from the test site at completion of dosing and characterized biochemically. No significant changes in the samples, relative to the original characterization, were detected.

Dose Formulation Methods

On the day(s) of use, an appropriate number of vials of the frozen mAb solutions were brought to room temperature and appropriate volumes diluted in vehicle (saline) as necessary to provide uniform total volumes for IV (30 mL in a 60 cc syringe) or SC (3 mL in a 3 cc syringe) administration to all animals. The date of thawing was recorded on the vial(s). Unused (thawed, opened) bulk mAb solutions were refrigerated (2–8° C.) for use on subsequent day(s).

Dose Formulation Samples

No dose formulation samples were collected.

Disposition

Residual diluted dose formulations were discarded.

TABLE C

Test Materials

| Identification | Conc. | Storage Conditions | Physical Description | Supplier | Manufacturer | Lot No. | Biohazards |
|---|---|---|---|---|---|---|---|
| Saline (Vehicle for dilution) | N/A | Ambient | Clear liquid | Primedica | TBD | TBD | None; Use standard precautions |
| S-S.1 (Irrelevant IgG2a control mAb)[a] | 4.2 mg/mL | −70° C. until thawed, then 2–8° C. | Clear to slightly cloudy solution | LeukoSite | LeukoSite | TBD | |
| 1D9 (Anti-CCR2 mAb) | 6.8 mg/mL | | | | Therapeutic Antibody Center | LS132-1D9 Batch 2 | |
| 1B4 (Anti-CD18 mAb)[b] | 5 mg/mL | | | | LeukoSite | TBD | |

[a]Cell line obtained from ATCC; No. TIB-111 also referred to as S-S.1.
[b]Cell line obtained from ATCC; No. HB-10164.
TBD documented in study file; ATCC American Type Culture Collection

TEST SYSTEM

Animals
Species: *Macaca fascicularis*
Common name: Cynomolgus monkey
Number of Animals: 15
Age and Gender: Young-adult males
Weight at Initiation of Treatment: ~4 kg Source and Selection Animals were obtained from a source approved by the Testing Facility. Animals were selected from those available at the time of the study and appeared to be in good health, as determined by a veterinarian. All animals completed a period of quarantine, and each animal was identified by a unique number. All animals used in the study were euthanized at the end of the study.

ANIMAL CARE

The Testing Facility was accredited by the Association for Assessment and Accreditation of Laboratory Animal Care (AAALAC) and licensed by the United States Department of Agriculture (USDA) to conduct research in laboratory animals in compliance with the Animal Welfare Act, USDA regulations and National Research Council (NRC) guidelines.[3,4,5] Animal activities described herein were subject to review and approval by the Institutional Animal Care and Use Committee (IACUC) of the Testing Facility.

Animal husbandry, diet, water and environmental conditions were performed in compliance with NRC guidelines[17] and Testing Facility standard operating procedures (SOPs).

METHODS

Randomization
Animals considered suitable for the study were randomized to treatment groups by body weight and assigned unique consecutive identification numbers within each group. The order in which animals were assigned to undergo procedures was rotated among groups on the basis of identification numbers to minimize procedural bias.

Acclimation to Physical Restraint
Animals were acclimated to the rope-and-collar method of physical restraint and to restraint in a primate chair prior to initiation of treatment.

Tranquilization
Animals were tranquilized (ketamine HCl, 5–10 mg/kg, IM, to effect) as necessary to facilitate handling, blood collection or other technical procedures.

Fasting
All food was withheld overnight prior to tranquilization or anesthesia. Water was not be withheld.

Dose Calculation
Doses were calculated based on Day-1 body weight. The doses were maintained throughout the treatment period.

Dose Administration
All treatments were administered using in-line or syringe-tip low protein-binding filters. IV treatments were administered while animals were restrained in a primate chair, via a percutaneous catheter placed in a peripheral vein, using a clinical grade infusion pump. SC treatment were given in the intrascapular area, using a 23-gauge needle.

Blood Collection
Blood samples were collected from tranquilized animals via direct venipuncture of a femoral vein. Blood collection was alternated between left and right femoral veins when possible. Considerable efforts were made to minimize local vascular trauma or bleeding. It was acceptable to not collect individual samples if difficulty in collecting them suggested the likelihood of inducing local vascular trauma (e.g. hematoma formation, arteriopuncture).

Concurrent Therapy
Concurrent therapy in accordance with accepted veterinary practices was utilized if deemed necessary by a veterinarian.

Animal Observation
Body weights were recorded approximately weekly (see Table B). Cage side observations for moribundity and mortality were performed twice daily.

Clinical Observations
Clinical observations for evidence of treatment-related effects were performed beginning prior to and approximately 1 hour after treatment on Day-1, and daily thereafter. On days of SC treatment clinical observations were performed prior to treatment.

Injection Site Observations
The SC injection site (interscapular area) was observed beginning prior to injection on Day 1, and daily thereafter. The site was subjectively scored for swelling and/or erythema (0=none, 1=mild, 2=moderate, 3=marked).

Vital Sign Monitoring During Infusion
During IV treatment vital signs (heart rate, respiratory rate, rectal body temperature and indirect blood pressure) were monitored intermittently for indications of adverse reactions. Representative values for these parameters were recorded prior to, at ~10 minute intervals during, and at the end of infusion.

If adverse reactions occurred, treatment may have been interrupted or discontinued. A Testing Facility veterinarian determined the appropriate therapy, if any, in consultation with the Study Director and/or study Sponsor's Representative.

ANGIOPLASTY AND STENTING PROCEDURES

Anticoagulant Therapy
Animals received aspirin (~40 mg, orally) daily to provide anticoagulant function and minimize stent thrombosis beginning on Day-3.

Antibiotic Therapy
Animals received a single prophylactic injection of benzathine/procaine penicillin-G (42,000 IU/kg, IM) on Day 1 prior to angioplasty.

Anesthesia
Animals were pre-anesthetized (ketamine HCl, 10 mg/kg, IM; atropine $SO_4$, 0.04 mg/kg, IM) then intubated and maintained in anesthesia with isoflurane inhalant anesthetic gas.

Preparation
Animals were positioned on a procedure table in dorsal recumbency. The bladder was catheterized to prevent urine accumulation. Sites for vascular access were clipped and prepared for aseptic surgery. A catheter was placed in a peripheral vein to facilitate maintenance fluid administration (lactated Ringer's solution, 5–10 mL/kg/hr).

Heparinization
Heparin (100 U/kg, IV, initially) was administered prior to angioplasty to provide anticoagulation. Activated clotting time (ACT) was monitored periodically and additional heparin was administered as necessary to maintain ACT values >250 seconds for the duration of the angioplasty procedure.

Instrumentation
The right carotid artery was surgically exposed and a 6Fr percutaneous vascular introducer sheath (e.g. CP-07711, ARROW International, Reading, Pa. 19605) was placed to facilitate interventional catheter placement.

Utilizing fluoroscopic guidance, a 6Fr guide catheter was passed antegrade to the level at which the distal abdominal aorta bifurcates into the right and left iliac arteries. A radiopaque 0.014-inch guide wire (e.g. 22225M, Advanced Cardiovascular Systems, Inc., Temecula, Calif. 92591) was used to facilitate passage of the guide catheter or other catheters as necessary. Radiopaque contrast media (e.g. Omnipaque™, iohexol injection, Nycomed, Princeton, N.J. 75039) was used as necessary to facilitate fluoroscopy.

Videotaping of Angiography
The fluoroscopic procedures were videotaped for each animal to facilitate measurements for quantitative angiography. Information identifying the study number, study day, animal number and procedure were also recorded on the videotape.

Pre-angioplasty Angiography
Prior to angioplasty, nitroglycerine (50 $\mu$g, IA) was administered to induce arterial dilatation. Radiopaque contrast media was administered to facilitate angiography.

Endothelial Denudation via Balloon Angioplasty
An 80 cm, 3Fr Fogarty balloon embolectomy catheter (e.g. 120803F, Baxter Healthcare Corp., Irvine, Calif. 92714) with a balloon appropriately sized for the vessel was passed via the guide catheter into the right iliac artery, to a level about 4 cm distal to the aortic bifurcation. The balloon was then inflated with 0.6 cc air and withdrawn inflated over an about 3 cm section of artery to facilitate endothelial denudation. Balloon angioplasty was performed three times. This procedure was then repeated in the contralateral (left) iliac artery and the balloon embolectomy catheter was withdrawn. In some cases the left iliac artery was denuded first, followed by the right.

Stent Placement
An appropriate-sized dilation catheter (Ninja™ PTCA dilation catheter with SLX™ coating, Cordis Corp., Miami Fla. 33102) fitted with a balloon-expandable 7-mm stent (e.g., one half of a 15-mm long stent (e.g. CS 15-030, Palmaz-Schatz® crown balloon-expandable stent, Cordis Corp., Miami Fla. 33102)) was then passed into the right iliac artery to the level of the midpoint of endothelial denudation. The balloon was inflated to the appropriate inflation pressure required to expand the stent sufficiently to provide a balloon/stent:artery ratio of 1.1–1.2 (typically 6 Atm for 2.5, 3.0 or 3.5 mm catheters). The balloon was deflated and the catheter was withdrawn. This procedure was repeated in the contralateral (left) iliac artery. In some cases the left iliac artery was stented first, followed by the right.

Post-angioplasty Angiography

Approximately 10 min after placement of the second stent, nitroglycerine (50 μg, IA) was administered to induce arterial dilatation for quantitative angiography of both arteries. Radiopaque contrast media was administered to facilitate angiography.

Recovery

The vascular introducer sheath was removed and the carotid artery was ligated. The incision was closed with appropriate suture. The animals recovered from anesthesia and were returned to their cages.

Analgesia

Animals received a single injection of buprenorphine (0.01 mg/kg, IM) after completion of the procedures.

Follow-up Angiography

Anesthesia

Prior to euthanasia and arterial tissue collection (see Paragraph VIII.L) animals were pre-anesthetized (ketamine HCl, 10 mg/kg, IM; atropine $SO_4$, 0.04 mg/kg, IM) then intubated and maintained in anesthesia with isoflurane inhalant anesthetic gas.

Preparation

Animals were positioned on a procedure table in dorsal recumbency. A catheter was placed in the peripheral vein. The incision site was clipped and washed; strict asepsis was not required for this terminal procedure.

Method

Heparin (150 U/kg, IV) was administered. Radiopaque contrast media was used as necessary to facilitate fluoroscopy. The left carotid artery was surgically exposed and a 6Fr percutaneous vascular introducer sheath placed. Utilizing fluoroscopic guidance, a 6Fr guide catheter was passed antegrade to the level at which the distal abdominal aorta bifurcates into the right and left iliac arteries. Nitroglycerine (50 μg, IA) was administered. Radiopaque contrast media was administered to facilitate angiography. The fluoroscopic procedures were videotaped for each animal to facilitate measurements for quantitative angiography.

Arterial Tissue Collection

Euthanasia

Animals were already anesthetized for follow-up angiography. Animals were euthanized in accordance with American Veterinary Medical Association (AVMA) guidelines[3] by deep anesthesia (sodium pentobarbital, 35 mg/kg, V), followed by exsanguination.

Perfusion

A midline laparotomy incision was made and a cannula was placed in the descending abdominal aorta and advanced to the level of the bifurcation. The iliac arteries were flushed with 100 mL lactated Ringer's solution, followed by perfusion with 0.4% paraformaldeyde (PFA) for about 5 min at 100 mmHg pressure.

Arterial Tissue Removal

Right and left iliac arteries were separately excised, with the proximal ends identified (e.g. by ligature), and immersed in 0.4% PFA.

Limited Gross Necropsy

Animals underwent a limited necropsy, defined as evaluation of the external body and abdominal and thoracic cavities.

Limited Organ/Tissue Collection

Representative samples from specified organs and tissues (see Table D) were collected and fixed in 10% neutral-buffered formalin for histopathologic evaluation or embedded and frozen in OCT for immunohistology.

TABLE D

| Limited Organ/Tissue Collection | |
| --- | --- |
| Injection sites (interscapular area) | Brain (cerebrum) |
| Adrenal glands | Heart |
| Bone marrow (sternum) | Ileum (ileocecocolic junction) |
| Eyes[a] | Kidney |
| Heart | Liver |
| Kidneys | Lung |
| Large intestine (cecum, colon) | Lymph node (iliac, inguinal) |
| Liver | Sciatic nerve |
| Lung | Spinal cord |
| Lymph nodes (axillary, inguinal, mesenteric) | Spleen |
| | Thymus |
| Small intestine (duodenum, jejunum, ileum) | |
| Spleen | |
| Thymus | |
| Thyroid gland (with parathyroid) | |

[a]Eyes were fixed in Davidson's fixative.
[b]All cell counts were reported as absolute values only. Other cell types (e.g. precursor cells) if observed were counted. Other morphologic features (e.g. RBC staining characteristics) if present, were documented.

SAMPLE PROCESSING

Blood Samples

Hematology

Blood samples were analyzed (see Table E) using a hematology analyzer. Blood smear differential were performed by manual microscopy.

Serum Chemistry

Serum samples were analyzed using a chemistry analyzer (see Table F).

TABLE E

| Hematology Parameters | |
| --- | --- |
| Total leukocyte count (WBC) | Blood smear evaluation and differential:[b] |
| Erythrocyte count (RBC) | |
| Hemoglobin concentration (HGB) | Segmented neutrophil count (APLY) |
| Hematocrit value (HCT)[a] | Band neutrophil count (ABND) |
| Mean corpuscular volume (MCV)[a] | Lymphocyte count (ALYM) |
| Mean corpuscular hemoglobin (MCH)[a] | Monocyte count (AMNO) |
| Mean corpuscular hemoglobin concentration (MCHC)[a] | Eosinophul count (AEOS) |
| Platelet count (PLT) | Basophil count (ABSO) |
| | Nucleated RBC count (ANRC) |

[a]Calculated value.
[b]All cell counts were reported as absolute values only. Other cell types (e.g. precursor cells), if observed, were counted. Other morphologic features (e.g. RBC staining characteristics) if present, were documented.

TABLE F

| Serum Chemistry Parameters | |
| --- | --- |
| Glucose (GLU) | Sodium (NA) |
| Blood urea nitrogen (BUN) | Potassium (K) |
| Creatinine (CRE) | Chloride (CL) |

TABLE F-continued

Serum Chemistry Parameters

| | |
|---|---|
| Total protein (TPR) | Total cholesterol (CHOL) |
| Albumin (ALB) | Total bilirubin (TBIL) |
| Globulin (GLOB)a | Triglycerides (TRG) |
| Albumin/Globulin ratio | Alanine aminotransferase (ALT) |
| (A/G)a | Aspartate aminotransferase (AST) |
| Calcium (CAL) | Alkaline phosphatase (ALK) |
| Phosphorus (PHOS) | |
| Gama glutamyl transferase | |
| (GGT) | | a Calculated value.

Samples for Additional Analyses

Blood samples for pharmakodynamic assays and sera samples for pharmacokinetic and immunogenicity assays were obtained.

Pharmacokinetics

Serum therapeutic 1B4 or 1D9 monoclonal antibody (mAb) levels were determined by enzyme-linked immunosorbent assay (ELISA) for murine IgG.

Briefly, 96-well plates (NUNC #4-39454) were coated with 100 μl goat-anti-mouse IgG+IgM antibody (Jackson Immunoresearch #115-005-068) at 2.5 μg/ml in carbonate buffer pH 9.3 overnight at 4° C. Plates were subsequently washed 3 times with PBS 0.5% Tween-20 and blocked with 300 μl PBS/1% BSA for 60 minutes at 37° C. Following 3 additional washes with PBS-Tween, serum samples were diluted 1:100 in PBS/1% BSA and 100 μl aliquots were added to duplicate wells in the plate. The antibody standard (MOPC-21, Sigma) was diluted to 50 ng/ml and 100 μl aliquots were added to the plate. Subsequently, all samples were diluted 2-fold across the plate and incubated at room temperature for 2 hours. The plate was subsequently washed again with PBS/0.5% Tween-20 and 100 μl of peroxidase-conjugated goat anti-mouse IgG+IgM (Jackson Immunoresearch #115-035-068) was added at a concentration of 375 ng/ml and incubated for 2 hours at room temperature. Following additional washes with PBS-Tween, plates were developed with o-phenylenediamine (OPD, Sigma) in citric acid buffer pH 5.0, and analyzed on a 96-well fluorescent plate reader (Dynatech MR4000) at 492 nm. The dilutions of the antibody standard was used to construct a standard curve, and the serum antibody concentration was automatically derived from the standard curve and dilution factor data provided using Biolinx 2.22 software.

Pharmacodynamics

Target Saturation

Saturation of 1B4 target (CD18) or 1D9 target (CCR2) on appropriate leukocyte subsets (neutrophils and monocytes for CD18 and monocytes for CCR2) was determined by flow cytometry assays.

Determination of Saturation of Circulating Leukocytes with 1D9 (Anti-CCR2)

Blood was collected in heparin from the test animals at specified intervals prior to and after the administration of 1D9. Samples of whole blood were stained ("spiked") with supersaturating amounts of 1D9 or nothing. The blood samples were washed in buffer and stained with FITC conjugated goat-anti-mouse IgG. After daily standardization of the flow cytometer with FITC-labeled beads, to ensure equivalent day-to-day sensitivity to FITC, the blood was lysed (red blood cells were lysed) using ammonium chloride lysing solution and the fluorescence of lymphocyte, monocyte and granulocyte populations was determined. The degree of saturation of CCR2 on monocytes by the administered 1D9 was determined by the difference between the mean channel fluorescence (MCF) of the sample with no added 1D9 and the sample with the added spike of 1D9. In practice, CCR2 on the surface of the cells which were not coated with the 1D9 delivered in vivo was stained by the exogenously added 1D9 and the mean channel fluorescence of the unspiked sample was dimmer than the mean channel fluorescence of the spiked sample. The difference in staining intensity is a reflection of free (unsaturated) CCR2 on the cell surface.

Determination of Saturation of Circulating Leukocytes with 1B4 (Anti-CD18)

Blood was collected in heparin from the test animals at specified intervals prior to and after the administration of 1B4. Samples of whole blood were stained ("spiked") with supersaturating amounts of 1B4 or nothing. The blood samples were washed in buffer and stained with FITC conjugated goat-anti-mouse IgG. After daily standardization of the flow cytometer with FITC-labeled beads, to ensure equivalent day-to-day sensitivity to FITC, the blood was lysed (red blood cells were lysed) using ammonium chloride lysing solution and the fluorescence of lymphocyte, monocyte and granulocyte populations was determined. The degree of saturation of CD18 on either neutrophils or monocytes by the administered 1B4 was determined by the difference between the mean channel fluorescence (MCF) of the sample with no added 1B4 and the sample with the added spike of 1B4. In practice, free CD18 on the surface of the cells which were not coated with the 1B4 delivered in vivo was stained by the exogenously added 1B4 and the mean channel fluorescence of the unspiked sample was dimmer than the mean channel fluorescence of the spiked sample. The difference in staining intensity was a reflection of free (unsaturated) CD18 on the cell surface.

Determination of Saturation of Circulating Leukocytes with S-S.1 (Irrelevant Isotype Control Antibody, also Referred to as TIB-111)

S-S.1 is a non-cell binding irrelevant murine antibody. Assays to determine potential "saturation" of leukocyte antigens with this mAb were performed as above, with the understanding that a positive result (cell staining) was unlikely to be seen and that there would consistently be no difference in mean channel fluorescence between unspiked and spiked samples over time.

Peripheral Blood Leukocyte Dynamics

The effect of mAb administration on leukocyte dynamics (trafficking, margination/demargination) was identified indirectly by evaluating the numbers of leukocytes in circulation, as compared to prior to treatment. Inhibition of leukocyte adhesion and/or chemotaxis would be expected to prevent normal trafficking and to result in elevated circulating cell numbers. Routine hematology was performed to determine the total numbers of peripheral blood leukocytes, as well as the number of neutrophils, lymphocytes and monocytes.

Immunogenicity

Measurement of Antibody Responses to 1D9 (Anti-CCR2)

Sera samples were collected at specified times and stored frozen until completion of the study. Anti-1D9 antibodies were detected using two assays.

The first assay was designed to detect both anti-idiotype and anti-isotype antibodies. This assay was performed by coating the wells of a microtiter plate with 1D9 and blocking unused protein binding sites with BSA. The sera were then diluted appropriately and several dilutions were added to duplicate wells of the plate. Antibodies in the sera were allowed to bind for 2 hours at 37 degrees C., and then the wells were shaken out and washed 3 times in PBS with Tween 20. Monkey anti-1D9 antibodies were detected with HRP-conjugated goat anti-human IgG (absorbed against mouse proteins). After 2 hours, unbound detection antibody was washed away in three washes of the plate with PBS Tween. Bound complexes were detected by the addition of o-phenylenediamine to produce a yellow color. Color was read at 490 nm on an ELISA plate reader. Titers were determined by calculating the inverse of the dilution of the sera which produced an optical density equivalent to the optical density produced by a specific dilution of a commercial HRP-conjugated goat anti-mouse IgG (absorbed against human serum proteins).

The second assay was used to assess the proportion of the response which reacted with the 1D9 idiotype compared with the response to mouse IgG2a. This was a competitive ELISA in which the sera from a peak antibody response sample were diluted to produce an optical density between 0.6–1.0. The diluted sera were added to triplicate wells of an ELISA plate coated with 1D9 as above. The sera was added alone, mixed with 5 μg of commercial mouse IgG2a, or mixed with 5 μg of 1D9. The ELISA was carried out as above and monkey antibody bound to the 1D9 on the plate was detected using HRP-anti-human IgG, as above. By comparing the optical density of signals produced by the uncompeted sera with those produced by sera spiked with mouse IgG2a or 1D9 it was possible to assess the specificity of the anti-1D9 antibodies which developed in animals treated with 1D9.

Measurement of Antibody Responses to 1B4 (CD18)

Sera samples were collected at specified times and stored frozen until completion of the study. Anti-1B4 antibodies were detected using two assays.

The first assay was designed to detect both anti-idiotype and anti-isotype antibodies. This assay was performed by coating the wells of a microtiter plate with 1B4 and blocking unused protein binding sites with BSA. The sera was then diluted appropriately and several dilutions were added to duplicate wells of the plate. Antibodies in the sera were allowed to bind for 2 hours at 37 degrees C., and then the wells were shaken out and washed 3 times in PBS with Tween 20. Monkey anti-1B4 antibodies were detected with HRP-conjugated goat anti-human IgG (absorbed against mouse proteins). After 2 hours, unbound detection antibody was washed away in three washes of the plate with PBS Tween. Bound complexes were detected by the addition of o-phenylenediamine to produce a yellow color. Color was read at 490 nm on an ELISA plate reader. Titers were determined by calculating the inverse of the dilution of the sera which produced an optical density equivalent to the optical density produced by a specific dilution of a commercial HRP-conjugated goat anti-mouse IgG (absorbed against human serum proteins).

The second assay was used to assess the proportion of the response which reacted with the 1B4 idiotype compared with the response to mouse IgG2a. This was a competitive ELISA in which the sera from a peak antibody response sample was diluted to produce an optical density between 0.6–1.0. The diluted sera was added to triplicate wells of an ELISA plate coated with 1B4 as above. The sera was added alone, mixed with 5 μg of commercial mouse IgG2a, or mixed with 5 μg of 1B4. The ELISA was carried out as above and monkey antibody bound to the 1B4 on the plate was detected using HRP-anti-human IgG, as above. By comparing the optical density of signals produced by the uncompeted sera with those produced by sera spiked with mouse IgG2a or 1B4 it was possible to assess the specificity of the anti-1B4 antibodies which developed in animals treated with 1B4.

Measurement of Antibody Responses to S-S.1 (Irrelevant Isotype Control Antibody) Anti-S-S.1 Antibodies were Detected Using Two Assays, as Described Above.

Quantitative Angiography Calculations

Control of Bias

At the time of angioplasty and stenting, angiography measurements were performed. The measurement were taken in a non-blinded fashion to determine the diameter of each artery and to select the appropriate size balloon dilation catheter and inflation pressure for expansion of the stents, thus providing the desired balloon/stent:artery ratio. Non-blinded measurements were performed at follow-up. For the purpose of evaluating treatment effect(s), videorecorded images were replayed on a larger video screen and evaluated in a blinded fashion by an independent observer.

Angiography Measurements

Blinded angiography measurements were performed by measuring the fluoroscopy images directly from the video screen at the mid-stent area with digital calipers. For both iliac arteries, the following parameters were measured (in mm):

Angioplasty/stenting

Actual guide catheter o.d. (actual measurement) (a)

Observed guide catheter o.d. (observed on video screen as magnified image) (b)

Pre-angioplasty luminal i.d. (x)

Post-angioplasty in-stent inflated balloon o.d. (y)

Post-angioplasty/stent in-stent luminal i.d. (x')

Follow-up

Actual follow-up guide catheter o.d. (c)

Observed follow-up guide catheter o.d. (d)

Follow-up in-stent luminal i.d. (x")

Restenosis Calculations

The following calculations were performed:

Angioplasty/stenting

Magnification correction factor 1 (MCF1)=[b]÷[a]

Balloon/stent:artery ratio=[y:x]=1.1-1.2, ideally

Acute luminal gain (ALG; in mm)=[(x')(MCF1)]−[(x)(MCF1)]

Follow-up

Magnification correction factor 2 (MF2)=[d]÷[c]

Late luminal loss (LLL; in mm)=[(x')(MCF1)]−[(x")(MCF2)]

Arterial Tissue Analysis

Control of Bias

Arterial tissue samples were randomly assigned accession or identification numbers that did not indicate group or animal number. The person(s) evaluating arterial tissue samples for effect(s) of treatment were blinded to the identity of the samples.

Tissue Processing

The non-stented (balloon-injured) proximal and distal arterial segments were separated from the stented segments, with the proximal ends of each was identified and marked. Stented arterial segments were embedded in methacrylate and multiple 5 mm cross-sections were cut with a tungsten carbide knife. Non-stented arterial segments were embedded in paraffin to preserve antigenicity, but were not processed further unless warranted.

Stented sections were stained with verHoeff's tissue elastin stain, hematoxylin and eosin (H+E), and various immunocytochemical markers for cells incorporating BrdU or for cell types such as smooth muscle cells, endothelial cells, and inflammatory cells.

Evaluation of Neointimal Hyperplasia

In-stent cross-sectional neointimal (on the luminal side of the internal elastic membrane [IEL]) and medial (on the abluminal side of the IEL) areas (mm$^2$) were measured histomorphometrically using computer-assisted digital planimetry.[3] To minimize sampling error, 3 elastin-stained in-stent cross-sections, one each from the proximal, middle and distal portions of the right and left iliac arteries, were analyzed morphometrically. The composite value for the left or right artery was expressed as the mean value of the 3 measurements for each artery.

Each cross-section was scored (0–3) for the deep stent-induced arterial injury associated with each stent strut (8–12/cross-section) and an average depth of injury score for each cross-section was calculated.[19] These values were used to evaluate whether the initial injury was comparable across groups.

Statistical Analysis

Analysis of efficacy data by T-test between treated and control groups was performed and these values are reported.

RESULTS

Safety

There were no treatment-related effects on vital signs during infusion. There were no treatment-related effects on body weight or clinical observations during the study. Individual injection sites in one or more animals showed, mild, transient erythema which was not considered an adverse reaction. There were no adverse events associated with the catheterization incisions (i.e., no impairment of wound healing and no indication of bacterial infection). There were no adverse effects on clinical pathology parameters. As expected, serum globulin levels were elevated in treated and control animals. Leukocyte counts were affected by 1B4 and 1D9 administration (see below). There were no treatment-related gross lesions at necropsy.

Pharmacokinetics

Serum mAb levels (mean±stdev), Relative to Control mAb, are Presented in FIGS. 1A and 1B.

Administration of 1D9 resulted in serum concentrations >50 μg/mL at the time of angioplasty and stent deployment (Day 1) and maintenance of serum concentrations >1 μg/mL through Day 8. By Day 15, 1D9 levels were virtually undetectable, despite continuation of dosing from Day ⁻1 to 13.

Administration of 1B4 resulted in serum concentrations >50 μg/mL at the time of angioplasty and stent deployment (Day 1) and maintenance of serum concentrations >1 μg/mL through Day 8. By Day 15, 1B4 levels were virtually undetectable, despite continuation of dosing from Day ⁻1 to 13.

Pharmacodynamics

Leukocyte Target Saturation

Leukocyte target saturation (mean±stdev), relative to control mAb, is presented in FIGS. 2A–2C.

Leukocyte counts were not affected by administration of 1D9.

Administration of 1B4 resulted in rapid saturation of neutrophil and monocyte CD18 on Day ⁻1 immediately after IV infusion and maintenance of target saturation through Day 8. [Day ⁻8 levels were not available]. By Day 15, available CD18 binding sites on leukocytes (unsaturated targets) returned to baseline levels.

Peripheral Blood Leukocyte Dynamics

Peripheral blood leukocyte counts (mean±stdev), relative to control mAb, are presented in FIGS. 3A–3H.

Administration of 1D9 resulted in altered monocyte dynamics attributed to CCR2 saturation, as indicated by moderate monocytosis on Days 8 and 15. Although not determined, these cell counts were likely elevated at earlier timepoints as well. Other leukocytes were not affected.

Administration of 1B4 resulted in altered leukocyte dynamics attributed to CD18 saturation, as indicated by the pronounced leukocytosis, neutrophilia, lymphocytosis and monocytosis on Day 8. Although not determined, these cell counts were likely elevated at earlier timepoints as well.

Immunogenicity

Figure 4A:
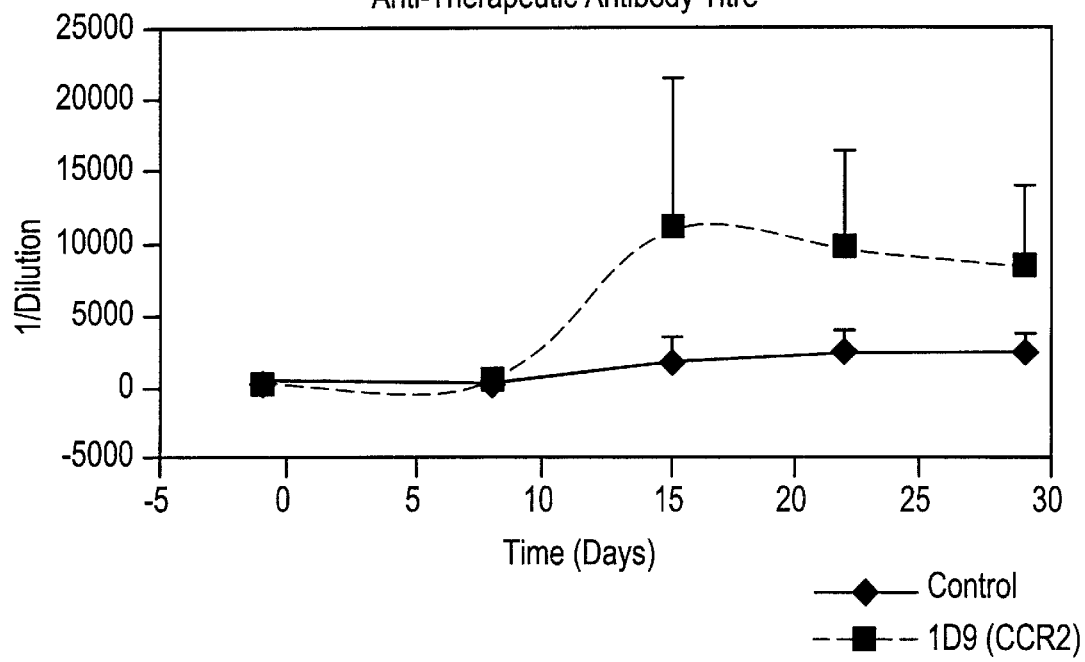
FIG. 4A is a graph showing the titer of anti-1D9 (1D9 (CCR2)) antibody or anti-S-S.1 antibody (control) in the serum of animals treated with mAb 1D9 or mAb S-S.1.
Figure 4B:
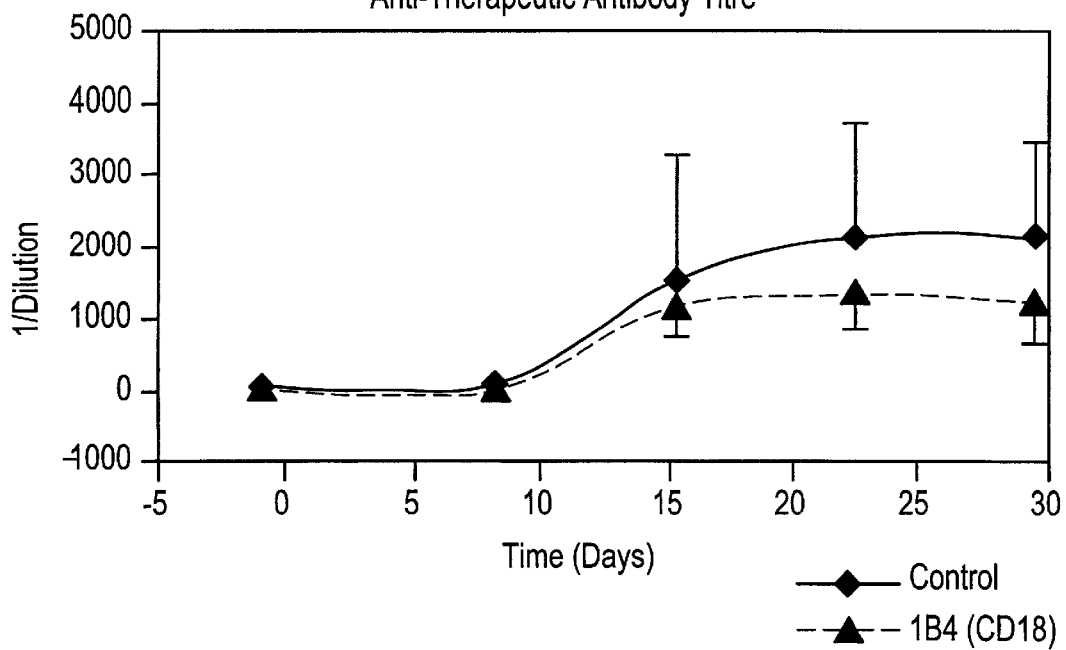
FIG. 4B is a graph showing the titer of anti-1B4 (1B4 (CD18)) antibody or anti-S-S.1 antibody (control) in the serum of animals treated with mAb 1B4 or mAb S-S.1.
Figure 5A:
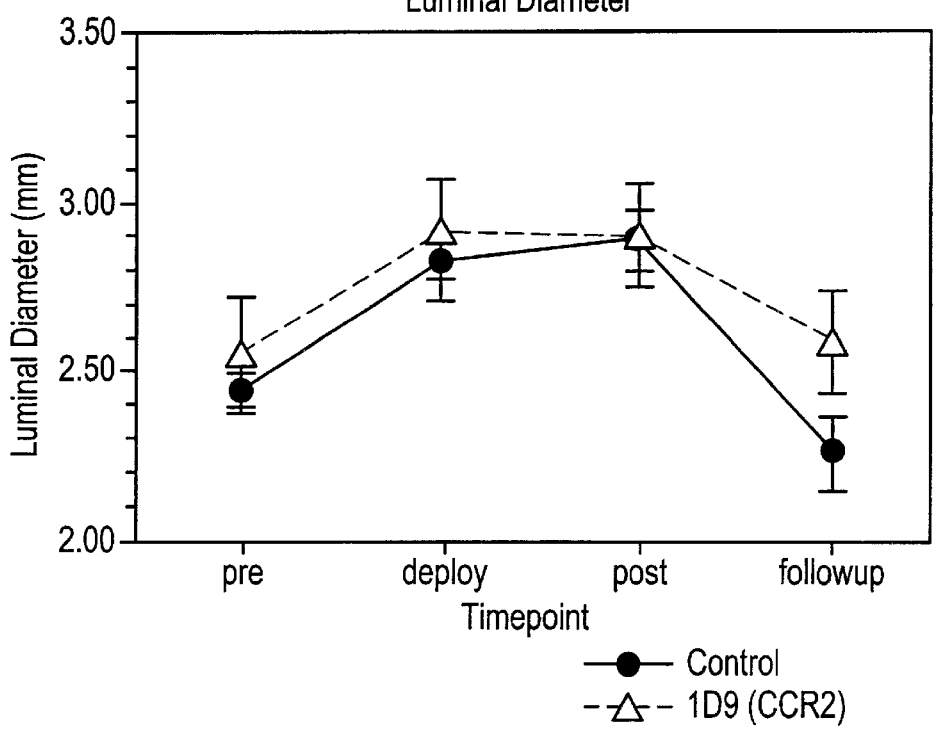
FIG. 5A is a graph showing the luminal diameter of iliac arteries of animals treated with mAb 1D9 or mAb S-S.1 (control). Measurements were taken before angioplasty (pre), at the time of stenting (deploy), about 10 minutes after placement of the stent (post) and 29 days after the procedure (followup).
Figure 5B:
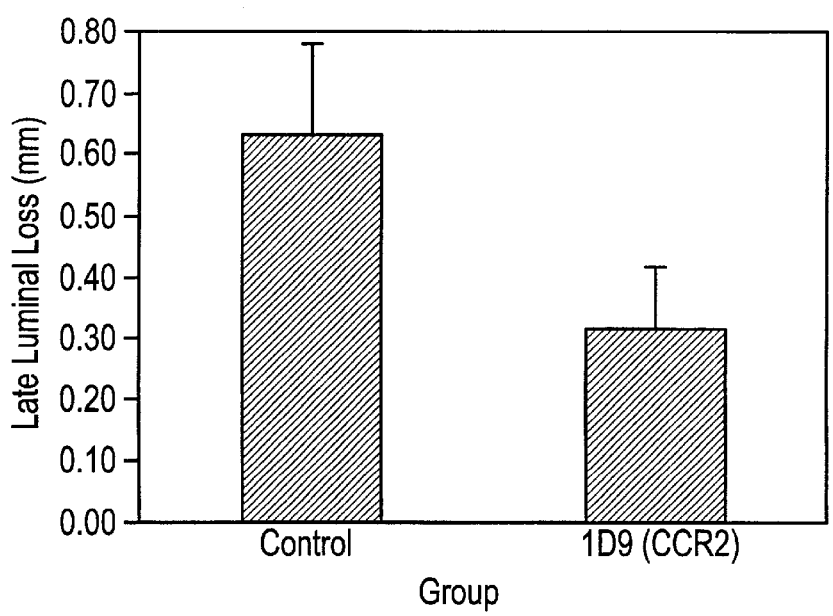
FIG. 5B is a histogram showing the late luminal loss at the site of angioplasty in animals treated with mAb S-S.1 (control) or mAb 1D9.
Figure 5C:
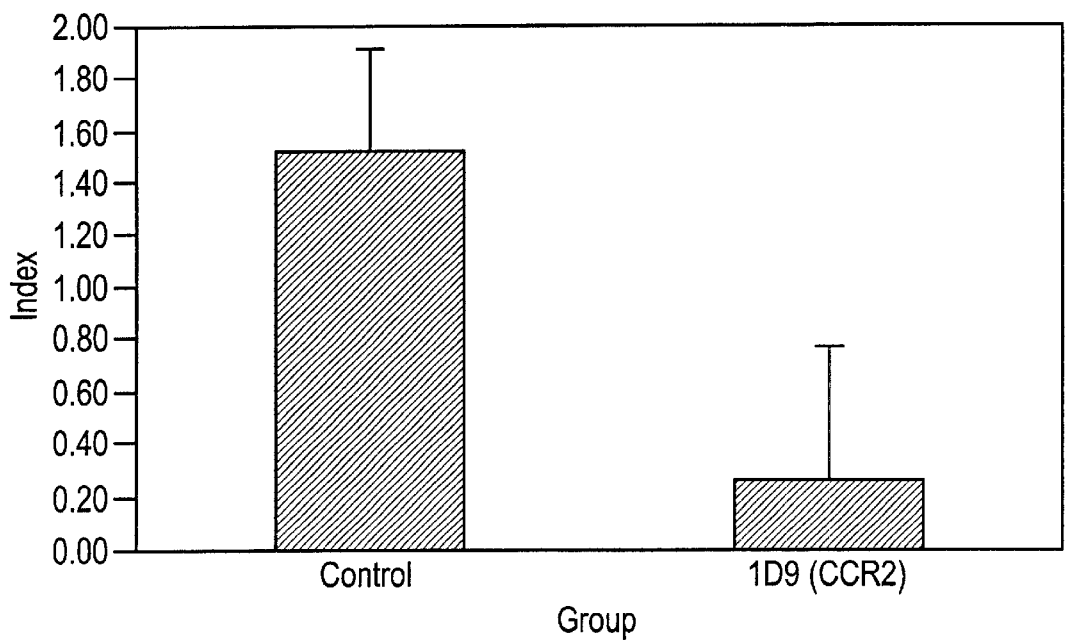
FIG. 5C is a histogram showing the restenosis index (late luminal loss (LLL)/actual luminal gain after stent deployment (ALG)) in animals treated with mAb S-S.1 (control) or mAb 1D9.
Figure 5D:
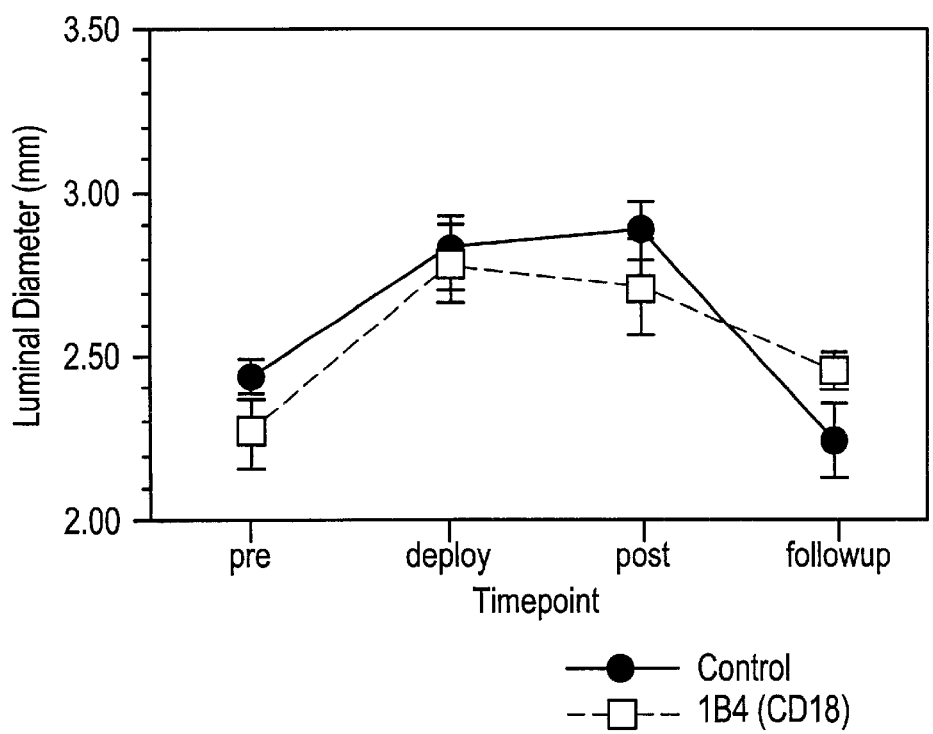
FIG. 5D is a graph showing the luminal diameter of iliac arteries of animals treated with mAb 1B4 or mAb S-S.1 (control). Measurements were taken before angioplasty (pre), at time of stenting (deploy), about 10 minutes after placement of the stent (post) and 29 days after the procedure (followup).
Figure 5E:
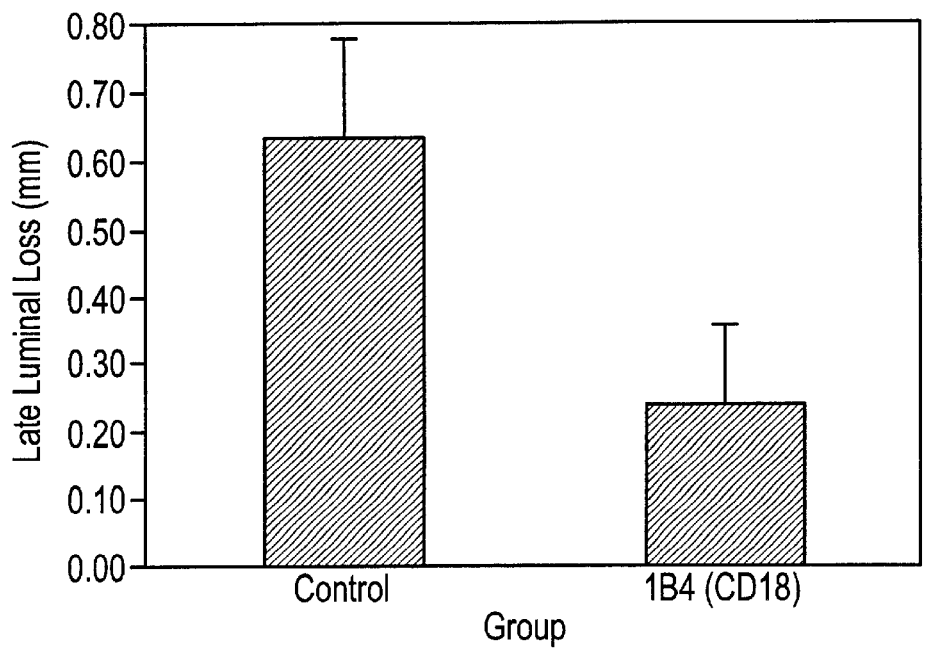
FIG. 5E is a histogram showing the late luminal loss at the site of angioplasty in animals treated with mAb S-S.1 (control) or mAb 1B4.
Figure 5F:
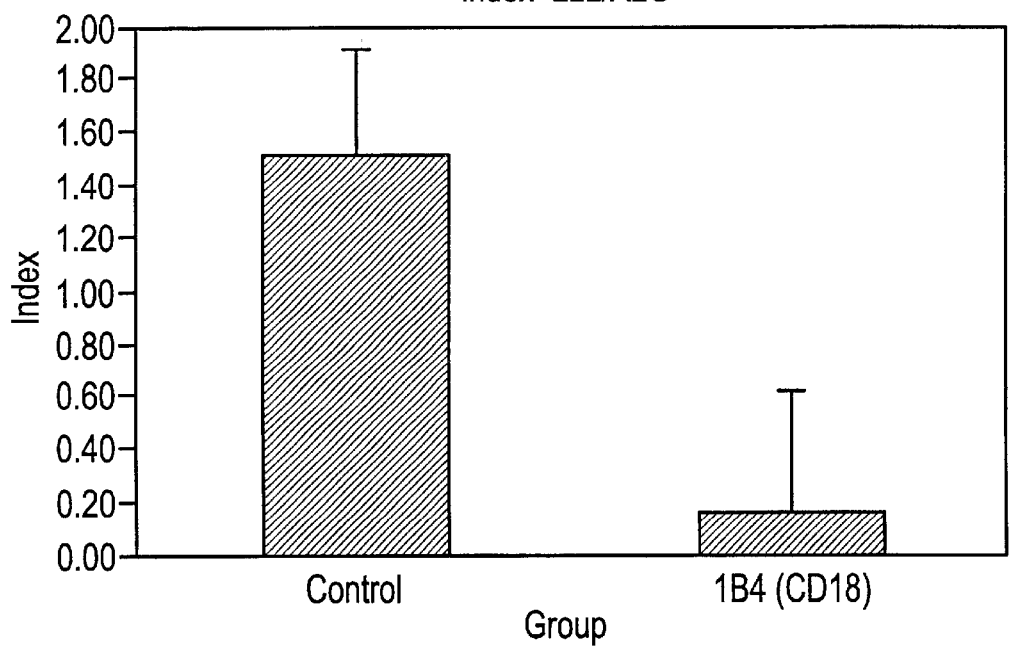
FIG. 5F is a histogram showing the restenosis index (late luminal loss (LLL)/actual luminal gain after stent deployment (ALG)) in animals treated with mAb S-S.1 (control) or mAb 1B4.
Figure 6A:
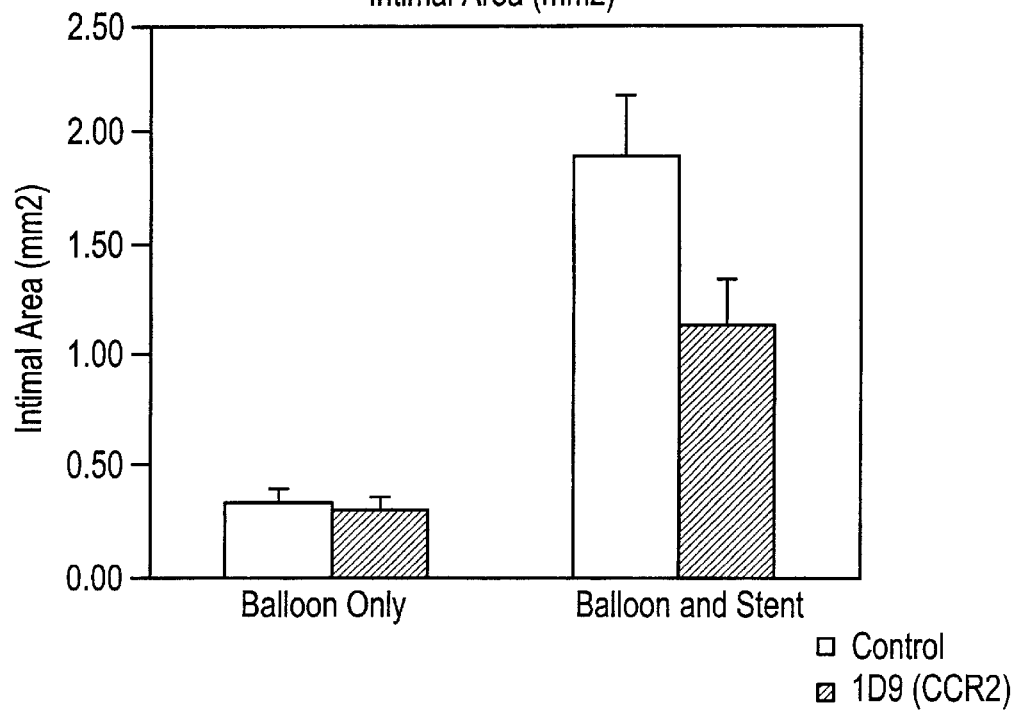
FIG. 6A is a histogram showing the intimal area ($mm^2$) measured in cross sections of vessels injured by balloon only or by balloon and stent in animals treated with mAb S-S.1 (control) or mAb 1D9.
Figure 6B:
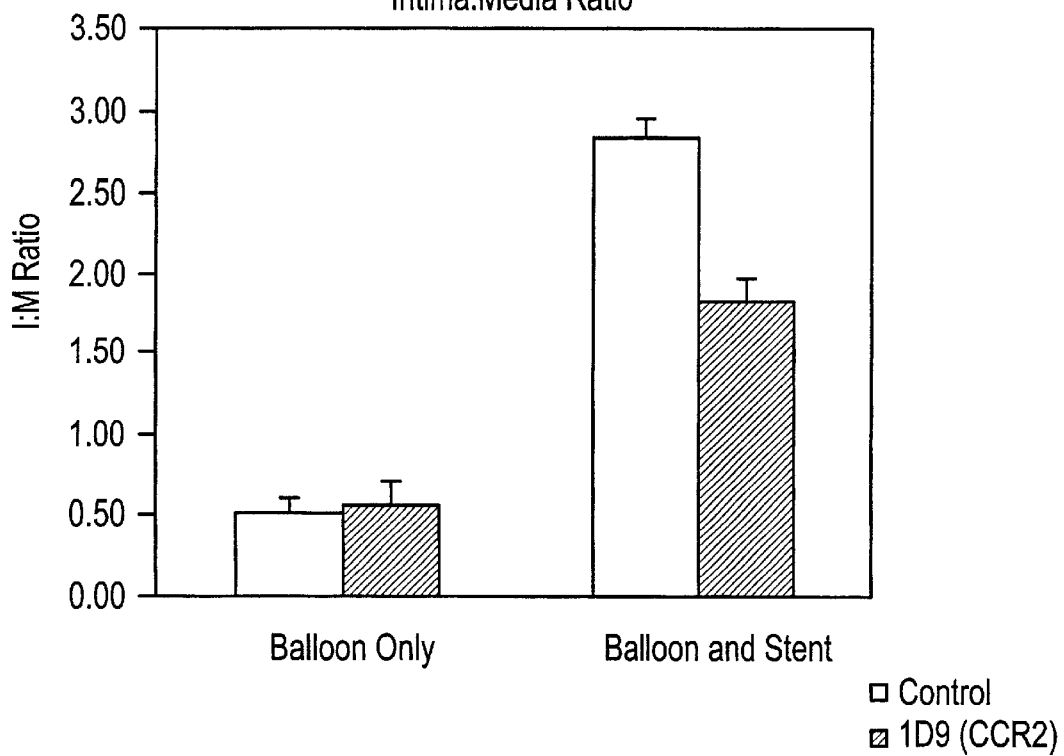
FIG. 6B is a histogram showing the intima:media ratio calculated from measurements on cross sections of vessels injured by balloon only or by balloon and stent in animals treated with mAb S-S.1 (control) or mAb 1D9.
Figure 6C:
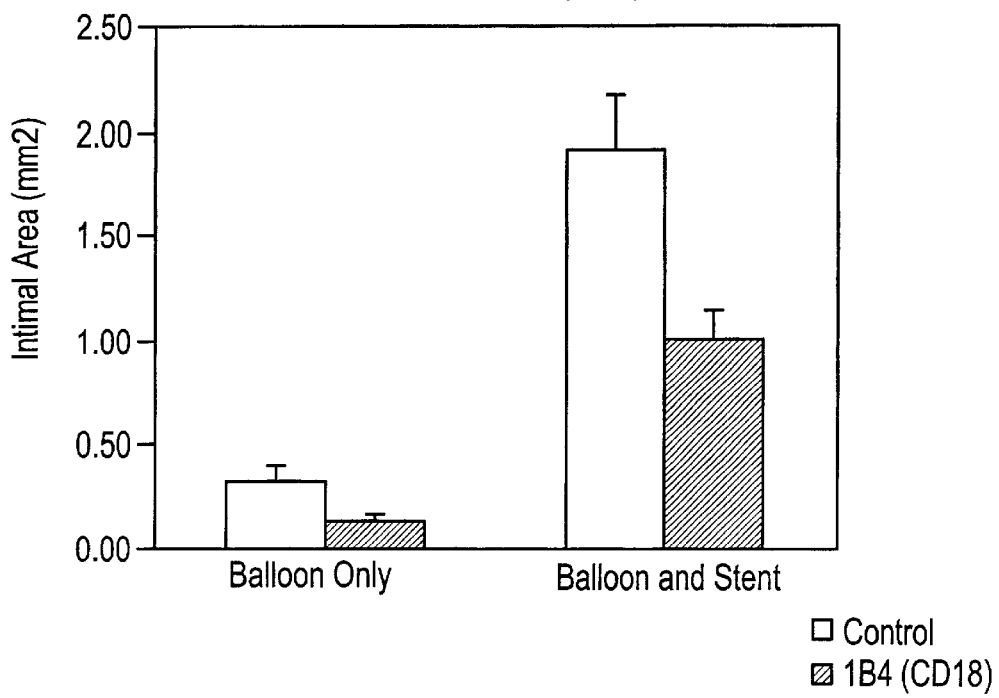
FIG. 6C is a histogram showing the intimal area ($mm^2$) measured in cross sections of vessels injured by balloon only or by balloon and stent in animals treated with mAb S-S.1 (control) or mAb 1B4.
Figure 6D:
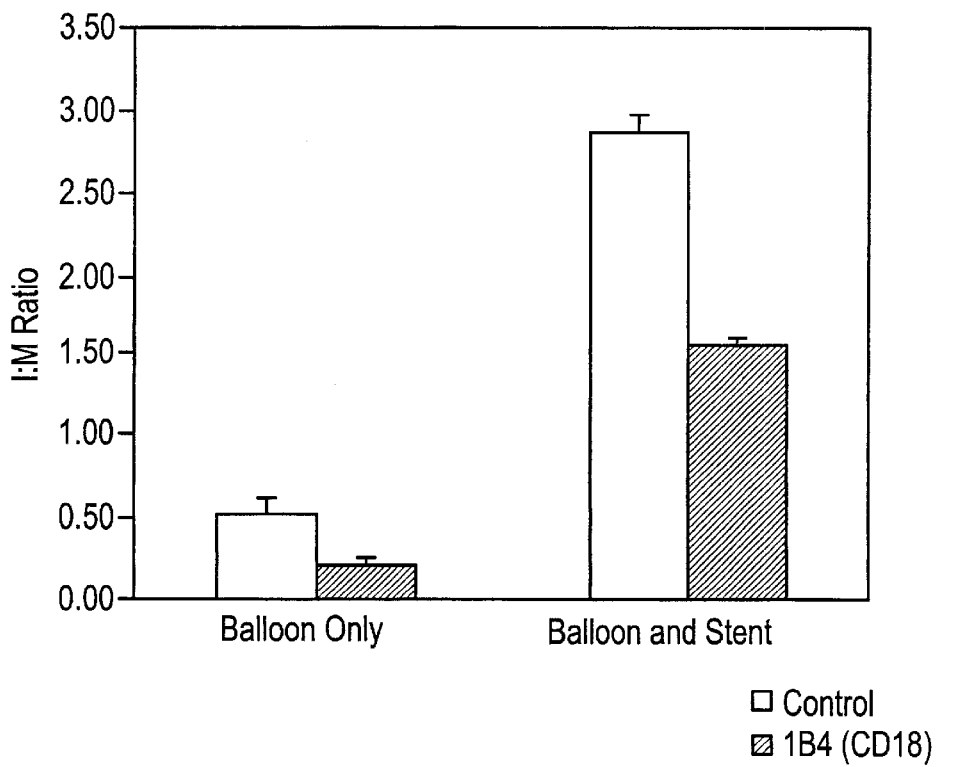
FIG. 6D is a histogram showing the intima:media ratio calculated from measurements on cross sections of vessels injured by balloon only or by balloon and stent in animals treated with mAb S-S.1 (control) or mAb 1B4.
Figure 7A:
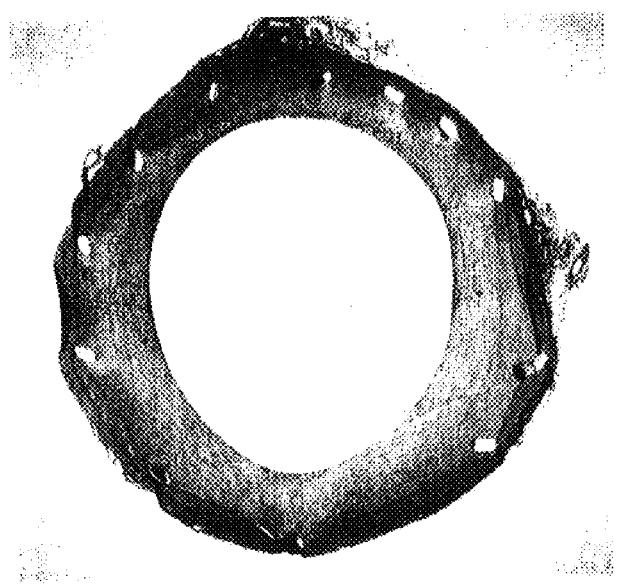
FIGS. 7A and 7B are photomicrographs of cross sections of vessels that underwent balloon injury and stent deployment in animals treated with mAb S-S.1 (control, FIG. 7A) or mAb 1D9 (FIG. 7B).
Figure 7B:
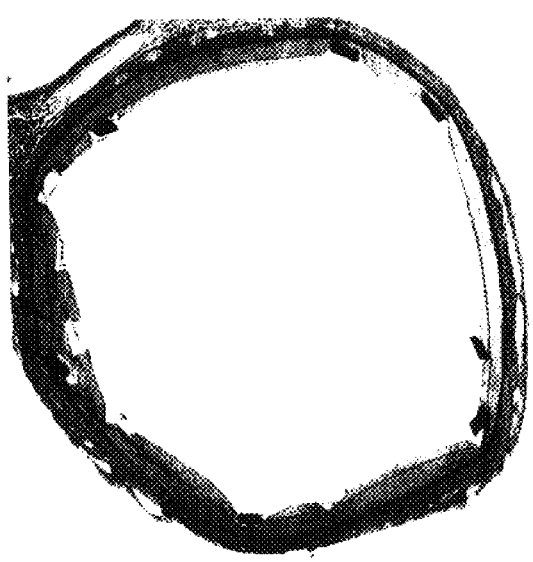
Figure 8A:
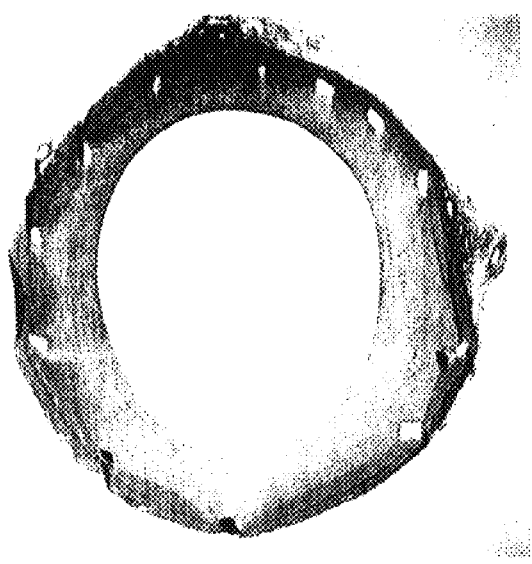
FIGS. 8A and 8B are photomicrographs of cross sections of vessels that underwent balloon injury and stent deployment in animals treated with mAb S-S.1 (control, FIG. 8A) or mAb 1B4 (FIG. 8B).
Figure 8B:
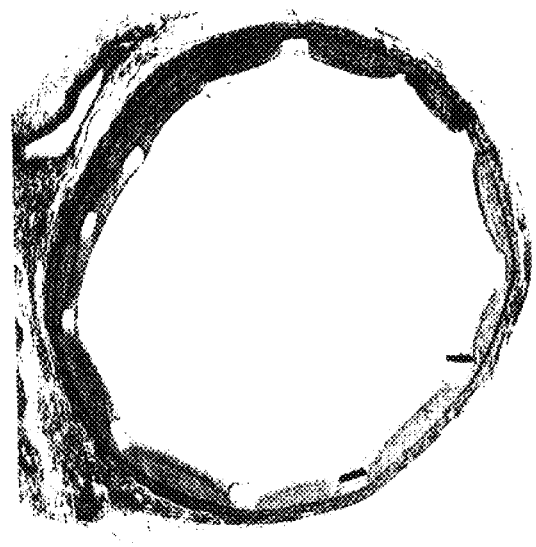

The anti-mAb antibody titers (mean±stdev), relative to control mAb, are presented in FIGS. 4A–4B.

Anti-globulin responses developed in all animals, detected as early as Day 8. The majority of these responses were anti-idiotype (directed against the variable region, specifically the complementarity determining region), rather than anti-isotype (directed against the constant region). The rapid increase in potentially neutralizing anti-idiotype antibodies from Day 8 to Day 15 corresponds with the loss of circulating mAb levels, the loss of leukocyte target saturation and the return of peripheral blood leukocyte counts to baseline (normal) levels. These observations are consistent with anti-mAb antibodies binding to the therapeutic mAb and preventing (neutralizing) the activity. Further, these observations suggest that effective sera/leukocyte levels of therapeutic mAb were only maintained through Day 8.

Efficacy

Quantitative Angiography

The blinded quantitative angiography results (mean±stdev), relative to control mAb, are presented in FIGS. 5A–5F.

Administration of 1D9 tended to decrease the late luminal loss (LLL) (p=0.11) and the index (LLL/ALG) (p=0.07) as measured at the mid-stent region of the iliac arteries, but this difference was not significant.

Administration of 1B4 tended to decrease the late luminal loss (LLL) (p=0.06) and significantly decreased the index (LLL/ALG) (p<0.05) as measured at the mid-stent region of the iliac arteries. Blockade of CD18 appeared to be more effective than blockade of CCR2, as measured by angiography.

Histomorphometric Analysis

The blinded histomorphometric analysis results (mean±stdev), relative to control mAb, are presented in FIGS. 6A–6D.

The blinded histomorphometric analysis results for intimal area (mm$^2$) and intima:media (I:M) ratio (mean±stdev), relative to control mAb, are presented in FIGS. 6A–6D. Severity scores indicated that there was no difference between groups in the degree of stent-mediated injury to the arteries, thus differences between groups are attributable to treatment and not to differences in degree of injury.

Administration of 1D9 inhibited neointimal hyperplasia within the balloon+stent, but not the balloon-only, segments of the iliac arteries (p=0.03 for intimal area, p=0.05 for I:M ratio). Because CCR2 is present on mononuclear cells (monocytes and activated T cells), but not neutrophils, these data suggest that mononuclear cells are important contributors to balloon+stent, but not balloon-only, neointimal hyperplasia. It does not exclude the possibility that other cells, not expressing CCR2, are contributors to balloon-only and balloon+stent neointimal hyperplasia. The observation of effective reduction of balloon+stent neointimal hyperplasia with anti-CCR2 inhibition may be relevant for balloon+stent (in-stent) restenosis in humans.

Administration of 1B4 inhibited neointimal hyperplasia within the balloon-only (p=0.02 for intimal area, p=0.01 for I:M ratio) and balloon+stent (p<0.01 for both intimal area and I:M ratio) segments of the iliac arteries. Because CD18 is present primarily on neutrophils, and to a lesser extent on mononuclear cells (monocytes and lymphocytes), these data suggest that neutrophils are important (and perhaps predominant) contributors to both balloon-only and balloon+stent neointimal hyperplasia. It does not exclude the possibility that other cells (i.e., mononuclear cells) expressing CD18 also are contributors to neointimal hyperplasia with either injury. The observation of effective reduction of balloon-only and balloon+stent neointimal hyperplasia with anti-CD18 inhibition may be relevant for balloon-only and balloon+stent (in-stent) restenosis in humans.

The results with 1D9 and 1B4 treatment demonstrate that CD18 blockade is effective in both balloon-only and balloon+stent neointimal hyperplasia, while CCR2 blockade is effective in balloon+stent injury only. CCR2 blockade appears slightly less effective than CD18 blockade in balloon+stent injury (as was seen with quantitative angiography). This is perhaps due to differences in immunogenicity and subsequent neutralizing effects (i.e., duration of effective blockade relative to target cell participation kinetics), or to the possibility that CCR2 blockade does not affect one or more of the cell types contributing to this lesion. Collectively, these results support the conclusion that neutrophils are important contributors in both types of injury, and that mononuclear cells are additional contributors to balloon+stent injury, but not balloon-only injury. It is therefore likely that simultaneous or sequential inhibition of both neutrophil and mononuclear cell participation, such as by combination therapy with an anti-CD18 and an anti-CCR2 agent, would be more effective for in-stent restenosis than either agent alone.

References Cited in Example
1. Code of Federal Regulations (CFR). Title 21; Part 58, Good Laboratory Practice Regulations: Final Rule. Washington (D.C.), Office of the Federal Register. Dec. 22, 1978 (Revised Apr. 1, 1993).
2. Holmes D R, Vlietstra R E, Smith H C, Vetrovec G W, Kent K M, Cowley M J, Faxon D P, Gruntzig A R, Kelsey S F, Detre K M, van Raden M J, Mock M B. Restenosis after percutaneous transluminal angioplasty (PTCA): a report from the PCTS registry from the National Heart, Lung and Blood Institute. Am J Cardiol 1984;53:77C–81C.
3. Serruys P W, Luitjen H E, Beatt K J, Geuskens R, de Feyter P J, van den Brand M, Reiber J H, ten Katen H J, van Es G A, Hugenholtz P G. Incidence of restenosis after successful coronary angioplasty: a time-related phenomenon: a quantitative angiographic study in 342 consecutive patients at 1, 2, 3, and 4 months. Circulation 1988;77:361–371.
4. Rogers C, Edelman E R, Simon D I. A mAb to the β2-leukocyte integrin Mac-1 (CD11b/CD18) reduces intimal thickening after angioplasty or stent implantation in rabbits. Proc Natl Acad Sci USA 1998;95:10134–10139.
5. Rogers C, Edelman E R: Endovascular stent design dictates experimental restenosis and thrombosis. Circulation 1995;91:2995–3001.
6. Ponath P. Chemokine receptor antagonists: novel therapeutics for inflammation and AIDS. Exp Opin Invest Drugs 1998;7:1–18.
7. Nelken N A, Coughlin S R, Gordon D, Wilcox J N. Monocyte chemoattractant protein-1 in human atheromatous plaques. J Clin Invest 1991;88:1121–1127.
8. Boring L, Gosling J, Cleary M, Charo I F. Decreased lesion formation in $CCR2^{-/-}$ mice reveals a role for chemokines in the initiation of atherosclerosis. Nature 1998;394:894–897.
9. Gu L, Okada Y, Clinton S K, Gerard C, Sukhova G K, Libby P, Rollins B J. Absence of monocyte chemoattractant protein-1 reduces atherosclerosis in low density lipoprotein receptor-deficient mice. Mol Cell 1998;2:275–281.
10. Furukawa Y, Matsumori A, Ohashi N, Shioi T, Ono K, Harada A, Matsushima K, Sasayama S. Anti-monocyte chemoattractant protein-1/monocyte chemotactant and activating factor antibody inhibits neointimal hyperplasia in injured rat carotid arteries. Circ Res 1999;84:306–314.
11. Kling D, Fingerle J, Harlan J M, Lobb R R, Lang F. Mononuclear leukocytes invade rabbit arterial intima during thickening formation via CD18- and VLA-4-dependent mechanisms and stimulate smooth muscle migration. Circ Res 1995;77:1121–8.
12. Kling D, Fingerle J, Harlan J M. Inhibition of leukocyte extravasation with a monoclonal antibody to CD18 during formation of experimental intimal thickening in rabbit carotid arteries. Arterioscler Thromb 1992;12:997–1007.
13. Golino P, Ambrosio G, Ragni M, Cirillo P, Esposito N, Willerson J T, Rothlein R, Petrucci L, Condorelli M, Chiariello M, Buja L M. Inhibition of leukocyte and platelet adhesion reduces neointimal hyperplasia after arterial injury. Thromb Haemostasis 1997;77:783–8.
14. Guzman L A, Forudi F, Villa A E, Topol E J. Role of leukocytes in neointimal formation after balloon angioplasty in the rabbit atherosclerotic model. Coronary Art Dis 1995;6:693–701.
15. United States Code. Title 7 U.S.C. Sections 2131–22159 (The Animal Welfare Act as amended by P.L. 99–198), effective Dec. 23, 1986.
16. Code of Federal Regulations (CFR). Title 9; Chapter 1, Subchapter A (Animal Welfare Standards), Final Rule, Parts 1–3. Washington (D.C.), Office of the Federal Register. Jan. 1, 1997.
17. National Research Council, Institute of Laboratory Animal Resources. Guide for the Care and Use of Laboratory Animals. Washington (D.C.): National Academy Press, 1996.
18. American Veterinary Medical Association. Report of the American Veterinary Association (AVMA) panel on euthanasia. J Am Vet Med Assoc 1993;202:229–249.
19. Schwartz R S, et al., Restenosis and Proportional Neointimal Response to Coronary Artery Injury: Results in a Porcine Model. J Am Coll Cardiol 1992;19:267–274.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of inhibiting stenosis or restenosis of a blood vessel following a vascular intervention procedure which includes the placement of a stent in a subject, comprising administering to said subject a therapeutically effective amount of a first therapeutic agent and a therapeutically effective amount of a second therapeutic agent, wherein said first therapeutic agent is an anti-CD18 antibody or antigen-binding fragment thereof which binds CD18 and inhibits binding of a ligand to an integrin which contains CD18, wherein said anti-CD18 antibody or antigen-binding fragment comprises light chain complementarity determining regions (CDR1, CDR2 and CDR3) of nonhuman origin, heavy chain complementarity determining regions (CDR1, CDR2 and CDR3) of nonhuman origin, and at least a portion of an immunoglobulin of human origin, wherein said light chain complementarity determining regions and said heavy chain complementarity determining regions have the amino acid sequences set forth below:

light chain:
   CDR1: the amino acid sequence of SEQ ID NO:2
   CDR2: the amino acid sequence of SEQ ID NO:3
   CDR3: the amino acid sequence of SEQ ID NO:4 heavy chain:
   CDR1: the amino acid sequence of SEQ ID NO:6
   CDR2: the amino acid sequence of SEQ ID NO:7
   CDR3: the amino acid sequence of SEQ ID NO:8;
   and said second therapeutic agent is an anti-CCR2 antibody or antigen-binding fragment thereof which binds CCR2 and inhibits binding of a ligand to said CCR2, wherein said anti-CCR2 antibody or antigen-binding fragment comprises light chain complementarity determining regions (CDR1, CDR2 and CDR3) of nonhuman origin, heavy chain complementarity determining regions (CDR1, CDR2 and CDR3) of nonhuman origin, and at least a portion of an immunoglobulin of human origin, wherein said light chain complementarity determining regions and said heavy chain complementarity determining regions have the amino acid sequences set forth below:

light chain:
- CDR1: the sequence of amino acids 24–39 of SEQ ID NO:11
- CDR2: the sequence of amino acids 55–61 of SEQ ID NO:11
- CDR3: the sequence of amino acids 94–102 of SEQ ID NO:11 heavy chain:
- CDR1: the sequence of amino acids 31–35 of SEQ ID NO:12
- CDR2: the sequence of amino acids 50–68 of SEQ ID NO:12
- CDR3: the sequence of amino acids 101–106 of SEQ ID NO:12.

2. The method of claim 1, wherein said anti-CD18 antibody or antigen-binding fragment comprises a light chain variable region having the amino acid sequence of SEQ ID NO:10 and heavy chain variable region having the amino acid sequence of SEQ ID NO: 9.

3. The method of claim 1, wherein said anti-CCR2 antibody or antigen-binding fragment comprises:
- a light chain variable region having the amino acid sequence of selected from the group consisting of SEQ ID NO: 14, SEQ ID NO: 15, SEQ ID NO: 16 and SEQ ID NO: 17 and SEQ ID NO: 18; and
- a heavy chain variable region having an amino acid sequence from the group consisting of SEQ ID NO: 20, SEQ ID NO: 21, SEQ ID NO: 22 and SEQ ID NO: 23.

4. The method of claim 3, wherein said light chain variable region has the amino acid sequence of SEQ ID NO: 14, and said heavy chain variable region has the amino acid sequence of SEQ ID NO: 20.

5. The method of claim 4, wherein said anti-CD18 antibody or antigen-binding fragment comprises a light chain variable region having the amino acid sequence of SEQ ID NO:10 and heavy chain variable region having the amino acid sequence of SEQ ID NO: 9.

* * * * *

UNITED STATES PATENT AND TRADEMARK OFFICE
CERTIFICATE OF CORRECTION

PATENT NO. : 6,663,863 B2
DATED : December 16, 2003
INVENTOR(S) : Christopher J. Horvath and Patricia E. Rao It is certified that error appears in the above-identified patent and that said Letters Patent is hereby corrected as shown below:

<u>Column 56,</u>
Line 8, delete "the" and insert -- an --;
Line 9, after "sequence" delete "of";
Line 10, delete "and" and insert -- , --;
Line 13, after "sequence" and insert -- selected --.

Signed and Sealed this

Twenty-fourth Day of February, 2004

JON W. DUDAS
*Acting Director of the United States Patent and Trademark Office*

SEQUENCE LISTING

<160> NUMBER OF SEQ ID NOS: 23

<210> SEQ ID NO 1
<211> LENGTH: 125
<212> TYPE: PRT
<213> ORGANISM: Unknown
<220> FEATURE:
<221> NAME/KEY: SITE
<222> LOCATION: (1)...(125)
<223> OTHER INFORMATION: YFC51.1 light chain variable region with
      signal sequence
<221> NAME/KEY: SIGNAL
<222> LOCATION: (1)...(20)
<223> OTHER INFORMATION: Rat

<400> SEQUENCE: 1

Met Arg Val Gln Val Gln Phe Leu Gly Leu Leu Leu Trp Thr Ser
 1               5                  10                  15

Gly Ala Gln Cys Asp Val Gln Met Thr Gln Ser Pro Ser Tyr Leu Ala
            20                  25                  30

Ala Ser Pro Gly Glu Ser Val Ser Ile Ser Cys Lys Ala Ser Lys Ser
        35                  40                  45

Ile Ser Asn Tyr Leu Ala Trp Tyr Gln Gln Lys Pro Gly Glu Ala Asn
    50                  55                  60

Lys Leu Leu Val Tyr Tyr Gly Ser Thr Leu Arg Ser Gly Ile Pro Ser
65                  70                  75                  80

Arg Phe Ser Gly Ser Gly Ser Gly Thr Asp Phe Thr Leu Thr Ile Arg
                85                  90                  95

Asn Leu Glu Pro Ala Asp Phe Ala Val Tyr Tyr Cys Gln Gln Tyr Tyr
            100                 105                 110

Glu Arg Pro Leu Thr Phe Gly Ser Gly Thr Lys Leu Glu
        115                 120                 125

<210> SEQ ID NO 2
<211> LENGTH: 11
<212> TYPE: PRT
<213> ORGANISM: Unknown
<220> FEATURE:
<221> NAME/KEY: SITE
<222> LOCATION: (1)...(11)
<223> OTHER INFORMATION: CDR1 of YFC51.1 light chain
<223> OTHER INFORMATION: Rat

<400> SEQUENCE: 2

Lys Ala Ser Lys Ser Ile Ser Asn Tyr Leu Ala
 1               5                  10

<210> SEQ ID NO 3
<211> LENGTH: 7
<212> TYPE: PRT
<213> ORGANISM: Unknown
<220> FEATURE:
<221> NAME/KEY: SITE
<222> LOCATION: (1)...(7)
<223> OTHER INFORMATION: CDR2 of YFC51.1 light chain
<223> OTHER INFORMATION: Rat

<400> SEQUENCE: 3

Tyr Gly Ser Thr Leu Arg Ser
 1               5

<210> SEQ ID NO 4
<211> LENGTH: 9

```
<212> TYPE: PRT
<213> ORGANISM: Unknown
<220> FEATURE:
<221> NAME/KEY: SITE
<222> LOCATION: (1)...(9)
<223> OTHER INFORMATION: CDR3 of YFC51.1 light chain
<223> OTHER INFORMATION: Rat

<400> SEQUENCE: 4

Gln Gln Tyr Tyr Glu Arg Pro Leu Thr
 1               5

<210> SEQ ID NO 5
<211> LENGTH: 139
<212> TYPE: PRT
<213> ORGANISM: Unknown
<220> FEATURE:
<221> NAME/KEY: SITE
<222> LOCATION: (1)...(139)
<223> OTHER INFORMATION: YFC51.1 heavy chain variable region
<221> NAME/KEY: SIGNAL
<222> LOCATION: (1)...(19)
<223> OTHER INFORMATION: Rat

<400> SEQUENCE: 5

Met Lys Cys Ser Trp Ile Asn Leu Phe Leu Met Ala Leu Ala Ser Gly
 1               5                  10                  15

Val Tyr Ala Glu Val Gln Leu Gln Gln Ser Gly Pro Glu Leu Arg Arg
            20                  25                  30

Pro Gly Ser Ser Val Lys Leu Ser Cys Lys Thr Ser Gly Tyr Ser Ile
        35                  40                  45

Lys Asp Tyr Leu Leu His Trp Val Lys His Arg Pro Glu Tyr Gly Leu
    50                  55                  60

Glu Trp Ile Gly Trp Ile Asp Pro Glu Asp Gly Glu Thr Lys Tyr Gly
65                  70                  75                  80

Gln Lys Phe Gln Ser Arg Ala Thr Leu Thr Ala Asp Thr Ser Ser Asn
                85                  90                  95

Thr Ala Tyr Met Gln Leu Ser Ser Leu Thr Ser Asp Asp Thr Ala Thr
            100                 105                 110

Tyr Phe Cys Thr Arg Gly Glu Tyr Arg Tyr Asn Ser Trp Phe Asp Tyr
        115                 120                 125

Trp Gly Gln Gly Thr Leu Val Thr Val Ser Ser
        130                 135

<210> SEQ ID NO 6
<211> LENGTH: 5
<212> TYPE: PRT
<213> ORGANISM: Unknown
<220> FEATURE:
<221> NAME/KEY: SITE
<222> LOCATION: (1)...(5)
<223> OTHER INFORMATION: CDR1 of YFC51.1 heavy chain
<223> OTHER INFORMATION: Rat

<400> SEQUENCE: 6

Asp Tyr Leu Leu His
 1               5

<210> SEQ ID NO 7
<211> LENGTH: 17
<212> TYPE: PRT
<213> ORGANISM: Unknown
<220> FEATURE:
<221> NAME/KEY: SITE
<222> LOCATION: (1)...(17)
```

```
<223> OTHER INFORMATION: CDR2 of YFC51.1 heavy chain
<223> OTHER INFORMATION: Rat

<400> SEQUENCE: 7

Trp Ile Asp Pro Glu Asp Gly Glu Thr Lys Tyr Gly Gln Lys Phe Gln
1               5                   10                  15

Ser

<210> SEQ ID NO 8
<211> LENGTH: 11
<212> TYPE: PRT
<213> ORGANISM: Unknown
<220> FEATURE:
<221> NAME/KEY: SITE
<222> LOCATION: (1)...(11)
<223> OTHER INFORMATION: CDR3 of YFC51.1 heavy chain
<223> OTHER INFORMATION: Rat

<400> SEQUENCE: 8

Gly Glu Tyr Arg Tyr Asn Ser Trp Phe Asp Tyr
1               5                   10

<210> SEQ ID NO 9
<211> LENGTH: 139
<212> TYPE: PRT
<213> ORGANISM: Artificial Sequence
<220> FEATURE:
<223> OTHER INFORMATION: Humanized heavy chain variable region with
      signal sequence

<400> SEQUENCE: 9

Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Arg
                20                  25                  30

Pro Ser Gln Thr Leu Ser Leu Thr Cys Thr Val Ser Gly Phe Thr Phe
            35                  40                  45

Thr Asp Tyr Leu Leu His Trp Val Arg Gln Pro Pro Gly Arg Gly Leu
        50                  55                  60

Glu Trp Ile Gly Trp Ile Asp Pro Glu Asp Gly Glu Thr Lys Tyr Gly
65                  70                  75                  80

Gln Lys Phe Gln Ser Arg Val Thr Met Leu Val Asp Thr Ser Lys Asn
                85                  90                  95

Gln Phe Ser Leu Arg Leu Ser Ser Val Thr Ala Ala Asp Thr Ala Val
            100                 105                 110

Tyr Tyr Cys Ala Arg Gly Glu Tyr Arg Tyr Asn Ser Trp Phe Asp Tyr
        115                 120                 125

Trp Gly Gln Gly Ser Leu Val Thr Val Ser Ser
    130                 135

<210> SEQ ID NO 10
<211> LENGTH: 127
<212> TYPE: PRT
<213> ORGANISM: Artificial Sequence
<220> FEATURE:
<223> OTHER INFORMATION: Humanized light chain variable region with
      signal sequence
<221> NAME/KEY: SIGNAL
<222> LOCATION: (1)...(19)

<400> SEQUENCE: 10

Met Gly Trp Ser Cys Ile Ile Leu Phe Leu Val Ala Thr Ala Thr Gly
1               5                   10                  15
```

```
Val His Ser Asp Ile Gln Met Thr Gln Ser Pro Ser Ser Leu Ser Ala
            20                  25                  30
Ser Val Gly Asp Arg Val Thr Ile Thr Cys Lys Ala Ser Lys Ser Ile
        35                  40                  45
Ser Asn Tyr Leu Ala Trp Tyr Gln Gln Lys Pro Gly Lys Ala Pro Lys
    50                  55                  60
Leu Leu Ile Tyr Tyr Gly Ser Thr Leu Arg Ser Gly Val Pro Ser Arg
65                  70                  75                  80
Phe Ser Gly Ser Gly Ser Gly Thr Asp Phe Thr Phe Thr Ile Ser Ser
                85                  90                  95
Leu Gln Pro Glu Asp Ile Ala Thr Tyr Tyr Cys Gln Gln Tyr Tyr Glu
            100                 105                 110
Arg Pro Leu Thr Phe Gly Gln Gly Thr Lys Val Glu Ile Lys Arg
        115                 120                 125

<210> SEQ ID NO 11
<211> LENGTH: 112
<212> TYPE: PRT
<213> ORGANISM: Unknown
<220> FEATURE:
<221> NAME/KEY: SITE
<222> LOCATION: (1)...(112)
<223> OTHER INFORMATION: Murine mAb 1D9 light chain variable region
<221> NAME/KEY: SITE
<222> LOCATION: (24)...(39)
<223> OTHER INFORMATION: CDR1
<221> NAME/KEY: SITE
<222> LOCATION: (55)...(61)
<223> OTHER INFORMATION: CDR2
<221> NAME/KEY: SITE
<222> LOCATION: (94)...(102)
<223> OTHER INFORMATION: CDR3
<223> OTHER INFORMATION: Mouse

<400> SEQUENCE: 11

Asp Val Val Met Thr Gln Thr Pro Leu Thr Leu Ser Val Thr Val Gly
 1               5                  10                  15

His Pro Ala Ser Ile Ser Cys Lys Ser Ser Gln Ser Leu Leu Asp Ser
            20                  25                  30

Asp Gly Lys Thr Phe Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Tyr Thr Phe Gly Gly Gly Thr Lys Leu Glu Ile Lys
            100                 105                 110

<210> SEQ ID NO 12
<211> LENGTH: 117
<212> TYPE: PRT
<213> ORGANISM: Unknown
<220> FEATURE:
<221> NAME/KEY: SITE
<222> LOCATION: (1)...(117)
<223> OTHER INFORMATION: Murine mAb 1D9 heavy chain variable region
<221> NAME/KEY: SITE
<222> LOCATION: (31)...(35)
<223> OTHER INFORMATION: CDR1
<221> NAME/KEY: SITE
<222> LOCATION: (50)...(68)
<223> OTHER INFORMATION: CDR2
<221> NAME/KEY: SITE
<222> LOCATION: (101)...(106)
<223> OTHER INFORMATION: CDR3
<223> OTHER INFORMATION: Mouse

<400> SEQUENCE: 12
```

-continued

```
Glu Val Gln Leu Val Glu Ser Gly Gly Gly Leu Val Gln Pro Lys Gly
 1               5                  10                  15

Ser Leu Lys Leu Ser Cys Ala Ala Ser Gly Phe Ser Phe Asn Ala Tyr
             20                  25                  30

Ala Met Asn Trp Val Arg Gln Ala Pro Gly Lys Gly Leu Glu Trp Val
         35                  40                  45

Ala Arg Ile Arg Thr Lys Asn Asn Tyr Ala Thr Tyr Tyr Ala Asp
    50                  55                  60

Ser Val Lys Asp Arg Tyr Thr Ile Ser Arg Asp Asp Ser Glu Ser Met
65                  70                  75                  80

Leu Phe Leu Gln Met Asn Asn Leu Lys Thr Glu Asp Thr Ala Met Tyr
                 85                  90                  95

Tyr Cys Val Thr Phe Tyr Gly Asn Gly Val Trp Gly Thr Gly Thr Thr
            100                 105                 110

Val Thr Val Ser Ser
            115
```

<210> SEQ ID NO 13
<211> LENGTH: 111
<212> TYPE: PRT
<213> ORGANISM: Homo sapiens

<400> SEQUENCE: 13

```
Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val His Ser
             20                  25                  30

Asp Gly Asn Thr Tyr Leu Asn Trp Phe Gln Gln Arg Pro Gly Gln Ser
         35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                 85                  90                  95

Thr His Trp Pro Phe Thr Phe Gly Gln Gly Thr Arg Leu Glu Ile
            100                 105                 110
```

<210> SEQ ID NO 14
<211> LENGTH: 112
<212> TYPE: PRT
<213> ORGANISM: Artificial Sequence
<220> FEATURE:
<223> OTHER INFORMATION: Humanized sequence

<400> SEQUENCE: 14

```
Asp Val Val Met Thr Gln Ser Pro Leu Ser Leu Pro Val Thr Leu Gly
 1               5                  10                  15

Gln Pro Ala Ser Ile Ser Cys Lys Ser Ser Gln Ser Leu Leu Asp Ser
             20                  25                  30

Asp Gly Lys Thr Phe Leu Asn Trp Phe Gln Gln Arg Pro Gly Gln Ser
         35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80
```

```
Ser Arg Val Glu Ala Glu Asp Val Gly Val Tyr Tyr Cys Trp Gln Gly
            85                  90                  95

Thr His Phe Pro Tyr Thr Phe Gly Gln Gly Thr Arg Leu Glu Ile Lys
            100                 105                 110

<210> SEQ ID NO 15
<211> LENGTH: 112
<212> TYPE: PRT
<213> ORGANISM: Artificial Sequence
<220> FEATURE:
<223> OTHER INFORMATION: Humanized sequence

<400> SEQUENCE: 15

Asp Val Val Met Thr Gln Ser Pro Leu Ser Leu Pro Val Thr Leu Gly
 1               5                   10                  15

Gln Pro Ala Ser Ile Ser Cys Lys Ser Ser Gln Ser Leu Leu Asp Ser
            20                  25                  30

Asp Gly Lys Thr Phe Leu Asn Trp Leu Leu Gln Arg Pro Gly Gln Ser
            35                  40                  45

Pro Arg Arg Leu Ile Tyr Leu Val Ser Lys Leu Asp Ser Gly Val Pro
            50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
            85                  90                  95

Thr His Phe Pro Tyr Thr Phe Gly Gln Gly Thr Arg Leu Glu Ile Lys
            100                 105                 110

<210> SEQ ID NO 16
<211> LENGTH: 112
<212> TYPE: PRT
<213> ORGANISM: Artificial Sequence
<220> FEATURE:
<223> OTHER INFORMATION: Humanized sequence

<400> SEQUENCE: 16

Asp Val Val Met Thr Gln Ser Pro Leu Ser Leu Pro Val Thr Leu Gly
 1               5                   10                  15

Gln Pro Ala Ser Ile Ser Cys Lys Ser Ser Gln Ser Leu Leu Asp Ser
            20                  25                  30

Asp Gly Lys Thr Phe Leu Asn Trp Leu Leu Gln Arg Pro Gly Gln Ser
            35                  40                  45

Pro Arg Arg Leu Ile Tyr Leu Val Ser Lys Leu Asp Ser Gly Val Pro
            50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
            85                  90                  95

Thr His Phe Pro Tyr Thr Phe Gly Gly Gly Thr Arg Leu Glu Ile Lys
            100                 105                 110

<210> SEQ ID NO 17
<211> LENGTH: 112
<212> TYPE: PRT
<213> ORGANISM: Artificial Sequence
<220> FEATURE:
<223> OTHER INFORMATION: Humanized sequence

<400> SEQUENCE: 17

Asp Val Val Met Thr Gln Ser Pro Leu Ser Leu Pro Val Thr Leu Gly
```

-continued

```
                 1               5                  10                 15
His Pro Ala Ser Ile Ser Cys Lys Ser Ser Gln Ser Leu Leu Asp Ser
                20                  25                 30

Asp Gly Lys Thr Phe Leu Asn Trp Leu Leu Gln Arg Pro Gly Gln Ser
            35                  40                  45

Pro Arg Arg Leu Ile Tyr Leu Val Ser Lys Leu Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gly Gly Thr Arg Leu Glu Ile Lys
            100                 105                 110
```

<210> SEQ ID NO 18
<211> LENGTH: 112
<212> TYPE: PRT
<213> ORGANISM: Artificial Sequence
<220> FEATURE:
<223> OTHER INFORMATION: Humanized sequence

<400> SEQUENCE: 18

```
Asp Val Val Met Thr Gln Ser Pro Leu Ser Leu Pro Val Thr Leu Gly
1               5                  10                 15

His Pro Ala Ser Ile Ser Cys Lys Ser Ser Gln Ser Leu Leu Asp Ser
                20                  25                 30

Asp Gly Lys Thr Phe Leu Asn Trp Leu Leu Gln Arg Pro Gly Gln Ser
            35                  40                  45

Pro Arg Arg Leu Ile Tyr Leu Val Ser Lys Leu Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gln Gly Thr Arg Leu Glu Ile Lys
            100                 105                 110
```

<210> SEQ ID NO 19
<211> LENGTH: 119
<212> TYPE: PRT
<213> ORGANISM: Homo sapiens

<400> SEQUENCE: 19

```
Glu Val Gln Leu Val Glu Ser Gly Gly Gly Leu Val Lys Pro Gly Gly
1               5                  10                 15

Ser Leu Arg Leu Ser Cys Ala Ala Ser Gly Phe Thr Phe Ser Asn Ala
                20                  25                 30

Trp Met Ser Trp Val Arg Gln Ala Pro Gly Lys Gly Leu Glu Trp Val
            35                  40                  45

Gly Arg Ile Lys Ser Lys Thr Asp Gly Gly Thr Thr Asp Tyr Ala Ala
        50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Asp Ser Leu Pro Pro His Arg Val Trp Gly Gln Gly
            100                 105                 110
```

```
Thr Leu Val Thr Val Ser Ser
            115

<210> SEQ ID NO 20
<211> LENGTH: 117
<212> TYPE: PRT
<213> ORGANISM: Artificial Sequence
<220> FEATURE:
<223> OTHER INFORMATION: Humanized sequence

<400> SEQUENCE: 20

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ala Tyr
            20                  25                  30

Ala Met Asn Trp Val Arg Gln Ala Pro Gly Lys Gly Leu Glu Trp Val
        35                  40                  45

Gly Arg Ile Arg Thr Lys Asn Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Phe Tyr Gly Asn Gly Val Trp Gly Gln Gly Thr Leu
            100                 105                 110

Val Thr Val Ser Ser
            115

<210> SEQ ID NO 21
<211> LENGTH: 117
<212> TYPE: PRT
<213> ORGANISM: Artificial Sequence
<220> FEATURE:
<223> OTHER INFORMATION: Humanized sequence

<400> SEQUENCE: 21

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Ser Phe Asn Ala Tyr
            20                  25                  30

Ala Met Asn Trp Val Arg Gln Ala Pro Gly Lys Gly Leu Glu Trp Val
        35                  40                  45

Gly Arg Ile Arg Thr Lys Asn Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Phe Tyr Gly Asn Gly Val Trp Gly Gln Gly Thr Leu
            100                 105                 110

Val Thr Val Ser Ser
            115

<210> SEQ ID NO 22
<211> LENGTH: 117
<212> TYPE: PRT
<213> ORGANISM: Artificial Sequence
<220> FEATURE:
<223> OTHER INFORMATION: Humanized sequence
```

<400> SEQUENCE: 22

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Asn Ala Tyr
            20                  25                  30

Ala Met Asn Trp Val Arg Gln Ala Pro Gly Lys Gly Leu Glu Trp Val
        35                  40                  45

Ala Arg Ile Arg Thr Lys Asn Asn Tyr Ala Thr Tyr Tyr Ala Asp
    50                  55                  60

Ser Val Lys Asp Arg Tyr Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Phe Tyr Gly Asn Gly Val Trp Gly Gln Gly Thr Leu
            100                 105                 110

Val Thr Val Ser Ser
        115

<210> SEQ ID NO 23
<211> LENGTH: 117
<212> TYPE: PRT
<213> ORGANISM: Artificial Sequence
<220> FEATURE:
<223> OTHER INFORMATION: Humanized sequence

<400> SEQUENCE: 23

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Asn Ala Tyr
            20                  25                  30

Ala Met Asn Trp Val Arg Gln Ala Pro Gly Lys Gly Leu Glu Trp Val
        35                  40                  45

Ala Arg Ile Arg Thr Lys Asn Asn Tyr Ala Thr Tyr Tyr Ala Asp
    50                  55                  60

Ser Val Lys Asp Arg Tyr Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Val Thr Phe Tyr Gly Asn Gly Val Trp Gly Gln Gly Thr Leu
            100                 105                 110

Val Thr Val Ser Ser
        115